United States Patent
Arai et al.

(10) Patent No.: US 10,786,207 B2
(45) Date of Patent: Sep. 29, 2020

(54) PHYSIOLOGICAL STATE DETERMINATION DEVICE AND PHYSIOLOGICAL STATE DETERMINATION METHOD

(71) Applicants: DAIKIN INDUSTRIES, LTD., Osaka-shi, Osaka (JP); TOKYO INSTITUTE OF TECHNOLOGY, Meguro-ku, Tokyo (JP)

(72) Inventors: Junichiro Arai, Osaka (JP); Takashi Gotou, Osaka (JP); Makoto Iwakame, Osaka (JP); Kenichi Hino, Osaka (JP); Tomoya Hirano, Osaka (JP); Takahiro Hirayama, Osaka (JP); Yasunori Kotani, Tokyo (JP); Yoshimi Ohgami, Tokyo (JP); Taro Tomatsu, Tokyo (JP)

(73) Assignees: Daikin Industries, Ltd., Osaka (JP); Tokyo Institute of Technology, Tokyo (JP)

(*) Notice: Subject to any disclaimer, the term of this patent is extended or adjusted under 35 U.S.C. 154(b) by 146 days.

(21) Appl. No.: 15/952,216

(22) Filed: Apr. 12, 2018

(65) Prior Publication Data

US 2018/0228447 A1    Aug. 16, 2018

Related U.S. Application Data

(63) Continuation of application No. PCT/JP2016/080757, filed on Oct. 17, 2016.

(30) Foreign Application Priority Data

Oct. 15, 2015 (JP) .................... 2015-203354
Feb. 29, 2016 (JP) .................... 2016-038481

(51) Int. Cl.
*A61B 5/00* (2006.01)
*A61B 10/00* (2006.01)
(Continued)

(52) U.S. Cl.
CPC .............. *A61B 5/7275* (2013.01); *A61B 5/01* (2013.01); *A61B 5/165* (2013.01); *A61B 5/4064* (2013.01);
(Continued)

(58) Field of Classification Search
CPC ......... A61B 5/7275; A61B 5/01; A61B 10/00; A61B 5/4064; A61B 5/165; G06T 7/0012; G06T 2207/30201; G06K 9/00302
See application file for complete search history.

(56) References Cited

U.S. PATENT DOCUMENTS 6,996,256 B2 * 2/2006 Pavlidis ................ A61B 5/015
382/118
2009/0285456 A1 * 11/2009 Moon ................ G06K 9/00335
382/118
(Continued)

FOREIGN PATENT DOCUMENTS

JP        8-215163 A     8/1996
JP     2008-220602 A     9/2008
(Continued)

OTHER PUBLICATIONS

Jarlier, Sophie, et al. "Thermal analysis of facial muscles contractions." IEEE transactions on affective computing 2.1 (2011): 2-9. (Year: 2011).*

(Continued)

*Primary Examiner* — Menatoallah Youssef
(74) *Attorney, Agent, or Firm* — Global IP Counselors, LLP

(57) ABSTRACT

A physiological state determination system includes a CPU and a camera. The camera acquires a photographic image data of a time-series change in facial data of a subject to which brain function activation information that activates (Continued)

human brain function was provided. The CPU determines a mental or physical physiological state of the subject based on facial change information corresponding to the photographic image data.

21 Claims, 35 Drawing Sheets

(51) Int. Cl.
*A61B 5/01* (2006.01)
*A61B 5/16* (2006.01)
*G06K 9/00* (2006.01)
*G06T 7/00* (2017.01)

(52) U.S. Cl.
CPC .......... *A61B 10/00* (2013.01); *G06K 9/00302* (2013.01); *G06T 7/0012* (2013.01); *G06T 2207/30201* (2013.01)

(56) References Cited

U.S. PATENT DOCUMENTS

| 2014/0121540 A1 | 5/2014 | Raskin |
| 2014/0200416 A1 | 7/2014 | Kashef et al. |
| 2015/0099987 A1 | 4/2015 | Bhatkar et al. |

FOREIGN PATENT DOCUMENTS

| JP | 2012-239661 A | 12/2012 |
| JP | 2013-176406 A | 9/2013 |
| JP | 2014-188168 A | 10/2014 |

OTHER PUBLICATIONS

Jarlier, Sophie, et al. "Thermal analysis of facial muscles contractions." IEEE transactions on affective computing 2.1 (2011): 2-9. (Year: 2011).*
International Search Report of corresponding PCT Application No. PCT/JP2016/080757 dated Jan. 10, 2017.
International Preliminary Report of corresponding PCT Application No. PCT/JP2016/080757 dated Apr. 26, 2018.
European Search Report of corresponding EP Application No. 16 855 569.6 dated Apr. 11, 2019.

* cited by examiner

_US 10,786,207 B2_

PHYSIOLOGICAL STATE DETERMINATION DEVICE AND PHYSIOLOGICAL STATE DETERMINATION METHOD

CROSS-REFERENCE TO RELATED APPLICATIONS

This application is a continuation application of International application PCT/JP2016/080757, which claims priority under 35 U.S.C. § 119(a) to Japanese Patent Application No. 2015-203354, filed in Japan on Oct. 15, 2015, and Japanese Patent Application No. 2016-038481, filed in Japan on Feb. 29, 2016, the entire contents of which are hereby incorporated herein by reference.

TECHNICAL FIELD

The present disclosure relates to a physiological state determination device and a physiological state determination method.

BACKGROUND ART

In the prior art, there are attempts at estimating human brain activity using data detected by electroencephalography (EEG), functional magnetic resonance imaging (fMRI), and near infrared spectroscopy (NIRS) as described in Japanese Unexamined Patent Application Publication No. 2013-176406. There are also studies on using estimated brain activity to determine human physical and mental states.

SUMMARY

However, with electroencephalography and near infrared spectroscopy, pretreatment, such as applying electrodes to a subject, is necessary. Additionally, functional magnetic resonance imaging must be conducted in a predetermined MRI room. In short, with these methods, preparation work is complicated and the measuring conditions are limited. The tremendous cost involved in these methods is also a problem. Consequently, these methods are difficult to use in the determination of the physical and mental states of a subject.

Thus, an object of the present disclosure is to provide a device and a method that enable the easy determination of the mental or physical physiological state of a subject.

A physiological state determination device according to the present disclosure includes a facial change information acquisition unit, a facial change information decomposition unit, and a physiological state determination unit. The facial change information acquisition unit acquires facial change information indicating time-series changes in facial data of a subject. The facial change information decomposition unit decomposes the facial change information into a plurality of components by singular value decomposition, principal component analysis, or independent component analysis. The physiological state determination unit determines a mental or physical physiological state of the subject on the basis of a determination component extracted from the plurality of components.

DETAILED DESCRIPTION OF EMBODIMENT(S)

Figure 1B:
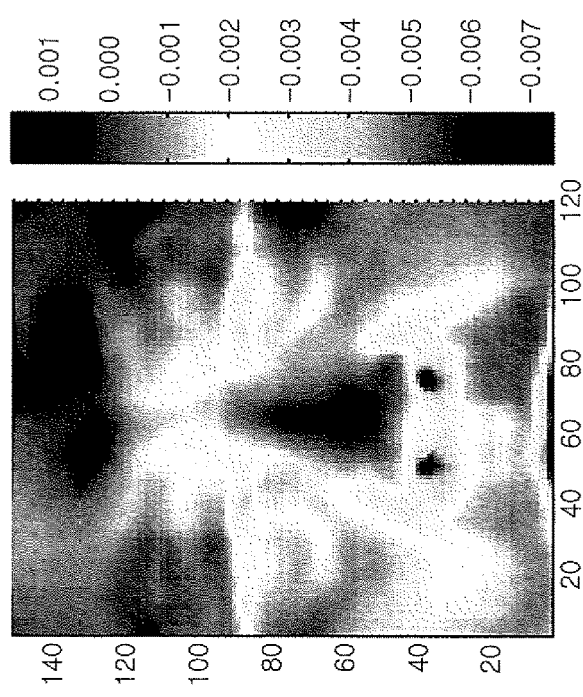
FIGS. 1A and 1B illustrate an example of photographic image data, and the results of analyzing the photographic image data.

Before describing the embodiments of the present disclosure, the findings made by the inventors that served as an important foundation for the inventors to contrive the present disclosure will be described.

(1) Summary of Findings Made by the Inventors

It is known that human intellectual activity (cognitive activity and the like) and emotional activity (activity such as pleasure/displeasure) are reflected in human brain activity. Attempts to estimate human brain activity have been made in the past, but in most cases, the attempts involved using data detected by electroencephalography, magnetic resonance imaging, and/or near infrared spectroscopy.

In cases where, for example, electroencephalography is adopted as the detection method, it is necessary to attach brain wave electrodes to the subject. Additionally, resistance that occurs between the skin and the electrodes when the brain wave electrodes are attached must be reduced. Consequently, a procedure such as a process to abrade the skin or an application of a paste to the electrodes needs to be carried out. In cases where functional magnetic resonance imaging is adopted, there are restrictions on measurement conditions, such as the impossibility of measurement at any location other than an MRI room and the inability to bring metal into the measurement room. In cases where near infrared spectroscopy is adopted, a probe needs to be attached to the subject. However, wearing the probe for a long time can be painful to the subject and. In some cases, due to contact state between the hair of the subject and the probe, the detections by the probe may not be accurate.

Thus, when using conventional detection methods to measure human brain activity, a significant burden is imposed on the subject, specifically, pretreatment is needed to attach the brain wave electrodes, probes, etc., and/or the measurement conditions are limited.

Accordingly, there is a need to develop an approach whereby the burden on the subject can be reduced and also whereby human brain activity can be easily estimated.

The inventors postulated that it might be possible to estimate human brain activity on the basis of human facial skin temperature or the state of facial blood circulation, which is thought to be proportional to the facial skin temperature. Human facial skin temperature can be acquired using a measurement device such as a thermography device. The state of facial blood circulation, that is, facial blood circulation volume can be estimated from RGB data of photographic images of the facial surface, which is obtained using an imaging device. The facial skin temperature and/or photographic images of the facial surface can be acquired without using electroencephalogram electrodes, probes, or other sensors that require pretreatment before being applied.

However, it is known that human facial skin temperature changes under the influence of various factors such as outside air temperature and/or autonomic nervous activity. As such, when attempting to estimate brain activity on the basis of the facial skin temperature or on the basis of the facial blood circulation volume, which is thought to be proportional to the facial skin temperature, it is very difficult to determine whether only brain activity is reflected in the acquired data.

After much research, the present inventors discovered that it is possible to identify a component indicating a change in the facial skin temperature or a change in the facial blood circulation volume in brain activity by: detecting the facial skin temperature; decomposing, into a plurality of components, time-series facial skin temperature data including the detected temperature data and position data (coordinate data) of the detection site, or decomposing, into a plurality of components, time-series facial blood circulation volume data calculated on the basis of RGB data obtained from time-series photographic image data of the facial surface, by singular value decomposition, principal component analysis, or independent component analysis; and analyzing the plurality of the decomposed components. Thus, the present inventors conceived the present disclosure, in which the brain activity of the subject is estimated and analyzed, thereby enabling the visualization of the physiological state of the subject on the basis of the estimated brain activity.

(2) Acquisition Method of Various Facial Data and Analysis Method of Acquired Various Facial Data (2-1) Acquisition Method of Facial Skin Temperature Data and Analysis Method of Facial Skin Temperature Data Next, a description is given of an acquisition method of facial skin temperature data and analysis method of facial skin temperature data used by the present inventors to reach the findings described above.

In this test, facial skin temperature data was acquired from six subjects. Specifically, each subject was seated in a chair placed in an artificial climate room maintained at a room temperature of 25° C., and facial skin temperature data was acquired from the entire facial surface of the subject using an infrared thermography device. The infrared thermography device was capable of detecting infrared radiant energy emitted from the subject using an infrared camera, converting the detected infrared radiant energy to a facial temperature (herein, the temperature in Celsius) of the subject, and displaying and/or storing a temperature distribution thereof as facial skin temperature data (e.g. image data representing the temperature distribution). In this test, an R300 (manufactured by NEC Avio Infrared Technologies Co., Ltd.) was used as the infrared thermography device. The infrared camera was set in front of the subject at a position 1.5 m away from the subject. The facial skin temperature data was acquired for 30 minutes.

Additionally, in this test, brain function activation tasks were given to the subjects while the facial skin temperature data was being acquired. Thus, facial skin temperature data during brain resting time and facial skin temperature data during brain activated time were acquired. The brain function activation tasks were presented to the subjects as images on a display device or the like. Examples thereof included calculation, recognition of numbers, shapes, and colors, memorization of symbols, letters, and language, and other psychological tasks. In this test, mental multiplication was used as the brain function activation task. The subjects were instructed to multiply numbers displayed in longhand on the display device, and input answers using a keyboard. In this test, the brain function activation tasks were continuously given to the subjects for ten minutes after five minutes had elapsed since the start of acquiring the facial skin temperature data.

To analyze the facial skin temperature data, the acquired facial skin temperature data was subjected to singular value decomposition. Here, Singular Value Decomposition (SVD) of MATLAB (registered trademark) was used as the analysis tool. In the singular value decomposition, the target was set as all of the time-series facial skin temperature data acquired (30-minutes of data), the factor was set as time data of every 30 seconds (60 time points for 30 minutes), and the measure was set as the facial skin temperature data (240×320 pixels) during each period (the 30 seconds). The facial skin temperature data X was decomposed into a plurality of components by singular value decomposition. Then, for each component, a time distribution V, a space distribution U, and a singular value S representing the magnitude of the component were calculated. The relationships between these values is expressed in the following equation. Note that V' is a matrix obtained by interchanging the columns and rows of V.

$$X=(U*S)*V'$$ Equation 1

Then, the time distribution V and the space distribution U of each component resulting from the singular value decomposition were plotted on graphs to create a component waveform diagram and a temperature distribution diagram for each component.

Furthermore, the component waveform diagram and the temperature distribution diagram for each component were analyzed to identify a component indicating a change in skin temperature that reflects brain activity.

The component waveform diagram for each component was analyzed to determine the presence/absence of correlation between the amplitude of the component waveform and each of the brain resting time and the brain activated time. Specifically, evaluations were conducted as to whether or not correlation existed between the amplitude shown in the component waveform diagram for each component and the brain resting time period/brain activated time period. In this test, during the period of acquiring the facial skin temperature data, the brain resting time was defined as a period of five minutes from the start of data acquisition and a period of 15 minutes from a point in time after 15 minutes had elapsed since the start point of data acquisition to the end of data acquisition. These were periods in which the brain function activation task was not given to the subjects. Additionally, the brain activated time was defined as a period of 10-minutes from a point in time occurring after five minutes had elapsed since the start of data acquisition, up to a point in time after 10 minutes had elapsed. This was a period in which the brain function activation task was being given to the subjects. Then, evaluations were conducted to determine the presence/absence of correlation between the amplitude shown in the component waveform diagram for each component and each of the brain resting time and the brain activated time. Note that statistical correlation analysis was performed to determine the presence/absence of correlation. When the significance level (a) was 0.05 or lower, it was determined that correlation existed. The temperature distribution diagram for each component was analyzed to determine the presence/absence of temperature changes at a predetermined site on the facial surface. The brain has a mechanism called the selective brain cooling system whereby the brain is cooled independently of body temperature. The selective brain cooling system is known to discharge heat generated by brain activity using the forehead and the area around the paranasal sinuses (including the area between the eyebrows and the area around the nose). As such, in this test, the temperature distribution diagram for each component was evaluated to determine the presence/absence of temperature changes at the forehead and the area around the paranasal sinuses. Note that, in the temperature distribution diagrams, the presence/absence of temperature changes at the forehead and the area around the paranasal sinuses was evaluated on the basis of visual inspection, or on the basis of whether or not the temperatures of the forehead and the area around the paranasal sinuses differed one standard deviation (SD) or more from the average temperature of all measurement data of the temperatures of the forehead and the area around the paranasal sinuses.

Additionally, polarity (positive or negative) of the facial skin temperature data X is determined by the relationships between the values of the space distribution U, the singular value S, and the time distribution V. As such, in some cases, polarity may appear inverted in the temperature distribution diagram and the component waveform diagram for each component. Therefore, polarity was not considered when evaluating the component waveform diagrams and the temperature distribution diagrams.

As described above, in this case, the infrared thermography device converts the infrared radiant energy detected from the subject into temperatures, and uses the temperature distribution thereof as the facial skin temperature data. However, when acquiring the facial skin temperature of a human subject using the infrared thermography device, various temperature changes unrelated to brain activity (i.e. noise), such as facial movements and/or autonomic nervous activity, are also acquired as the facial skin temperature data (see FIG. 1A). Therefore, in order to detect such temperature changes that are unrelated to brain activity, relative facial skin temperature data was created for which an average of all of the temperature data included in the facial skin temperature data of every 30 seconds is set to "0", the created facial skin temperature data was also subjected to singular value decomposition in which the SVD of MATLAB (registered trademark) is used as the analysis tool, a component waveform diagram and a temperature distribution diagram for each component were created in accordance with the singular value S, and the diagrams were analyzed to identify a component indicating a change in skin temperature that reflects brain activity.

For the sake of convenience, in the following description, the facial skin temperature data, acquired by the infrared thermography device, is referred to as "facial skin temperature data based on temperature conversion data"; and the relative facial skin temperature data, for which the average of all of the temperature data included in the facial skin temperature data based on temperature conversion data obtained every predetermined time period (every 30 seconds in this test) is set to "0", is referred to as "facial skin temperature data based on relative temperature conversion data."

Additionally, for one of the six subjects, in addition to detecting the facial skin temperature using the infrared thermography device, electrodes were connected to the scalp of the subject and electroencephalograms were taken. An evaluation was conducted for correlation between the amplitude of the component waveform diagram and the amplitude of the β wave, which is known as a waveform that appears when awake or when the consciousness is nervous (brain wave in the 14 to 30 Hz frequency range). Note that, when taking the electroencephalogram, the electrodes were arranged at six sites (F3, F4, C3, C4, Cz, and Pz) specified by the International 10-20 System.

It is expected that the head of the subject may move vertically while the brain function activation task is given to the subject. If such movement occurs, the position of the face of the subject with respect to the infrared camera will change. Therefore, a control test was conducted on one subject in order to verify whether such changes in the position of the face influence the changes in skin temperature. In the control test to verify the influence of movement of the subject when acquiring the facial skin temperature data, the same infrared thermography device used in the test described above was used to acquire the facial skin temperature data of the subject. However, in this case, the subject was instructed also to operate the keyboard at random timings during the period in which the brain function activation task was not given (that is, during brain resting time). The facial skin temperature data based on temperature conversion data and the facial skin temperature data based on relative temperature conversion data acquired by the control test were also subjected to singular value decomposition in which the SVD of MATLAB (registered trademark) was used as the analysis tool, a component waveform diagram and a temperature distribution diagram for each component were created in accordance with the singular value S, and the diagrams were analyzed to identify a component indicating a change in skin temperature that reflects brain activity.

Figure 1A:
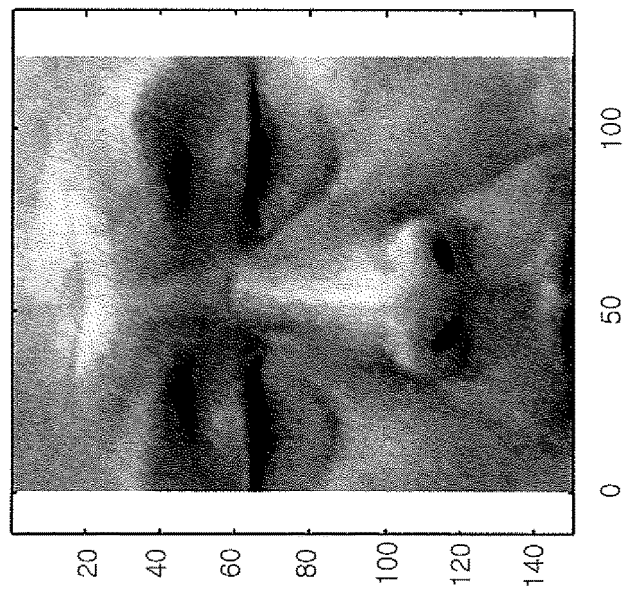

(2-2) Acquisition Method of Photographic Image Data of Facial Surface and Analysis Method of Photographic Image Data of Facial Surface FIG. 1A illustrates an example of photographic image data, captured using the imaging device, of the area around the paranasal sinuses of the facial surface of a subject. FIG. 1B illustrates an example of a blood circulation volume distribution diagram (image map).

Next, a description is given of an acquisition method of photographic image data of the facial surface and an analysis method of photographic image data of the facial surface used by the present inventors to reach the findings described above.

In this test, photographic image data of the facial surface was acquired from six subjects. Specifically, each subject was seated in a chair placed in an artificial climate room maintained at a room temperature of 25° C., and photographic image data of the area around the paranasal sinuses of the entire facial surface of the subject was acquired in time series using an imaging device capable of chronologically acquiring images.

Additionally, based on the selective brain cooling system described above, it is postulated that changes in the facial blood circulation volume, thought to be proportional to the facial skin temperature resulting from brain activity, will appear at the forehead and/or the area around the paranasal sinuses. As such, the present inventors postulated that, if the changes in the facial blood circulation volume at the forehead and/or the area around the paranasal sinuses could be at least captured, it would be possible to accurately estimate brain activity. Therefore, in this test, photographic image data was acquired of the area around the paranasal sinuses of the facial surfaces of the subjects were acquired in time series.

Additionally, in this test, an imaging device on the liquid crystal screen side of an iPad Air (registered trademark, manufactured by Apple) was used as the imaging device, and color video data was acquired as the time-series photographic image data. This imaging device was set in front of the subject at a position 1.0 m away from the subject. Then, using the imaging device, photographic image data was continuously captured for 30 minutes at an imaging period of 30 frames/second along the time axis. Thus, video data of the facial surface was acquired.

Furthermore, in this test, the brain function activation task was given to the subjects while the video data of the facial surface was being acquired. Thus, video data of the facial surface during brain resting time and video data of the facial surface during brain activated time were acquired. In this test, as in the test described above, "mental multiplication" was used as the brain function activation task. The subjects were instructed to multiply numbers displayed in longhand on the display device, and input answers using a keyboard. However, in this test, the brain function activation tasks were continuously given to the subjects for ten minutes after five minutes had elapsed since the start of acquiring the video data of the facial surface.

To analyze the video data of the facial surface, blood circulation volume data was calculated on the basis of RGB data obtained from the captured video data of the facial surface, and the calculated time-series blood circulation volume data was subjected to singular value decomposition for which the SVD of MATLAB (registered trademark) was used as the analysis tool. Here, in accordance with the CIE-L*a*b* color system, an erythema index "a*" that correlates with skin redness and hemoglobin amount was calculated from the RGB data of the image, and this erythema index a* was used as the blood circulation volume data. In the singular value decomposition, the target was set as the blood circulation volume data (the erythema index in this case) based on the RGB data acquired from all of the chronologically acquired video data (30 minutes of data), the factor was set as time data of every 30 seconds (60 time points for 30 minutes), and the measure was set as the erythema index calculated from the RGB data for each period (every 30 seconds) (the erythema index obtained by extracting frame data of one second every 30 seconds, and calculating on the basis of the average value of the RGB values obtained from the frame data; 240×320 pixels). The time-series blood circulation volume data based on the RGB data obtained from the video data of the facial surface was decomposed into a plurality of components by singular value decomposition. Then, for each component, a time distribution V, a space distribution U, and a singular value S representing the magnitude of the component was calculated. The relationships between these values are the same as those expressed in Equation 1 above.

Then, the time distribution V and the space distribution U of each component resulting from the singular value decomposition were plotted on graphs to create a component waveform diagram and a blood circulation volume distribution diagram for each component.

Furthermore, the component waveform diagram and blood circulation volume distribution diagram for each component were analyzed to identify a component indicating a change in the facial blood circulation volume, that is, an RGB change in the facial surface, that reflects brain activity.

The component waveform diagram for each component was analyzed to determine the presence/absence of correlation between the amplitude of the component waveform and each of the brain resting time and the brain activated time. Specifically, evaluations were conducted as to whether or not correlation existed between the amplitude shown in the component waveform diagram for each component and the brain resting time period/brain activated time period. In this test, during the period of acquiring the photographic image data of the facial surface, the brain resting time was defined as a period of five minutes from the start of data acquisition and a period of 15 minutes from a point in time after 15 minutes had elapsed since the start point of data acquisition to the end of data acquisition. These were periods in which the brain function activation task was not given to the subjects. Additionally, the brain activated time was defined as a period of 10-minutes from a point in time occurring after five minutes had elapsed since the start of data acquisition, up to a point in time after 10 minutes had elapsed. This was a period in which the brain function activation task was being given to the subjects. Then, evaluations were conducted to determine the presence/absence of correlation between the amplitude shown in the component waveform for each component and each of the brain resting time and the brain activated time. Note that statistical correlation analysis was performed to determine the presence/absence of correlation. When the significance level (a) was 0.01 or lower, it was determined that correlation existed.

The blood circulation volume distribution diagram for each component was analyzed to determine the presence/absence of blood circulation volume changes at a predetermined site on the facial surface. The blood circulation volume distribution diagrams were created by arranging the space distributions U, calculated by pixel, at the respective positions of the pixels. The blood circulation volume distribution diagram for each component thus created was evaluated to determine the presence/absence of changes in blood circulation volume at the forehead and the area around the paranasal sinuses. Note that, in the blood circulation volume distribution diagrams, the presence/absence of a change in blood circulation volume at the forehead and the area around the paranasal sinuses was evaluated on the basis of the presence/absence of the change in the blood circulation volume that was observed through visual inspection, or on the basis of the value of the blood circulation volume at the forehead and the area around the paranasal sinuses as shown FIG. 1B was not "0.000".

Additionally, polarity (positive or negative) of the blood circulation volume data X was determined by the relationships between the values of the space distribution U, the singular value S, and the time distribution V. As such, in some cases, polarity may appear inverted in the blood circulation volume distribution diagram and the component waveform diagram for each component. Therefore, polarity was not considered when evaluating the component waveform diagrams and the blood circulation volume distribution diagrams.

Furthermore, in order to validate the correlation between the facial skin temperature and the facial blood circulation volume, while the photographic image data of the facial surfaces of the six subjects was being chronologically acquired, the facial skin temperature data was chronologically acquired using the infrared thermography device, the acquired facial skin temperature data was subjected to singular value decomposition using the SVD of MATLAB (registered trademark) as the analysis tool, a component waveform diagram for each component was created in accordance with the singular value S, and the diagrams were analyzed to determine the presence/absence of correlation between the amplitude of the component waveform and each of the brain resting time and the brain activated time. In this test, the same device described above was used as the infrared thermography device. The infrared camera was set in front of the subject at a position 1.5 m away from the subject.

When acquiring the photographic image data of the facial surface using the imaging device, in some cases sunlight or the like strikes the facial surface while imaging, reflects off the facial surface, and this reflected light enters the lens of the imaging device. In such cases, this reflected light may be recorded in the captured photographic image data of the facial surface. Here, in the RBG data obtained from the photographic image data, changes in brightness based on the facial blood circulation volume are smaller than changes in brightness based on reflected light. Consequently, if blood circulation volume calculated on the basis of RGB data obtained from photographic image data with the reflected light recorded therein is analyzed, it is considered that the RGB changes in the facial surface unrelated to brain activity (i.e. noise) could be mixed into the data. Therefore, in order to prevent the mixing of such RGB changes in the facial surface that were unrelated to brain activity, relative blood circulation volume data was created from relative RGB data obtained by setting an average of all of the RGB data taken every 30 seconds at "0". Then, the thus-created blood circulation volume data was also subjected to singular value decomposition using the SVD of MATLAB (registered trademark) as the analysis tool, and the component waveform diagram and the blood circulation volume distribution diagram for each component were created in accordance with the singular value S. Then, the diagrams are analyzed to identify a component indicating the RGB change of the facial surface that reflects brain activity.

For the sake of convenience, in the following description, the relative blood circulation volume data based on relative RGB data, for which the average of all of the RGB data obtained every predetermined time period (every 30 seconds in this test) is set to "0", is referred to as "relative conversion blood circulation volume data"; whereas the blood circulation volume data based on the RGB data before converting to the relative RGB data is referred to simply as "blood circulation volume data."

Additionally, while acquiring the time-series photographic image data of the facial surfaces of the six subjects using the imaging device, electrodes were connected to the scalps of the subjects and electroencephalogram were taken. Evaluations were conducted for correlation between the amplitude of the component waveform diagrams and the amplitude of the β wave, which are known as a waveform that appears when awake or when brain cells are active (brain waves in the 13 to 30 Hz frequency range). Note that, when taking the electroencephalograms, the electrodes were arranged at 19 sites (Fp1, Fp2, F3, F4, C3, C4, P3, P4, O1, O2, F7, F8, T3, T4, T5, T6, Fz, Cz, and Pz) on the scalp specified by the International 10-20 System.

Furthermore, it is expected that the heads of the subjects may move vertically while the brain function activation task is given to the subjects. If such movement occurs, the positions of the faces of the subjects with respect to the imaging device will change. A control test was conducted on one subject in order to verify whether such changes in the position of the face influence the RGB changes in the facial surface. In the control test, as in the test described above, the imaging device was used to acquire the time-series photographic image data of the facial surface of the subject. However, in this case, the subject was instructed to operate the keyboard at random timings during the period in which the brain function activation task was not given (that is, during brain resting time). Furthermore, the time-series blood circulation volume data, based on the RGB data obtained from the time-series photographic image data of the facial surface captured in the control test, was subjected to singular value decomposition using the SVD of MATLAB (registered trademark) as the analysis tool, a component waveform diagram for each component was created in accordance with the singular value S. Then, the diagrams were analyzed to determine the presence/absence of correlation between the amplitude of the component waveform and each of the brain resting time and the brain activated time. Additionally, an analysis was conducted to determine the presence/absence of correlation between the amplitude of each component waveform and actual facial movement. The actual facial movement was evaluated by acquiring, from the photographic image data, a two-dimensional coordinate of a point corresponding to an actual point at the face, and calculating a movement distance of the face every 30 seconds during imaging. In these calculations, the photographic image data at the start of the control test was used as a reference. Furthermore, an analysis was also conducted to determine the presence/absence of correlation between the amplitude of each component waveform and the number of inputs on the keyboard during imaging. The number of inputs on the keyboard during imaging was evaluated by calculating a simple moving average every 30 seconds in the time-series photographic image data.

(3) Analysis Results
(3-1) Facial Skin Temperature Data Analysis Results

Figure 2A:
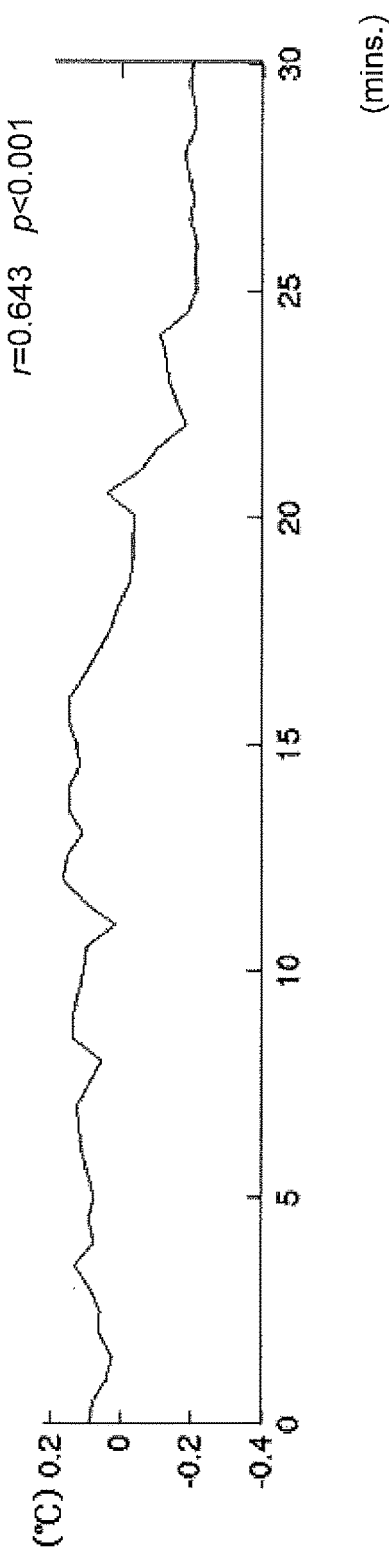
FIGS. 2A and 2B illustrate a portion of the results of analyzing facial skin temperature data.
Figure 2B:
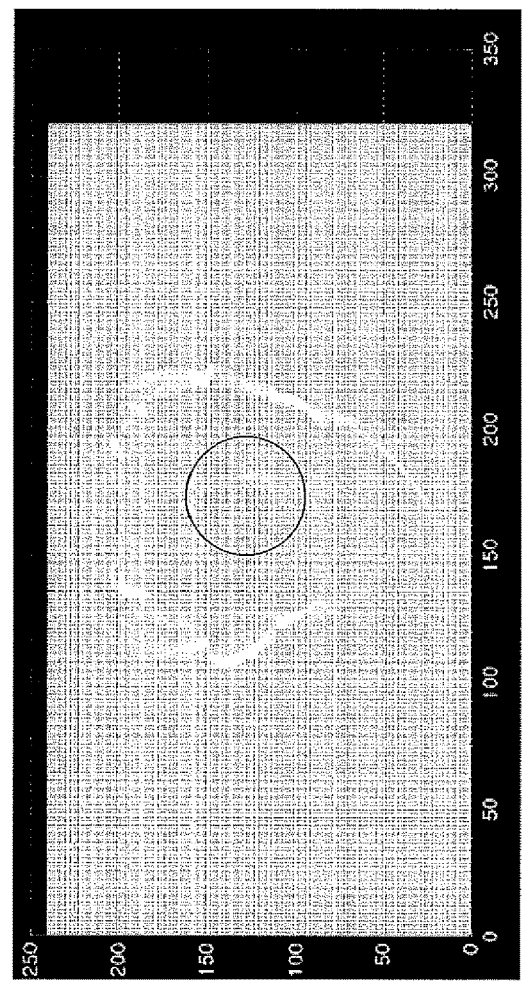
Figure 3A:
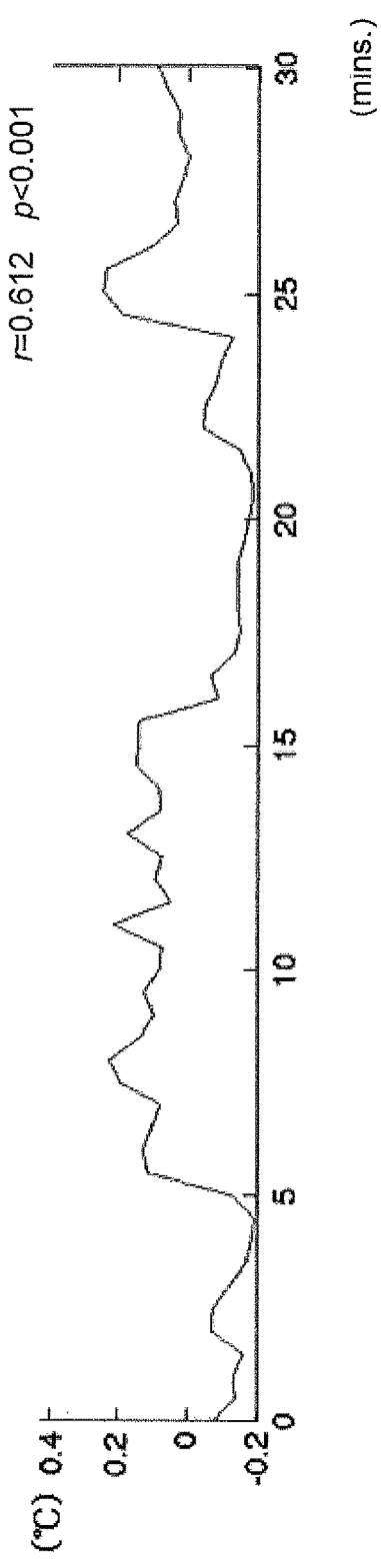
FIGS. 3A and 3B illustrate a portion of the results of analyzing the facial skin temperature data.
Figure 3B:
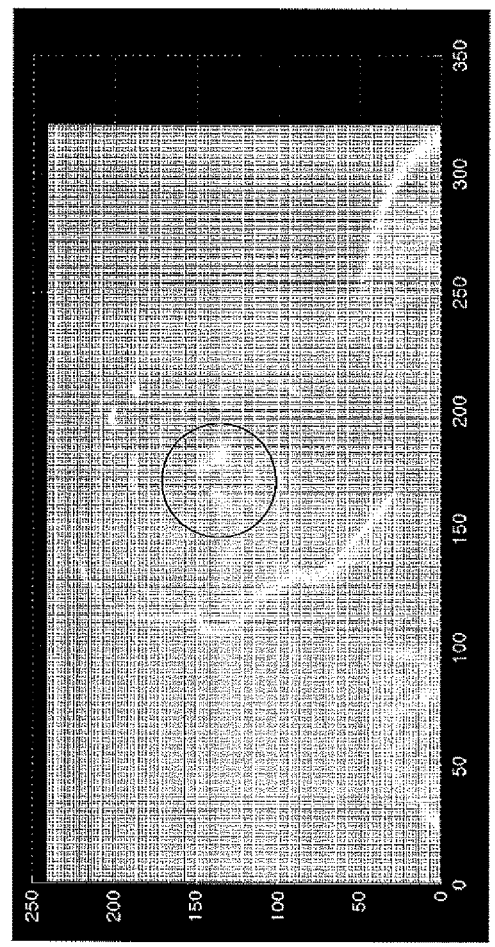
Figure 4:
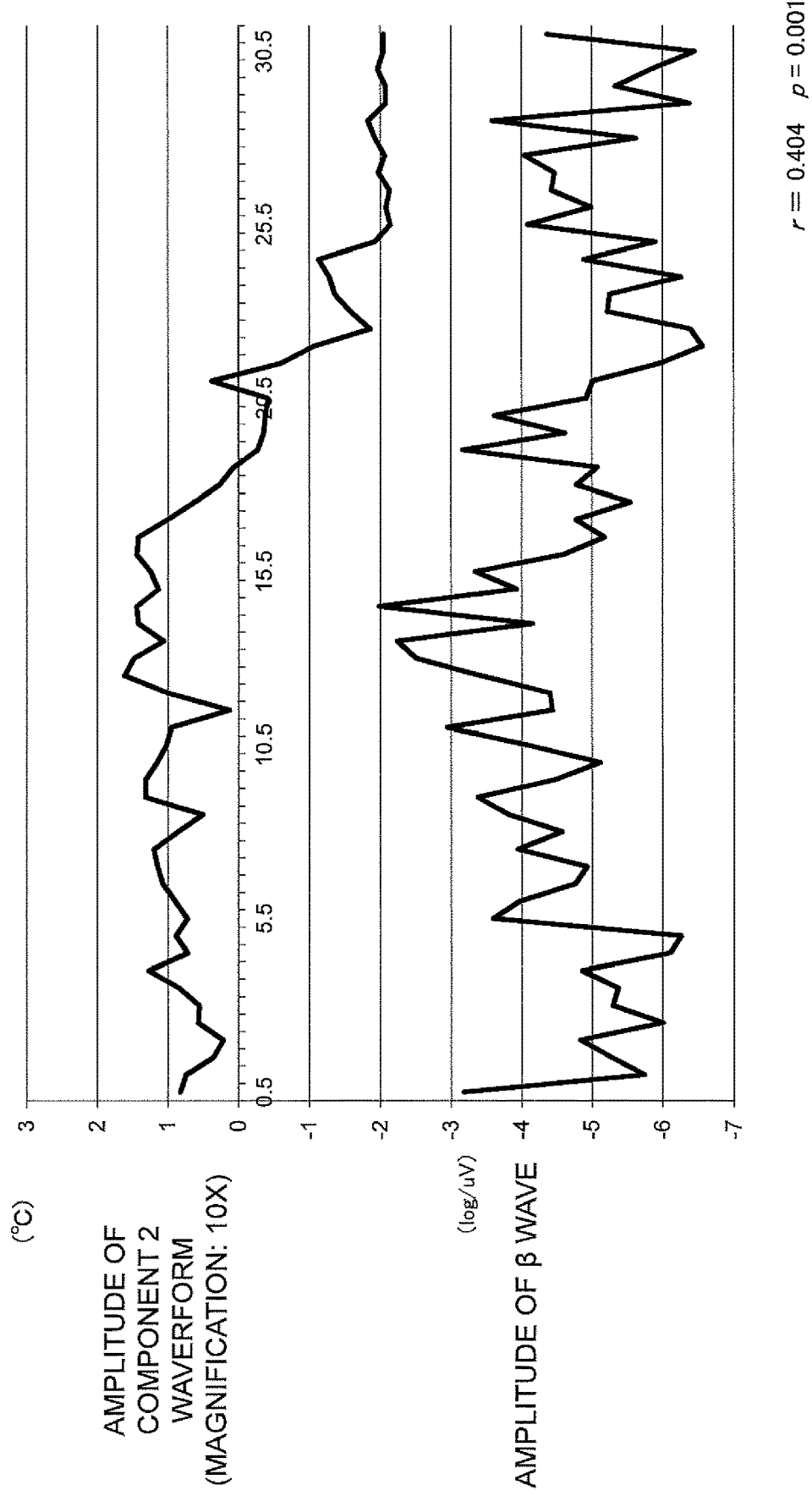
FIG. 4 is a chart illustrating the amplitude of a component waveform of a component 2, and the amplitude of the β wave of the measured brain waves.
Figure 5:
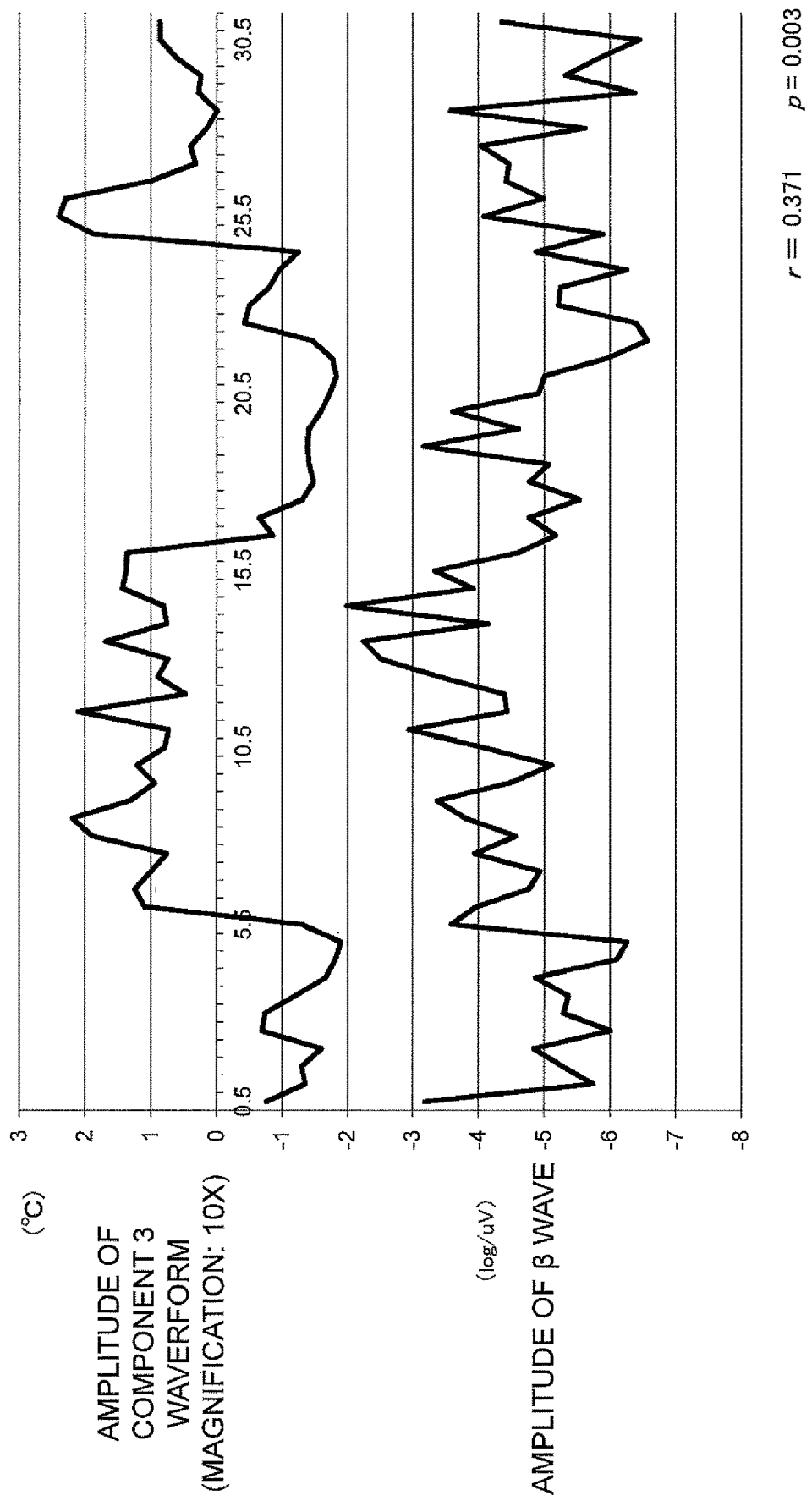
FIG. 5 is a chart illustrating the amplitude of a component waveform of a component 3, and the amplitude of the β wave of the measured brain waves.
Figure 6A:
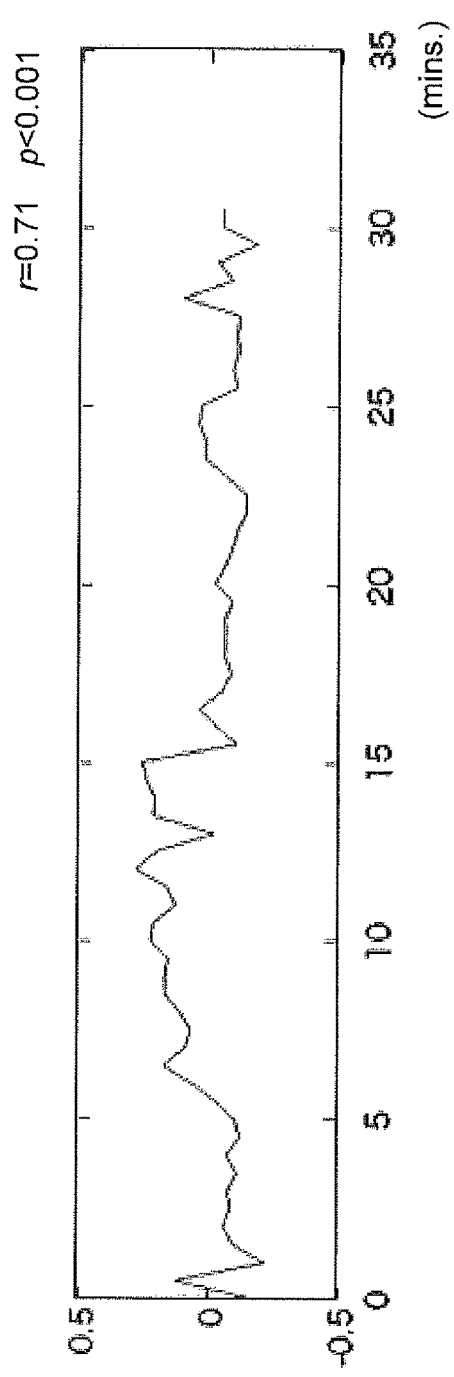
FIGS. 6A and 6B illustrate a portion of the results of analyzing the facial skin temperature data obtained in a control test.
Figure 6B:
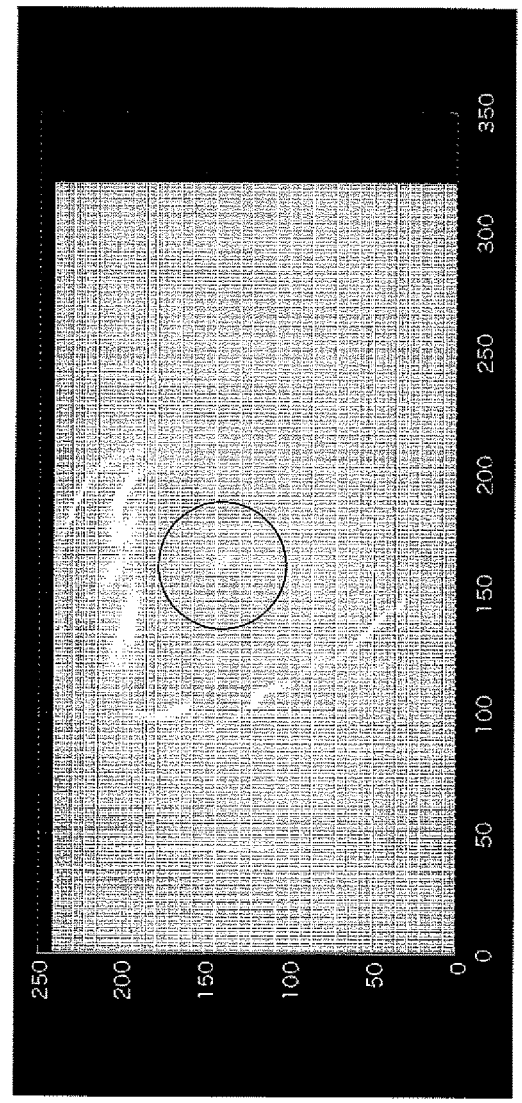

FIG. 2 illustrate a portion of the results of analyzing the facial skin temperature data based on the temperature conversion data. FIG. 2A illustrates the component waveform diagram of a component 2 of a subject 1. FIG. 2B illustrates the temperature distribution diagram of the component 2 of the subject 1. FIG. 3A illustrates the component waveform diagram of a component 3 of the subject 1. FIG. 3B illustrates the temperature distribution diagram of the component 3 of the subject 1. FIGS. 4 and 5 illustrate relationships between the amplitudes of the component waveforms and brain waves. FIG. 4 illustrates the amplitude of the component waveform of the component 2 of the subject 1, and the amplitude of the β wave of the measured brain waves. FIG. 5 illustrates the amplitude of the component waveform of the component 3 of the subject 1, and the amplitude of the β wave of the measured brain waves. FIGS. 6A and 6B illustrate a portion of the results of analyzing the facial skin temperature data obtained in the control test. FIG. 6A illustrates the component waveform diagram of the component 3. FIG. 6B illustrates the temperature distribution diagram of the component 3.

Table 1 shows the results of analyzing the facial skin temperature data for each subject.

From the results obtained by analyzing the facial skin temperature data described above, significant correlation was found between human brain activity and the component 2 and/or the component 3 of the plurality of components obtained by decomposing the time-series facial skin temperature data by singular value decomposition.

TABLE 1

| Subject | Correlation in Data Based on Absolute Temperature Conversion Data | | Correlation in Data Based on Relative Temperature Conversion Data | |
| --- | --- | --- | --- | --- |
| | Component waveform | Temperature distribution | Component waveform | Temperature distribution |
| Subject 1 | Component 2, Component 3 | Component 2, Component 3 | Component 2, Component 3 | Component 2, Component 3 |
| Subject 2 | Component 3 | Component 3 | Component 3 | Component 3 |
| Subject 3 | Component 1, Component 2, Component 3 | Component 2, Component 3 | Component 2, Component 3 | Component 2, Component 3 |
| Subject 4 | Component 2, Component 3 | Component 2, Component 3 | Component 2, Component 3 | Component 2, Component 3 |
| Subject 5 | Component 2, Component 3 | Component 2, Component 3 | Component 2, Component 3 | Component 2, Component 3 |
| Subject 6 | Component 2, Component 5 | Component 2, Component 5 | Component 2, Component 5 | Component 2, Component 5 |

As illustrated in FIGS. 4 and 5, from the results of analyzing the brain waves, significant correlation was found between the amplitude of the β wave of the brain waves and the amplitudes of the component 2 and the component 3.

Furthermore, in the control test, even in states where the subject moved while the facial skin temperature data was being acquired, there was significant correlation between the component 3 and human brain activity (see FIG. 6). From these results, it was found that movement by the subject when acquiring the facial skin temperature data does not influence the component 3 of the plurality of components.

Based on these results, the present inventors made the following findings.

The time-series facial skin temperature data acquired from the subjects was decomposed into the plurality of components by singular value decomposition. As a result of analyzing each of the decomposed components, it was found that the component 3 of the plurality of components is a component that is related to brain activity. Specifically, it was found that it is possible to identify a component indicating a change in skin temperature that reflects brain activity from the plurality of components by decomposing the time-series facial skin temperature data into the plurality of components by singular value decomposition, extracting components having correlation with the activation/resting of the brain from the decomposed plurality of components, and analyzing the extracted components using the selective brain cooling system. Thus, the present inventors found that it is possible to estimate brain activity on the basis of human facial skin temperature.

(3-2) Results of Analyzing Photographic Image Data of Facial Surface

Figure 7:
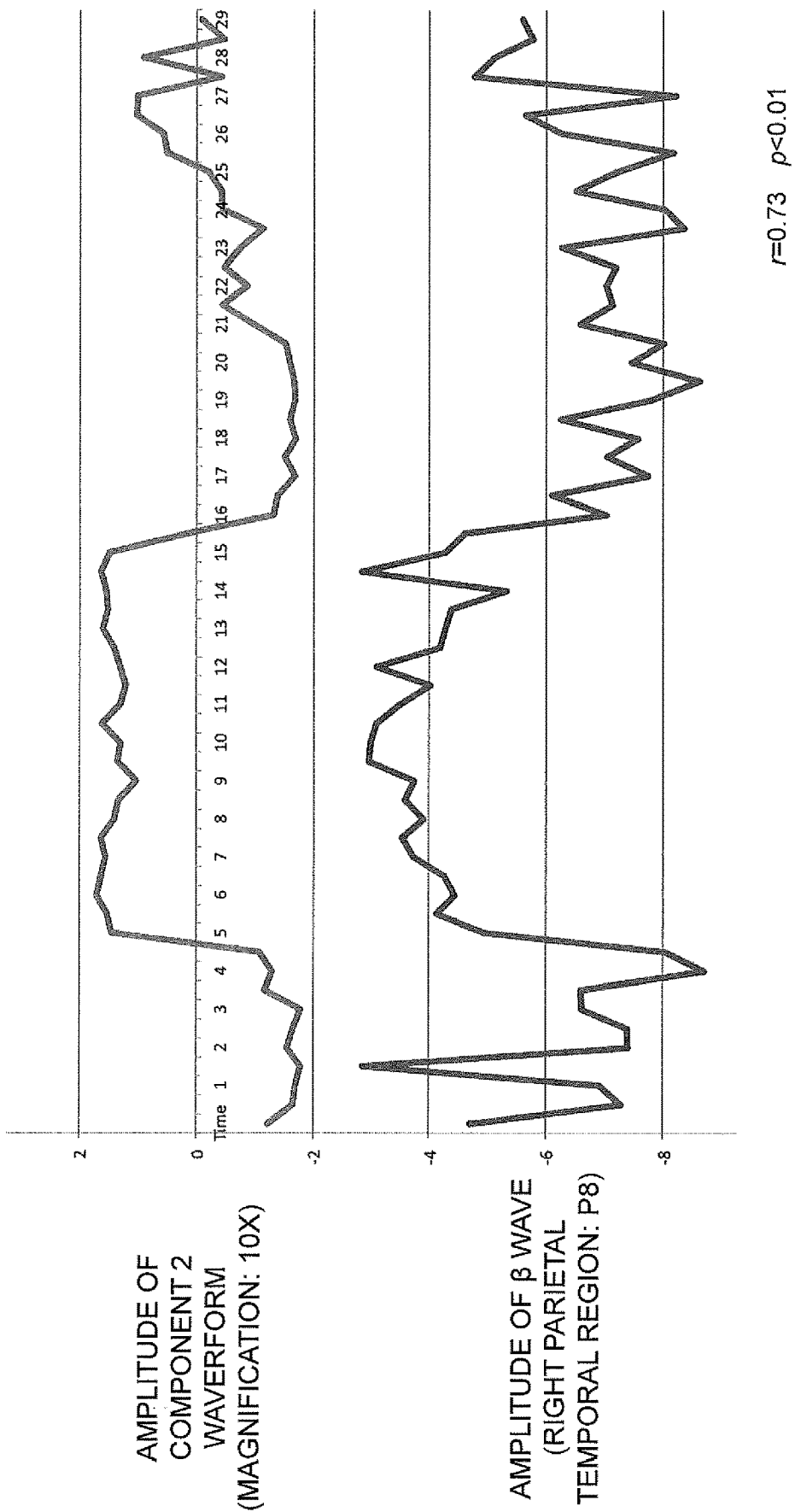
FIG. 7 is a chart illustrating a component waveform based on photographic image data of the facial surface, and the amplitude of the β wave of the measured brain waves.
Figure 8:
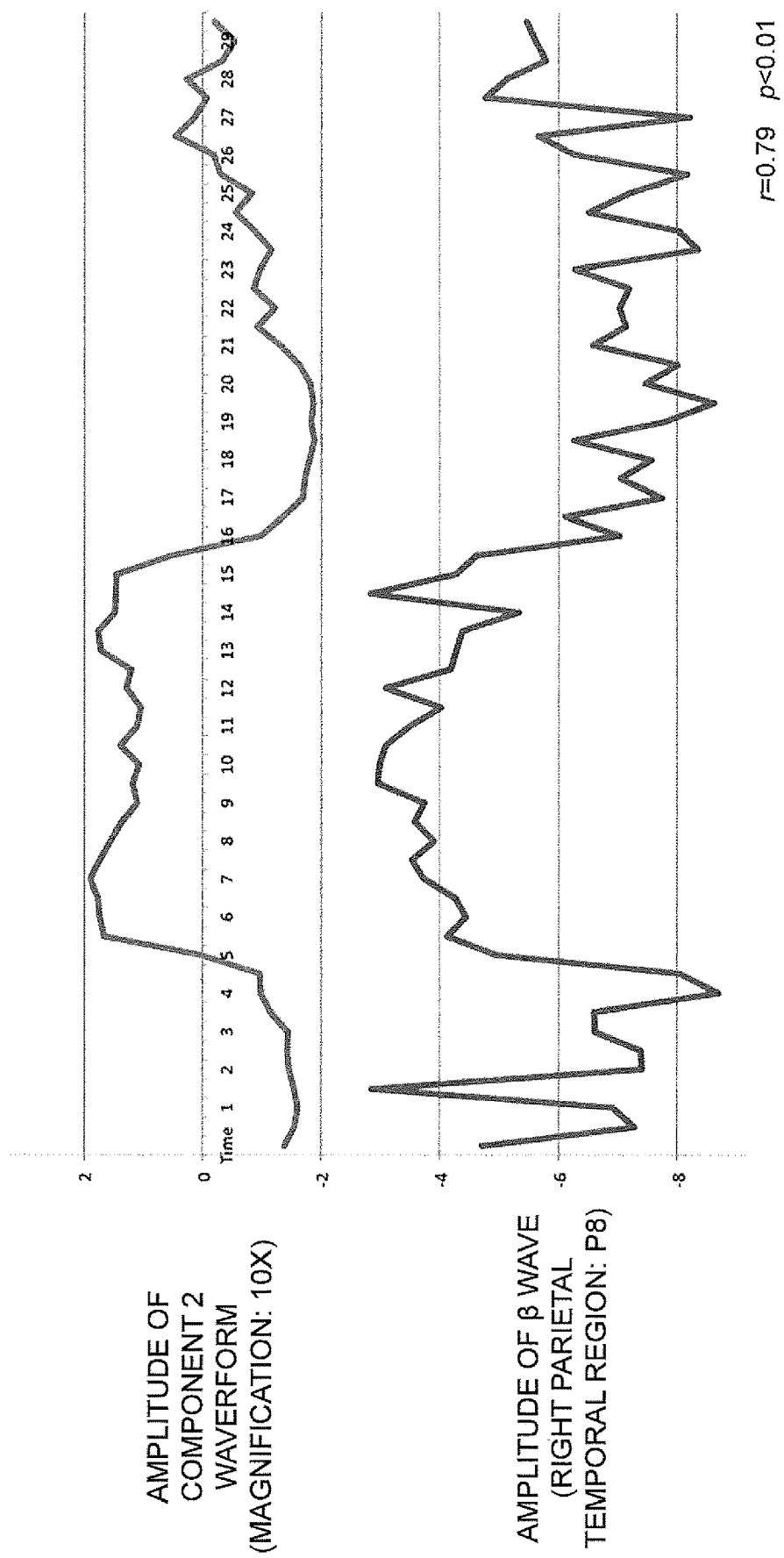
FIG. 8 is a chart illustrating a component waveform based on facial skin temperature data and the amplitude of the β wave of the measured brain waves.
Figure 9:
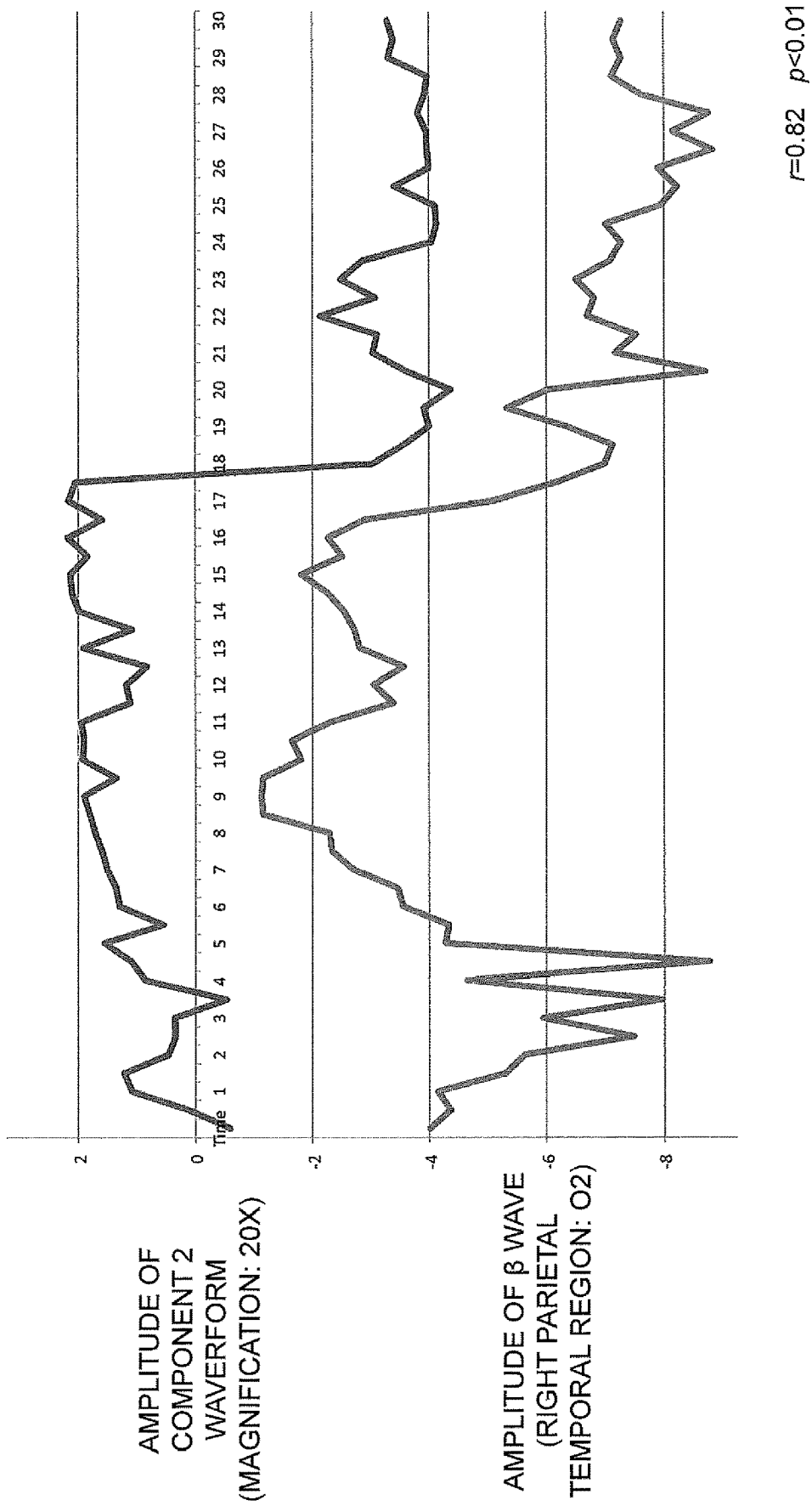
FIG. 9 is a chart illustrating a component waveform based on photographic image data of the facial surface, and the amplitude of the β wave of the measured brain waves.
Figure 10:
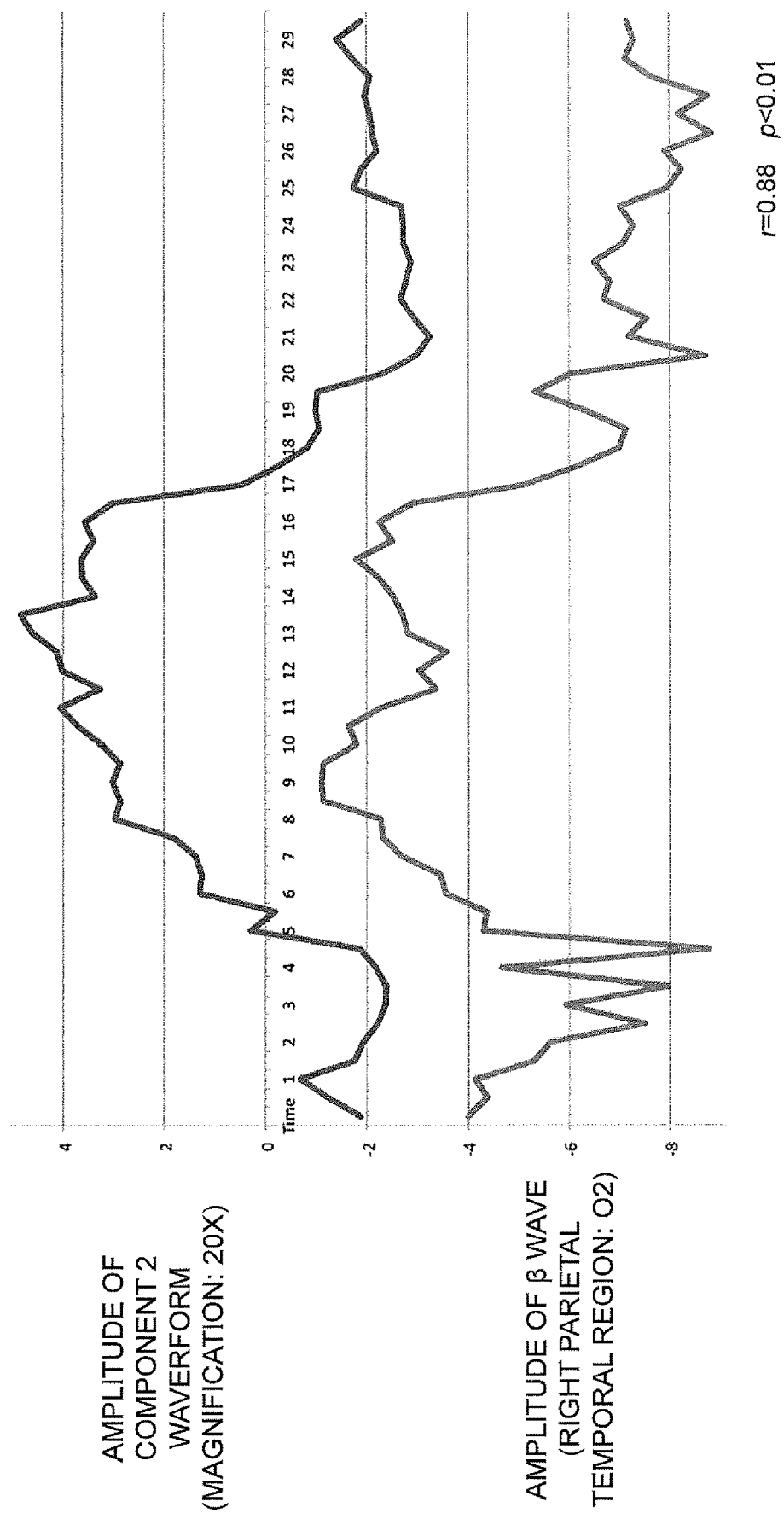
FIG. 10 is a chart illustrating a component waveform based on facial skin temperature data, and the amplitude of the β wave of the measured brain waves.
Figure 11:
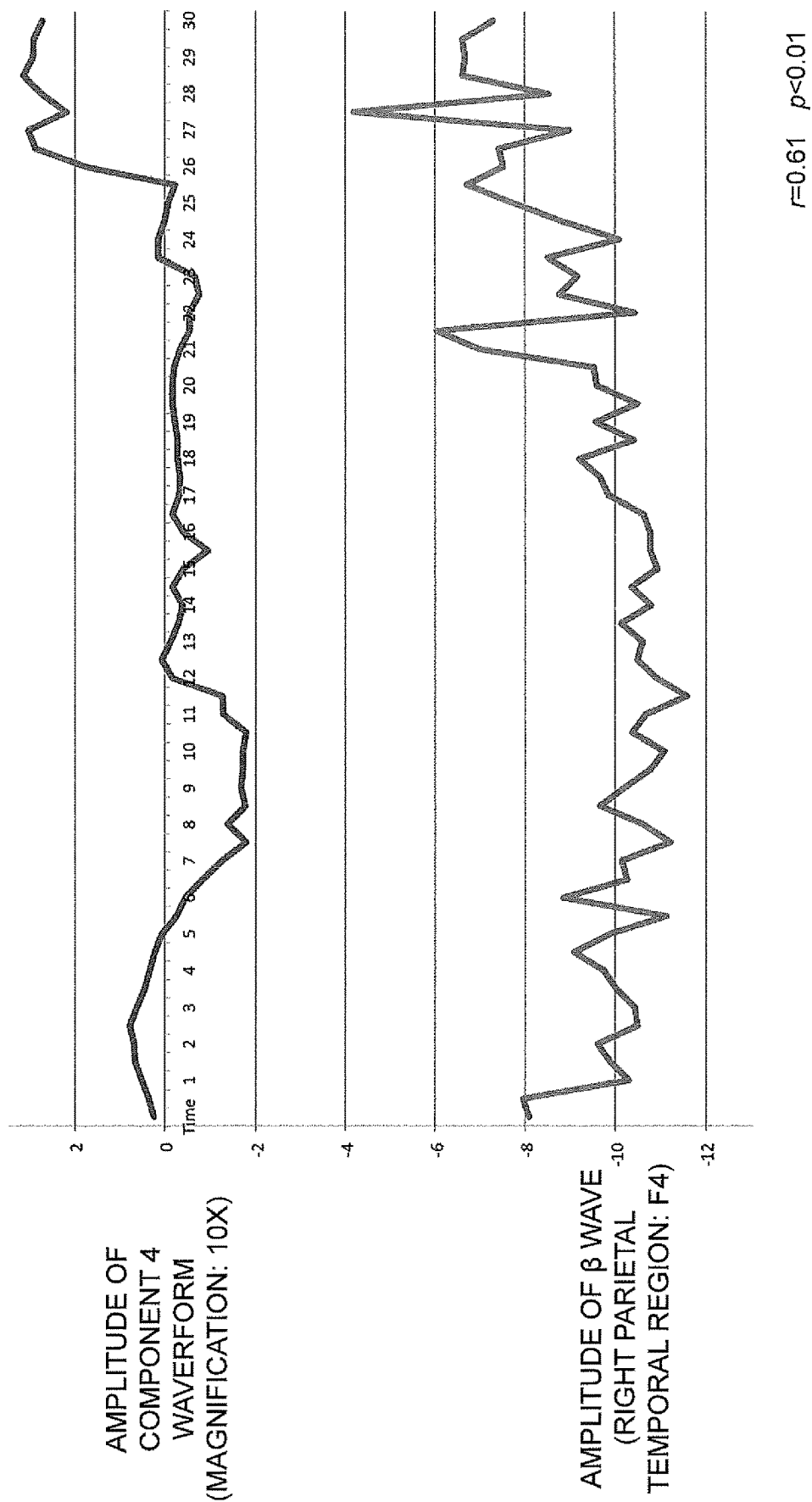
FIG. 11 is a chart illustrating a component waveform based on photographic image data of the facial surface, and the amplitude of the β wave of the measured brain waves.
Figure 12:
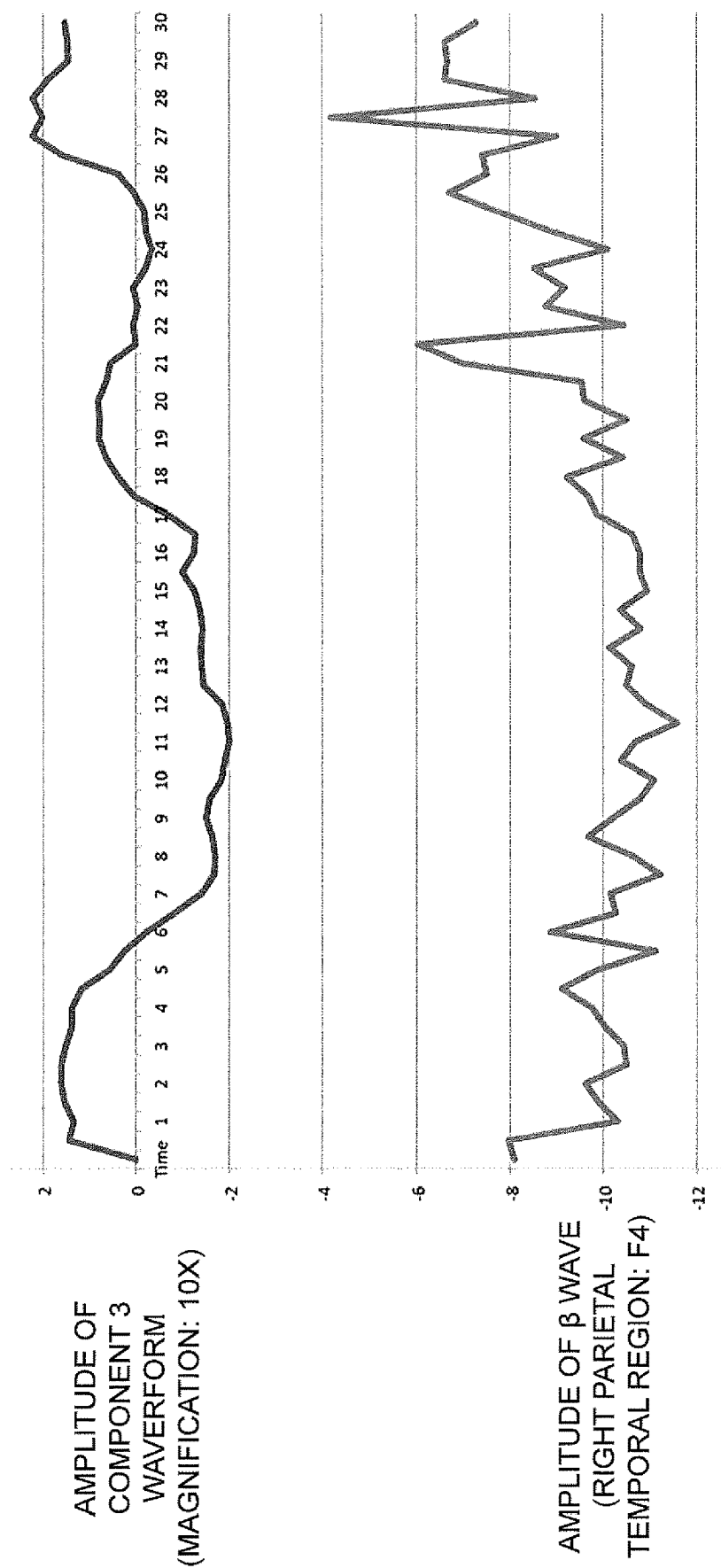
FIG. 12 is a chart illustrating a component waveform based on facial skin temperature data, and the amplitude of the β wave of the measured brain waves.
Figure 13:
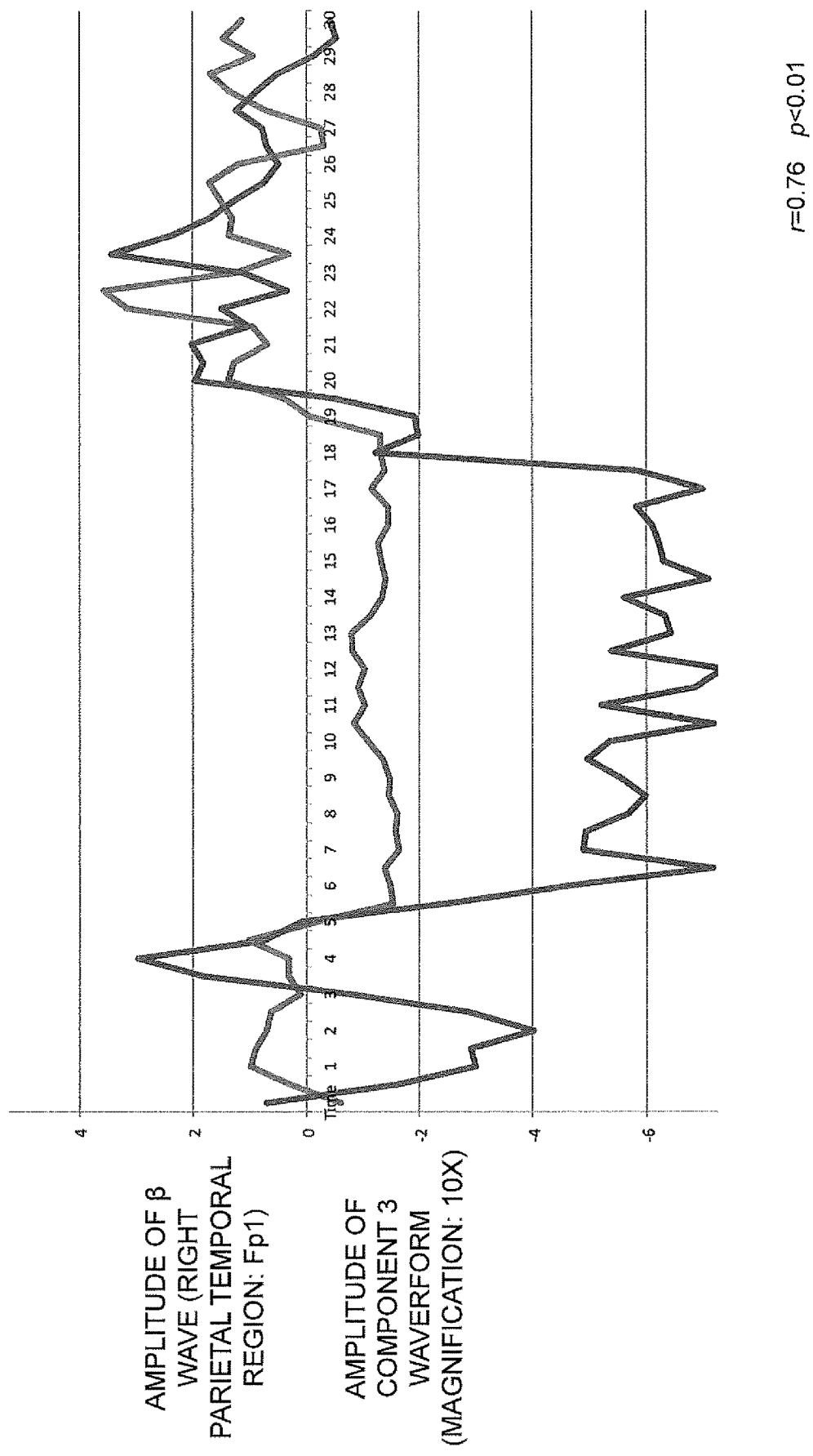
FIG. 13 is a chart illustrating a component waveform based on photographic image data of the facial surface, and the amplitude of the β wave of the measured brain waves.
Figure 14:
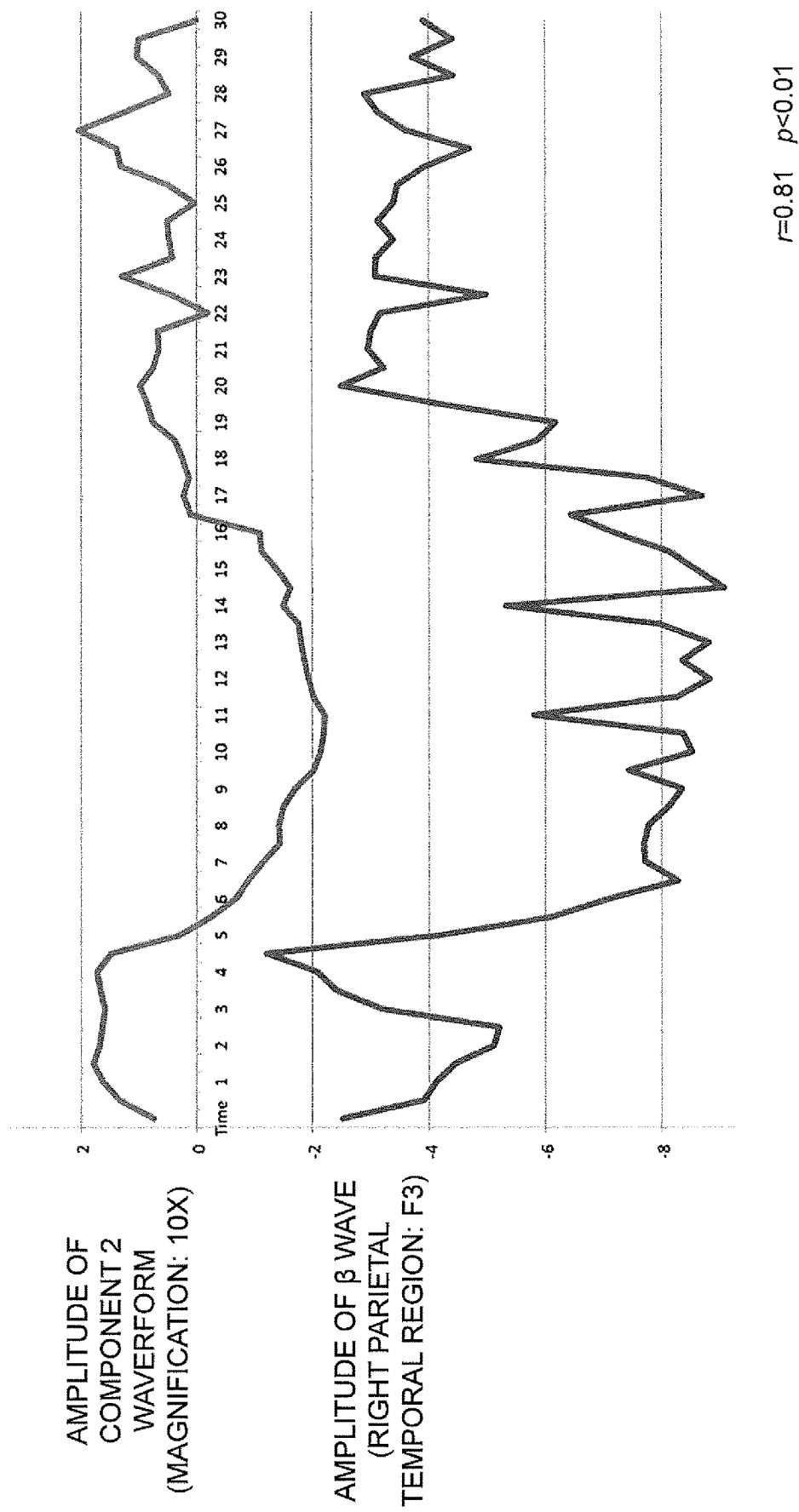
FIG. 14 is a chart illustrating a component waveform based on facial skin temperature data, and the amplitude of the β wave of the measured brain waves.
Figure 15:
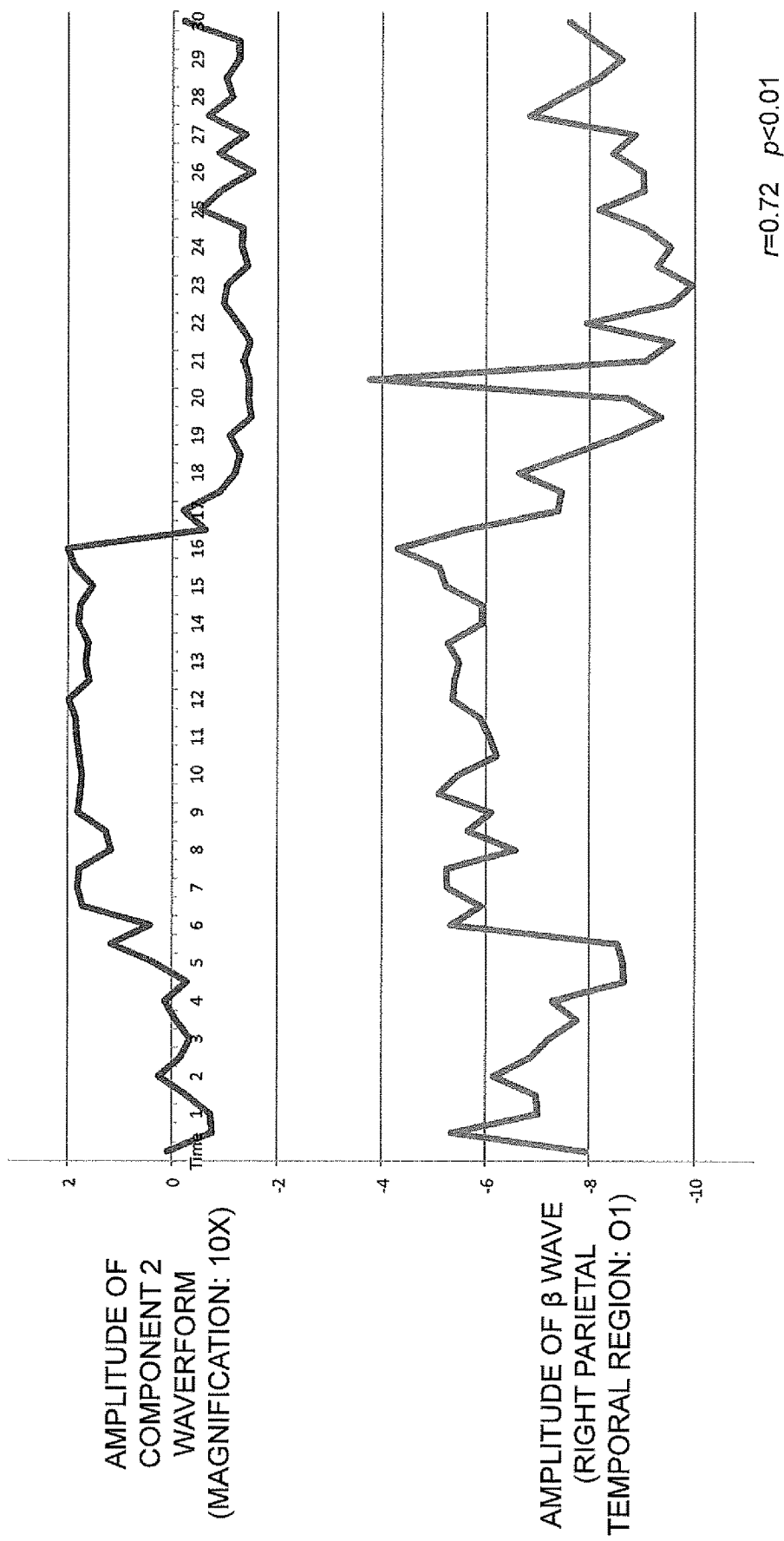
FIG. 15 is a chart illustrating a component waveform based on photographic image data of the facial surface, and the amplitude of the β wave of the measured brain waves.
Figure 16:
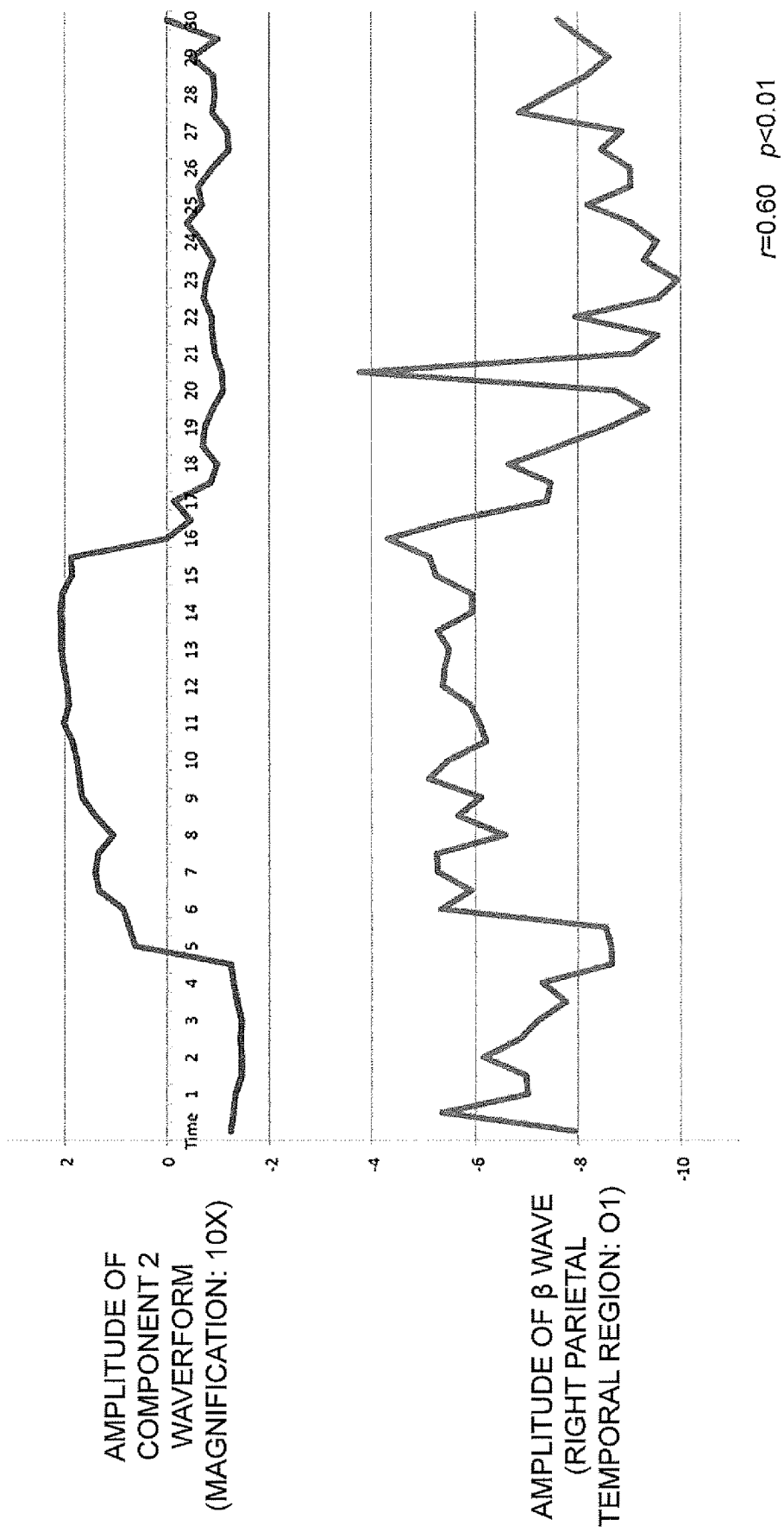
FIG. 16 is a chart illustrating a component waveform based on facial skin temperature data, and the amplitude of the β wave of the measured brain waves.
Figure 17:
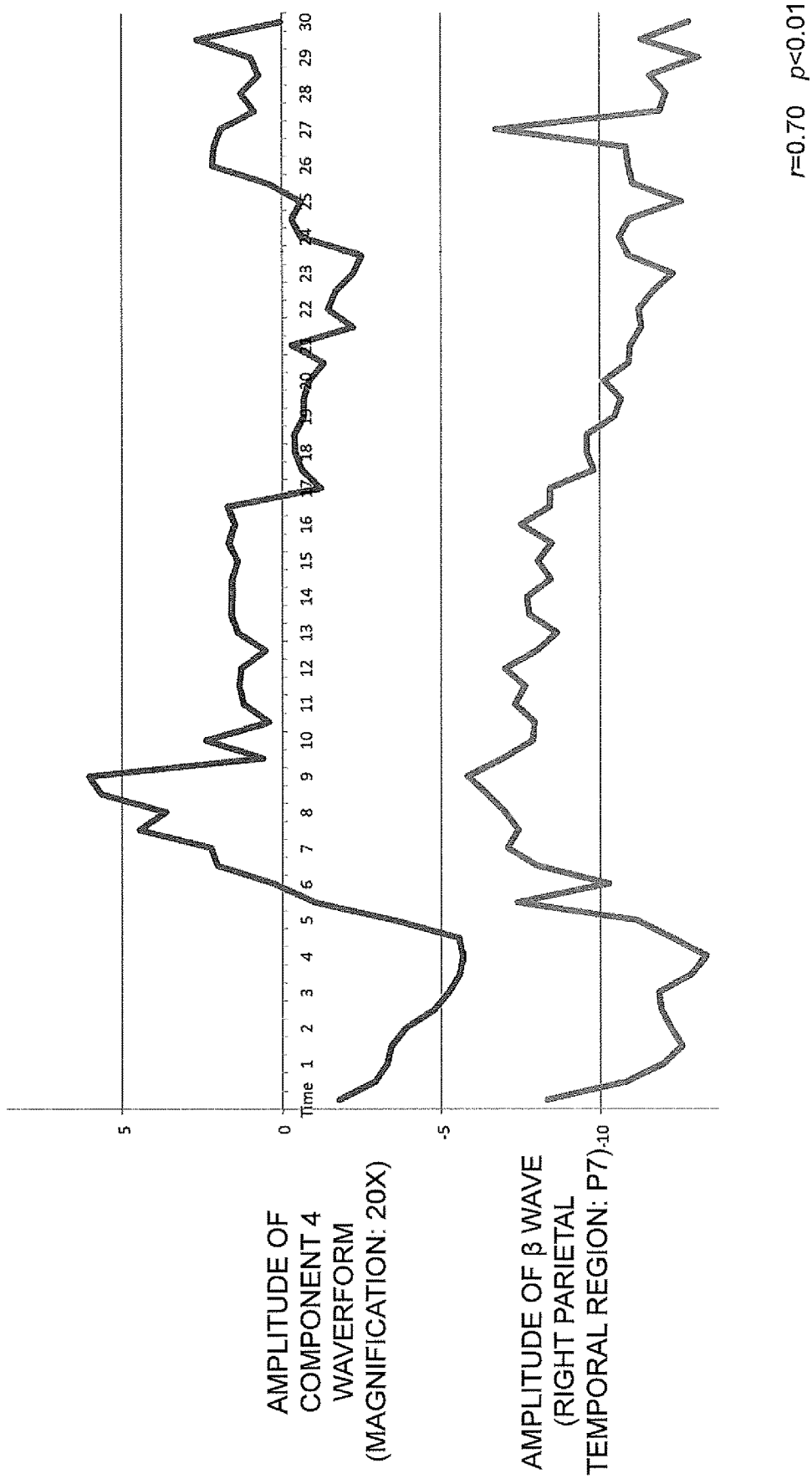
FIG. 17 is a chart illustrating a component waveform based on photographic image data of the facial surface, and the amplitude of the β wave of the measured brain waves.
Figure 18:
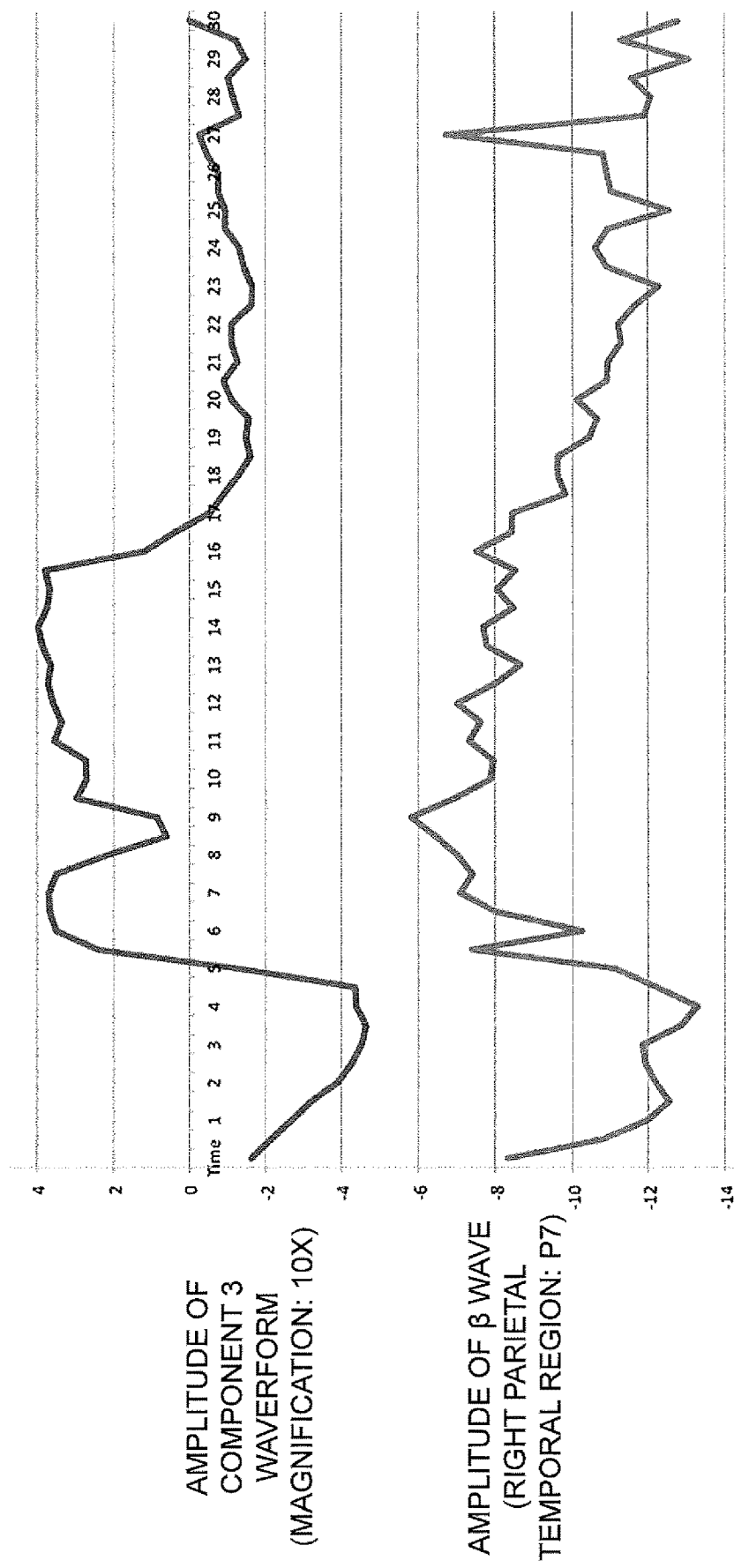
FIG. 18 is a chart illustrating a component waveform based on facial skin temperature data, and the amplitude of the β wave of the measured brain waves.

FIGS. 7 to 18 illustrate portions of the results of comparing-analyzing component waveform diagrams based on the photographic image data of the facial surface (blood circulation volume data) or facial skin temperature data, and the waveform diagrams of the β wave of the measured brain waves. FIG. 7 illustrates the amplitude of the component waveform of the component 2 based on the photographic image data of the subject 1, and the amplitude of the β wave of the measured brain waves of the subject 1. FIG. 8 illustrates the amplitude of the component waveform of the component 2 based on the facial skin temperature data of the subject 1, and the amplitude of the β wave of the measured brain waves of the subject 1. FIG. 9 illustrates the amplitude of the component waveform of the component 2 based on the photographic image data of a subject 2, and the amplitude of the β wave of the measured brain waves of the subject 2. FIG. 10 illustrates the amplitude of the component waveform of the component 2 based on the facial skin temperature data of the subject 2, and the amplitude of the β wave of the measured brain waves of the subject 2. FIG. 11 illustrates the amplitude of the component waveform of a component 4 based on the photographic image data of a subject 3, and the amplitude of the β wave of the measured brain waves of the subject 3. FIG. 12 illustrates the amplitude of the component waveform of the component 3 based on the facial skin temperature data of the subject 3, and the amplitude of the β wave of the measured brain waves of the subject 3. FIG. 13 illustrates the amplitude of the component waveform of the component 3 based on the photographic image data of a subject 4, and the amplitude of the β wave of the measured brain waves of the subject 4. FIG. 14 illustrates the amplitude of the component waveform of the component 2 based on the facial skin temperature data of the subject 4, and the amplitude of the β wave of the measured brain waves of the subject 4. FIG. 15 illustrates the amplitude of the component waveform of the component 2 based on the photographic image data of the subject 5, and the amplitude of the β wave of the measured brain waves of the subject 5. FIG. 16 illustrates the amplitude of the component waveform of the component 2 based on the facial skin temperature data of the subject 5, and the amplitude of the β wave of the measured brain waves of the subject 5. FIG. 17 illustrates the amplitude of the component waveform of a component 4 based on the photographic image data of a subject 6, and the amplitude of the β wave of the measured brain waves of the subject 6. FIG. 18 illustrates the amplitude of the component waveform of the component 3 based on the facial skin temperature data of the subject 6, and the amplitude of the β wave of the measured brain waves of the subject 6.

As illustrated in FIGS. 7 to 18, from the results of the component waveforms and brain wave analyses, correlation was found between the facial skin temperature and the facial blood circulation volume. In each of the analyses based on the facial skin temperature data and the facial blood circulation volume data, significant correlation was found between the amplitude of each component waveform and the amplitude of the β wave measured by the electrodes attached to the top or back of the head.

Table 2 shows the results of analyzing the photographic image data of the facial surface of each subject.

TABLE 2

| Subject | Correlation in Blood Circulation Volume Data | | Correlation in Relative Conversion Blood Circulation Volume Data | |
| --- | --- | --- | --- | --- |
| | Component waveform | Blood circulation volume distribution | Component waveform | Blood circulation volume distribution |
| Subject 1 | Component 2 | 0.72 | Component 1 | 0.59 |
| | | | Component 2 | 0.85 |
| Subject 2 | Component 1 | 0.82 | Component 1 | 0.62 |
| | Component 2 | 0.82 | Component 2 | 0.60 |
| Subject 3 | Component 2 | 0.33 | Component 2 | 0.45 |
| | | | Component 3 | 0.56 |
| | Component 3 | 0.31 | Component 4 | 0.56 |
| Subject 4 | Component 1 | 0.57 | Component 1 | 0.66 |
| | Component 3 | 0.71 | Component 3 | 0.65 |
| Subject 5 | Component 1 | 0.56 | Component 1 | 0.51 |
| | Component 2 | 0.72 | Component 2 | 0.83 |
| Subject 6 | Component 2 | 0.38 | Component 2 | 0.45 |
| | | | Component 3 | 0.51 |
| | Component 4 | 0.68 | Component 5 | 0.36 |

As shown in Table 2, from the results obtained by analyzing the photographic image data of the facial surface described above, significant correlation was found between human brain activity and the components 1, 2, 3, 4, and 5 of the plurality of components obtained by decomposing the time-series blood circulation volume data based on the photographic image data of the facial surface by singular value decomposition. Note that, in this case, the components found to have significant correlation based on the blood circulation volume data and significant correlation based on the relative conversion blood circulation volume data were determined to have the significant correlation with human brain activity and, in addition, the components that did not have significant correlation based on the blood circulation volume data but did have significant correlation based on the relative conversion blood circulation volume data were also determined to have the significant correlation with human brain activity. Table 3 shows the results of the control test.

TABLE 3

| Components having correlation with brain resting time/brain activated time | Component 1, Component 2 |
|---|---|
| Components having correlation with movement distance of face | Component 1, Component 3, Component 4 |
| Components having correlation with number of keyboard inputs | Component 8 |

As shown in Table 3, in the control test, when the subject moved while the photographic image data of the facial surface was being acquired, some of the components were found to have significant correlation between the amplitude of the component waveform thereof and each of the brain resting time and the brain activated time. Among these components, the component 2 was not found to have significant correlation with movement distance or the number of keyboard inputs. As such, it was confirmed that, among the plurality of components that were obtained by conducting the singular value decomposition on the blood circulation volume data based on the RGB data acquired from the photographic image data of the facial surface, a component having significant correlation with brain activity could be influenced by the movement of the subject while acquiring the time-series photographic image data of the facial surface, but this influence was much smaller than the influence resulting from the brain activity (the influence resulting from the activation or resting of the brain).

Based on these results, the present inventors made the following findings.

The blood circulation volume data, obtained from the RGB data of the facial surface based on time-series photographic image data of the facial surface acquired from the subjects, was decomposed into the plurality of components by singular value decomposition. As a result of analyzing each of the decomposed components, it was found that the components 1, 2, 3, 4, and 5 of the plurality of components are components that are related to brain activity. Specifically, it was found that it is possible to identify a component indicating an RGB change in the facial surface that reflects brain activity from the plurality of components, by decomposing the blood circulation volume data, which was obtained from the RGB data of the facial surface based on the time-series photographic image data of the facial surface into the plurality of components, extracting components having correlation with the activation/resting of the brain from the decomposed plurality of components, and analyzing the extracted components. Thus, the present inventors found that it is possible to estimate brain activity on the basis of time-series photographic image data of a human facial surface.

(4) Brain Activity Visualization Device

Next, brain activity visualization devices 10, 110 according to an embodiment of the present disclosure will be described. The brain activity visualization devices 10, 110 were conceived by the inventor on the basis of the findings described above. The brain activity visualization devices according to the present disclosure should not be construed as being limited to the following embodiments, and various types of modifications may be made without departing from the spirit or scope of the general inventive concept of the present disclosure.

The brain activity visualization devices 10, 110 according to the embodiment of the present disclosure include brain activity estimation means 30 that estimate brain activity on the basis of facial skin temperature data, and/or brain activity estimation means 130 that estimate brain activity on the basis of photographic image data of the facial surface. Before describing the brain activity visualization devices 10, 110 according to the embodiment of the present disclosure, each of the brain activity estimation means 30, 130 will be described.

Figure 19:
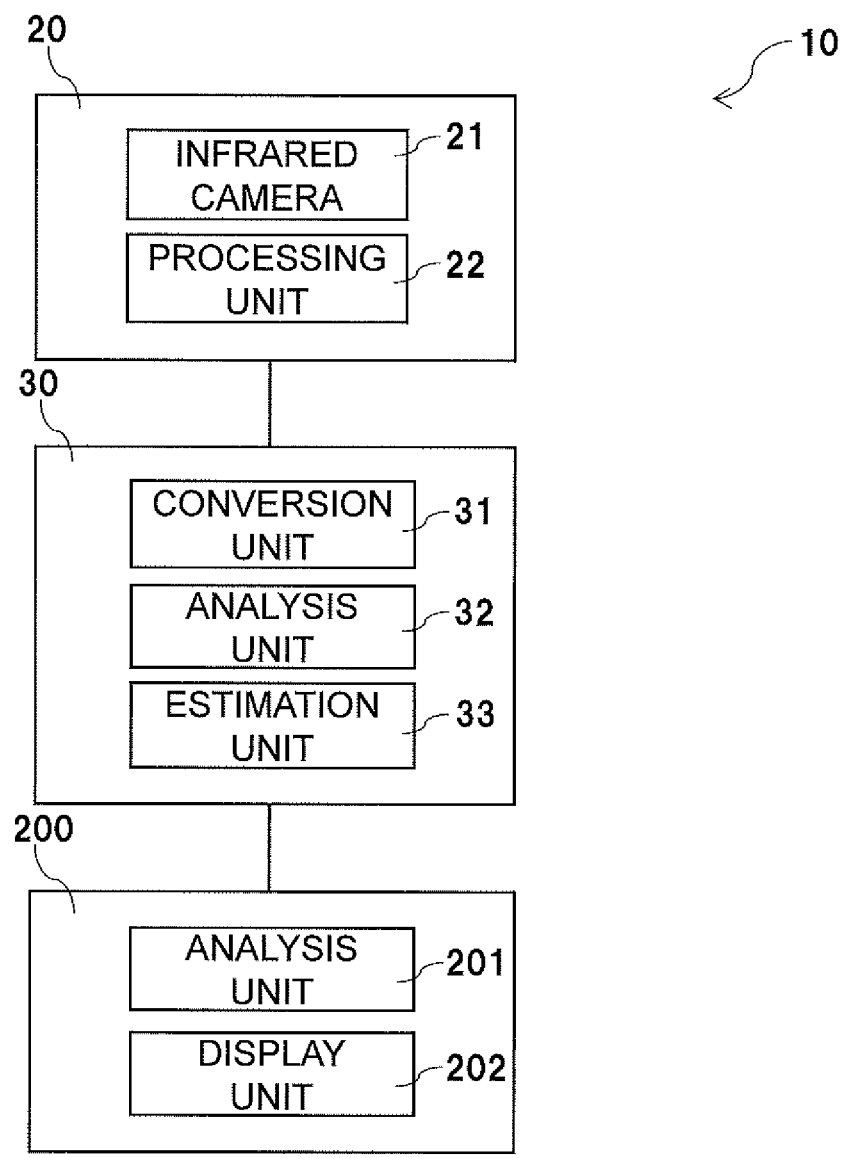
FIG. 19 is a schematic drawing of a brain activity visualization device according to an embodiment of the present disclosure.
Figure 20:
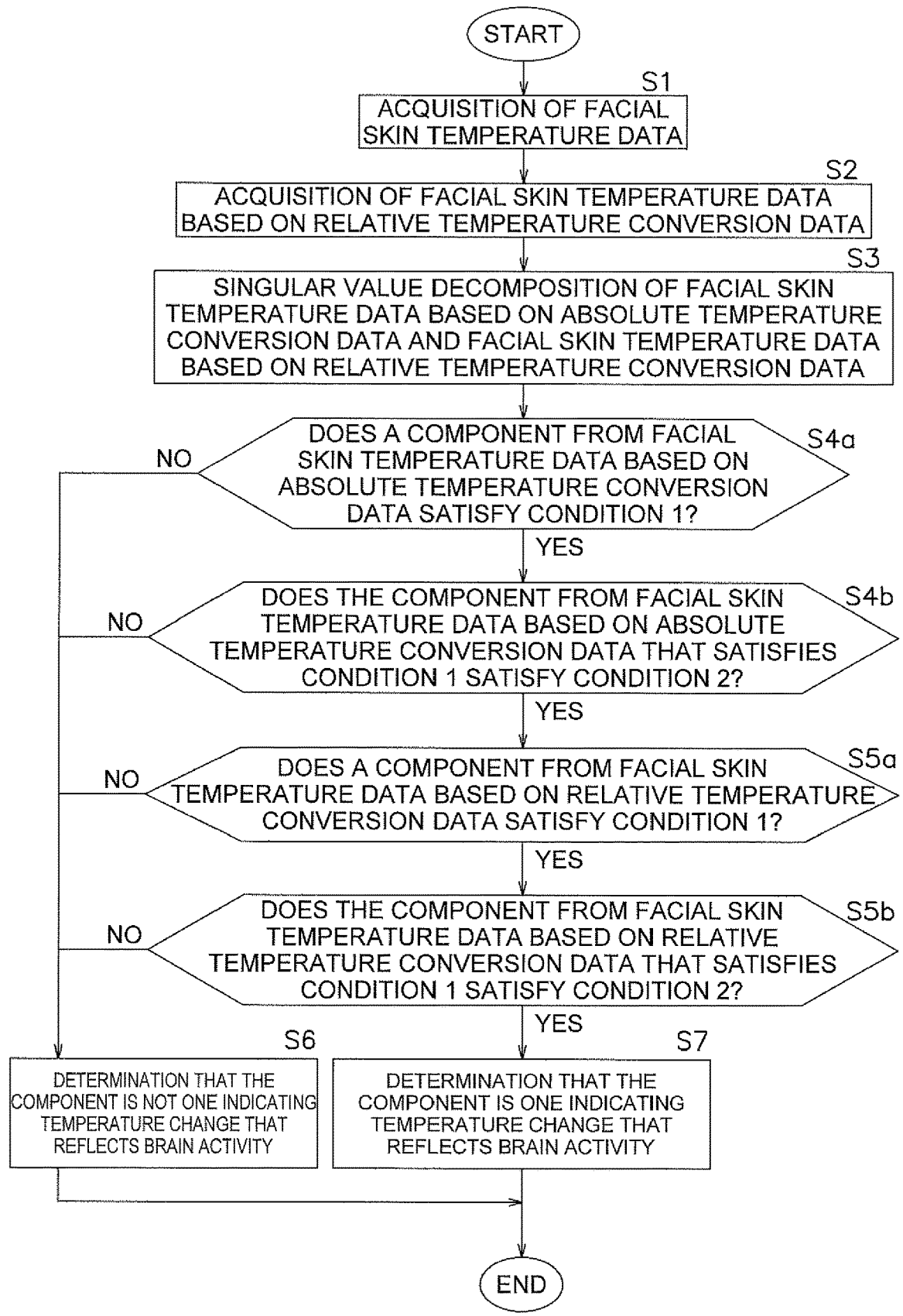
FIG. 20 is a flowchart showing an example of the flow of processing conducted in the brain activity visualization device to identify a component indicating a change in skin temperature that reflects brain function.

(4-1) Brain Activity Estimation Means 30 that Estimate Brain Activity on the Basis of Facial Skin Temperature Data FIG. 19 is a schematic drawing of the brain activity visualization device 10 according to the embodiment of the present disclosure. FIG. 20 is a flowchart showing the flow of processing conducted in the brain activity visualization device 10 to identify a component indicating a change in skin temperature that reflects brain function.

The brain activity estimation means 30 of the brain activity visualization device 10 estimate the brain activity of an individual (subject) from the facial skin temperature of the individual. As illustrated in FIG. 19, the brain activity visualization device 10 includes facial skin temperature acquisition means 20, the brain activity estimation means 30, and state visualization means 200.

The facial skin temperature acquisition means 20 detect the skin temperature of at least a portion of the facial surface of the individual, and chronologically acquire facial skin temperature data including detected temperature data and position data of the detection site (step S1). Note that, in this case, the facial skin temperature acquisition means 20 is an infrared thermography device and includes an infrared camera 21 and a processing unit 22 as illustrated in FIG. 19. The infrared camera 21 is configured to detect infrared radiant energy emitted from the facial surface of the individual. Moreover, in this case, the infrared camera 21 is configured to detect infrared radiant energy emitted from the entire facial surface of the individual. The processing unit 22 converts the infrared radiant energy detected by the infrared camera 21 to temperatures to create temperature data. The processing unit 22 generates a temperature distribution diagram of the facial skin temperature of the entire facial surface, for which the sites where the infrared radiant energy was detected are used as the position data (coordinate data). The processing unit 22 processes the generated temperature distribution diagram as facial skin temperature data based on temperature conversion data. The processing unit 22 has a storage unit (not illustrated in the drawings) and the facial skin temperature data based on temperature conversion data is stored in this storage unit.

An example is described in which the temperature distribution diagram of the facial skin temperature of the whole facial surface is generated in the processing unit 22, but the present disclosure is not limited thereto. For example, a configuration is possible in which a temperature distribution diagram of facial skin temperature including at least the forehead and/or the area around the paranasal sinuses is generated and used as the facial skin temperature data based on temperature conversion data.

Additionally, in this case, a brain function activation task is given to the individual for a set period of time while the facial skin temperature acquisition means 20 are acquiring the facial skin temperature data based on temperature conversion data. That is, the facial skin temperature data based on temperature conversion data, acquired by the facial skin temperature acquisition means 20, contains data for a period in which the brain function activation task was being given to the individual. Note that the brain function activation task given to the individual is not particularly limited provided that the task is presumed to place the brain in an activated state, and the content thereof may be appropriately determined in accordance with the purpose of use of the brain activity visualization device 10.

The brain activity estimation means 30 estimate human brain activity on the basis of facial skin temperature data based on the temperature conversion data acquired by the facial skin temperature acquisition means 20. Specifically, the brain activity estimation means 30 include a conversion unit 31, an analysis unit 32, and an estimation unit 33 as illustrated in FIG. 19.

The conversion unit 31 converts the temperature data included in the facial skin temperature data based on temperature conversion data to relative temperature data, and generates facial skin temperature data based on the converted relative temperature data, that is, facial skin temperature data based on relative temperature conversion data (step S2). Specifically, the conversion unit 31 uses, as a reference, an average of the temperature data included in the facial skin temperature data based on temperature conversion data for every predetermined time period (e.g. 30 seconds), and converts the temperature data to relative temperature data. Then, the conversion unit 31 uses the converted relative temperature data and the position data to generate the facial skin temperature data based on relative temperature conversion data.

The analysis unit 32 decomposes each of the time-series facial skin temperature data based on temperature conversion data and the facial skin temperature data based on relative temperature conversion data into a plurality of components by singular value decomposition, principal component analysis, or independent component analysis (step S3). Here, the analysis unit 32 subjects each of the acquired facial skin temperature data based on temperature conversion data and the facial skin temperature data based on relative temperature conversion data to singular value decomposition in which the SVD of MATLAB (registered trademark) is used as the analysis tool. In the singular value decomposition, for each of the chronologically acquired facial skin temperature data based on temperature conversion data and the facial skin temperature data based on relative temperature conversion data, the factor is set to time data per predetermined time period (e.g. 30 seconds), and the measure is set to the facial skin temperature data based on temperature conversion data and the facial skin temperature data based on relative temperature conversion data in each time period. Then, the facial skin temperature data based on temperature conversion data and the facial skin temperature data based on relative temperature conversion data are each decomposed into a plurality of components by singular value decomposition. Thereafter, the analysis unit 32 calculates a time distribution, a space distribution, and a singular value representing the magnitude of each component.

Additionally, the analysis unit 32 determines whether or not each component satisfies a first condition and a second condition in order to identify a component, from the plurality of components decomposed by singular value decomposition, indicating a change in skin temperature that reflects brain activity (step S4*a*, step S4*b*, step S5*a*, and step S5*b*). Note that, in this case, the analysis unit 32 first determines whether or not each component from the facial skin temperature data based on temperature conversion data satisfies the first condition (step S4*a*). Then, for components from the facial skin temperature data based on temperature conversion data determined to satisfy the first condition in step S4*a*, the analysis unit 32 determines whether or not those components satisfy the second condition (step S4*b*). Then, the analysis unit 32 determines whether or not each component from the facial skin temperature data based on relative temperature conversion data, matching the components determined to satisfy the first condition and the second condition in step S4*a* and step S4*b*, satisfies the first condition (step S5*a*). Then, the analysis unit 32 determines whether or not the components from the facial skin temperature data based on relative temperature conversion data, which is determined to satisfy the first condition in step S5*a* satisfy the second condition (step S5*b*). However, the order of determination in the analysis unit 32 is not limited thereto and, for example a configuration is possible in which it is determined whether or not the components from the facial skin temperature data based on temperature conversion data and the components from the facial skin temperature data based on relative temperature conversion data satisfy the first condition and the second condition respectively, and the components for which the determination results match are ultimately extracted.

The first condition is that the amplitude of the component waveform of the component decomposed by singular value decomposition has correlation with changes at brain resting time and brain activated time. The analysis unit 32 extracts, from the plurality of components, components satisfying the first condition as determination components. Note that, the brain function activation task is given to the individual for a set period of time while the facial skin temperature data based on temperature conversion data is being acquired. The brain resting time is defined as the period in which the brain function activation task is not being given to the individual, and the brain activated time is defined as the period in which the brain function activation task is being given to the individual. Here, the analysis unit 32 conducts a comparative analysis of the component waveform of each component against the periods in which the brain function activation task is and is not being given. Using the results of this comparative analysis based on the component waveform data, the analysis unit 32 evaluates whether or not there is correlation between the component waveform of each component and each of the brain resting time and the brain activated time. Then, the analysis unit 32 extracts, from the plurality of components, components evaluated as having correlation as a determination component that satisfies the first condition. Meanwhile, the analysis unit 32 determines that, among the plurality of components, a component evaluated as not having correlation is the component that does not satisfy the first condition and is not the component indicating a temperature change that reflects human brain activity (step S6).

In this case, the brain function activation task is given to the individual for a set period of time while acquiring the facial skin temperature data based on temperature conversion data, and the analysis unit 32 extracts the determination components based thereon. However, the content of the first condition, that is, the means of extracting the determination component by the analysis unit 32, is not limited thereto. For example, when the components, among the plurality of components, indicating a component waveform that has correlation with the brain resting time and the brain activated time are already identified by previous experiments or the like, the analysis unit 32 may extract these identified components from the plurality of components as the determination components. Additionally, with this brain activity visualization device, in cases where human behavior, which is known to be related to the activation/resting of the brain, such as eye movement and blinking are detected, the analysis unit 32 may extract the determination components from the plurality of components by comparing and analyzing the detection results against the component waveform of each component and conducting an evaluation. Note that the criterion for the analysis unit 32 to determine whether or not the first condition is satisfied is appropriately decided by simulations, experiments, theoretical calculations, or the like, in accordance with the purpose of use of the brain activity visualization device 10 or the like.

The second condition is that there is a temperature change at the predetermined site on the human facial surface in the extracted determination components. The analysis unit 32 determines that, among the determination components, the components that satisfy the second condition have a high potential of being related to human brain activity, and extracts these as candidate components. That is, the analysis unit 32 determines whether or not the determination components are related to human brain activity on the basis of the presence/absence of a temperature change at the predetermined site on a human facial surface. Specifically, the analysis unit 32 determines whether or not temperature change has occurred at the forehead and/or the area around the paranasal sinuses on the basis of the temperature distribution data of the extracted determination components. When a temperature change has occurred, the analysis unit 32 determines that there is a high possibility that the determination component satisfies the second condition and is related to human brain activity, and extracts that determination component as a candidate component. Meanwhile, when a temperature change has not occurred at the forehead or the area around the paranasal sinuses, the analysis unit 32 determines that the determination component does not satisfy the second condition and is not a component indicating a skin temperature change that reflects human brain activity (step S6). Note that the criterion for the analysis unit 32 to determine whether or not the second condition is satisfied is appropriately decided by simulations, experiments, theoretical calculations, or the like, in accordance with the purpose of use of the brain activity visualization device 10.

Then, the analysis unit 32 identifies the component which is determined to satisfy the second condition in step S5b, as a component indicating a change in skin temperature that reflects brain activity (step S7). That is, the component identified in step S7 as the component indicating a change in skin temperature that reflects brain activity is a component that is present in both the candidate components extracted by decomposing and analyzing the facial skin temperature data based on temperature conversion data by singular value decomposition and the candidate components extracted by decomposing and analyzing the facial skin temperature data based on relative temperature conversion data by singular value decomposition. Note that, the candidate components for which both analyses do not match are determined not to be components indicating a change in skin temperature that reflects brain activity in step S6.

The estimation unit 33 estimates human brain activity on the basis of the component identified by the analysis unit 32 as a component indicating a change in skin temperature that reflects human brain activity. Specifically, the estimation unit 33 estimates an amount of brain activity when acquiring the facial skin temperature data on the basis of the component waveform data of the component identified by the analysis unit 32.

(4-1-1) Modification Example 1A

The brain activity estimation means 30 described above includes the conversion unit 31, and the facial skin temperature data based on relative temperature conversion data is generated by the conversion unit 31. Moreover, the analysis unit 32 uses singular value decomposition to decompose, into a plurality of components, not only the facial skin temperature data based on temperature conversion data acquired by the facial skin temperature acquisition means 20, but also the facial skin temperature data based on relative temperature conversion data, which is from the temperature data that has been converted into relative temperature data. Then, the analysis unit 32 analyzes each of the components.

Instead of this, a configuration in which the brain activity estimation means 30 does not include the conversion unit 31 can be adopted. In this case, the processes for generating the facial skin temperature data based on relative temperature conversion data and analyzing the data from the facial skin temperature data based on relative temperature conversion data can be omitted.

However, in order to accurately identify the component related to human brain activity, it is preferable that the brain activity estimation means 30 include the conversion unit 31, as in the embodiment described above. Moreover, it is preferable that the analysis unit 32 conducts singular value decomposition to decompose, into a plurality of components, not only the facial skin temperature data based on temperature conversion data acquired by the facial skin temperature acquisition means 20, but also the facial skin temperature data based on relative temperature conversion data, which is from the temperature data that has been converted into relative temperature data; and analyzes each of the components.

(4-1-2) Modification Example 1B

The facial skin temperature acquisition means 20 described above is an infrared thermography device capable of acquiring temperature data in a state of non-contact with the subject.

However, the facial skin temperature acquisition means are not particularly limited to an infrared thermography device, provided that the facial skin temperature acquisition means are capable of detecting the skin temperature of at least a portion of the facial surface of the individual, and chronologically acquiring facial skin temperature data including detected temperature data and position data of the detection site.

For example, the facial skin temperature acquisition means may be a device that includes temperature sensors. Specifically, a configuration is possible in which the temperature sensors are applied to predetermined sites on the facial surface of the individual, and the time-series facial skin temperature data is acquired on the basis of temperature data detected by the temperature sensors and the position data of the sites where the temperature sensors are applied. Even in cases where the facial skin temperature data is acquired while the temperature sensors are in contact with the individual, namely the subject, there is no need to treat the temperature sensors prior to application, unlike a case in which electroencephalogram electrodes or the like are used. As a result, data can be acquired more easily compared to conventional detection methods such as electroencephalography, functional magnetic resonance imaging, and near infrared spectroscopy. As such, human brain activity can be easily estimated.

Figure 21:
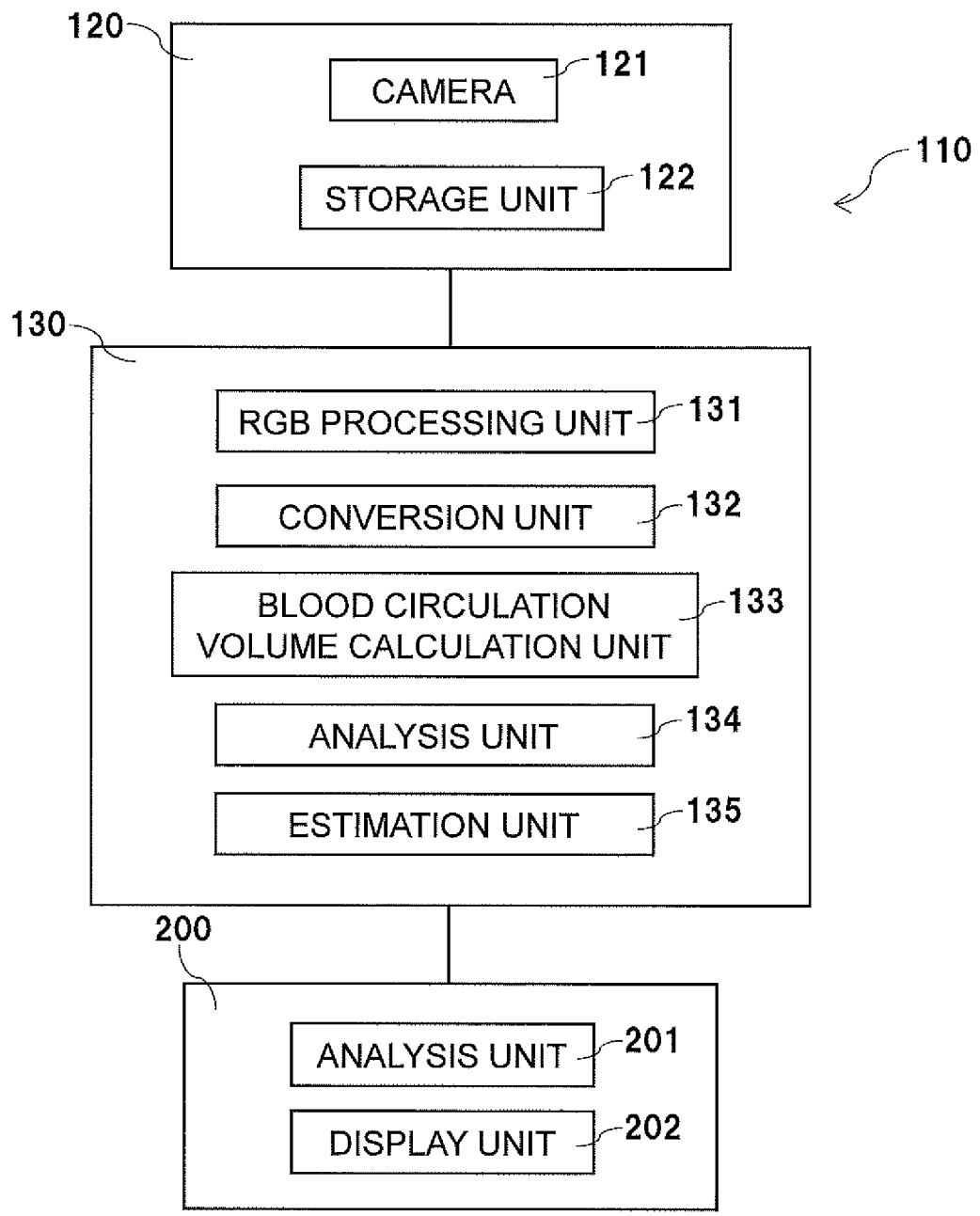
FIG. 21 is a schematic drawing of a brain activity visualization device according to an embodiment of the present disclosure.
Figure 22:
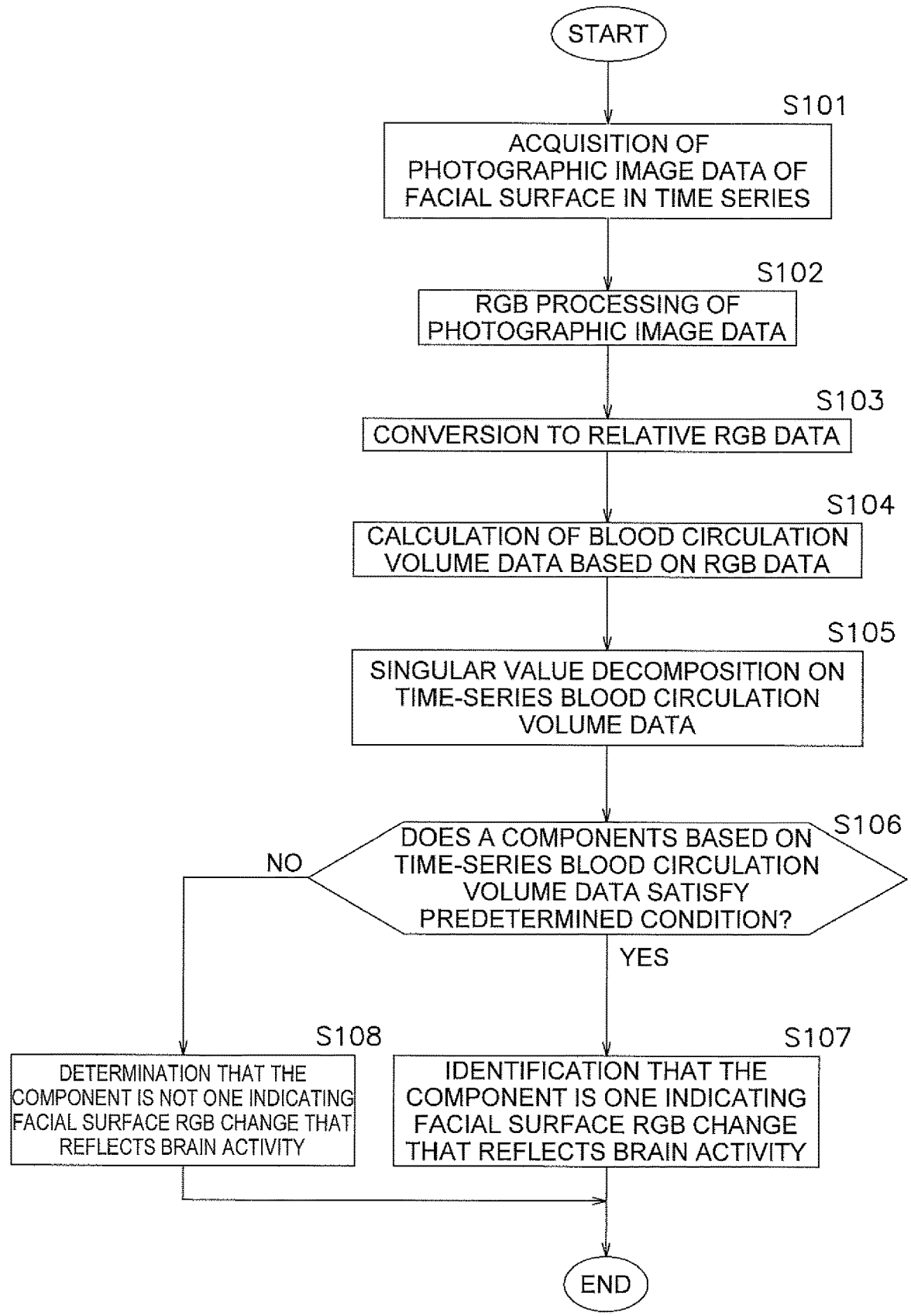
FIG. 22 is a flowchart showing an example of the flow of processing conducted in the brain activity visualization device to identify a component indicating an RGB change in the facial surface that reflects brain function.

(4-2) Brain Activity Estimation Means 130 that Estimate Brain Activity on the Basis of Photographic Image Data of Facial Surface FIG. 21 is a schematic drawing of the brain activity visualization device 110 according to the embodiment of the present disclosure. FIG. 22 is a flowchart showing an example of the flow of processing conducted in the brain activity visualization device 110 to identify a component indicating an RGB change in the facial surface that reflects brain function.

The brain activity estimation means 130 of the brain activity visualization device 110 estimate the brain activity of an individual (subject) from the photographic image data of the facial surface of the individual. As illustrated in FIG. 21, the brain activity visualization device 110 includes image data acquisition means 120, brain activity estimation means 130, and state visualization means 200.

The image data acquisition means 120 chronologically acquire photographic image data of at least a portion of the facial surface of the individual (step S101). Note that the image data acquisition means 120 are not particularly limited provided that they at least include an imaging device, and examples thereof include smartphones, tablets (e.g. iPad (registered trademark)), and other portable terminals with built in imaging devices. In this case, as illustrated in FIG. 21, the image data acquisition means 120 include a storage unit 122 and a camera 121 as the imaging device. The camera 121 is configured to chronologically acquire photographic image data of the facial surface of the individual. In this case, the camera 121 captures video of the entire facial surface of the individual and acquires the captured video data. The time-series photographic image data captured by the imaging device is stored in the storage unit 122. In this case, the video data acquired by the camera 121 is stored in the storage unit 122.

Note that, in this case, the camera 121 captures video of the entire facial surface, but the present disclosure is not limited thereto. For example, a configuration is possible in which the camera 121 captures video including images of at least the forehead and/or the area around the paranasal sinuses of the face.

Additionally, in this case, the brain function activation task is given to the individual for a set period of time while the image data acquisition means 120 are acquiring the time-series photographic image data of the facial surface. That is, the photographic image data acquired by the image data acquisition means 120 contains data for a period in which the brain function activation task is being given to the individual. Note that the brain function activation task given to the individual is not particularly limited provided that the task is presumed to place the brain in an activated state, and the content thereof may be appropriately determined in accordance with the purpose of use of the brain activity visualization device 110.

The brain activity estimation means 130 estimate human brain activity on the basis of the time-series photographic image data on the facial surface acquired by the image data acquisition means 120. Specifically, the brain activity estimation means 130 include an RGB processing unit 131, a conversion unit 132, a blood circulation volume calculation unit 133, an analysis unit 134, and an estimation unit 135 as illustrated in FIG. 21. Note that, in FIG. 21, a configuration is illustrated in which the brain activity estimation means 130 are a single device including the RGB processing unit 131, the conversion unit 132, the blood circulation volume calculation unit 133, the analysis unit 134, and the estimation unit 135. However, the present disclosure is not limited thereto and configurations are possible in which some or all of the RGB processing unit 131, the conversion unit 132, the blood circulation volume calculation unit 133, the analysis unit 134, and the estimation unit 135 are provided as independent devices. Additionally, in this case, facial blood circulation volume acquisition means are configured from the image data acquisition means 120, the RGB processing unit 131, the conversion unit 132, and the blood circulation volume calculation unit 133.

The RGB processing unit 131 performs RGB processing on the photographic image data acquired by the image data acquisition means 120 to decompose the photographic image data into three color components, namely an R component, a G component, and a B component (step S102). The RGB processing may be performed on the photographic image data of the entire facial surface but, in this case, the data of the forehead and/or area around the paranasal sinuses is extracted from the photographic image data and the RGB processing is performed on the extracted data in order to reduce computation load and noise.

The conversion unit 132 converts RGB data of the photographic image data obtained by the RGB processing to relative RGB data (step S103). Specifically, the conversion unit 132 uses, as a reference, an average of the RGB data obtained from the photographic image data for every predetermined time period (e.g. 30 seconds) to convert the RGB data to relative RGB data.

The blood circulation volume calculation unit 133 calculates time-series blood circulation volume data of the facial surface on the basis of the RGB data of the photographic image data obtained by the RGB processing (step S104).

The analysis unit 134 decomposes the time-series relative conversion blood circulation volume data into a plurality of components by singular value decomposition, principal component analysis, or independent component analysis (step S105). Here, the analysis unit 134 subjects each of the relative conversion blood circulation volume data to singular value decomposition in which the SVD of MATLAB (registered trademark) is used as the analysis tool. Specifically, in the singular value decomposition, for the time-series relative conversion blood circulation volume data, the factor is set to time data per predetermined time period (e.g. 30 seconds), and the measure is set to the relative conversion blood circulation volume data per pixel, as calculated from the relative RGB data at each time period. Then, the time-series relative conversion blood circulation volume data is decomposed into a plurality of components by singular value decomposition and a time distribution, a space distribution, and a singular value representing the magnitude of each component is calculated.

Additionally, the analysis unit 134 determines whether or not each component satisfies predetermined conditions in order to identify a component, from the plurality of components decomposed by the singular value decomposition, indicating an RGB change in the facial surface that reflects brain activity (step S106). The predetermined condition includes conditions such as, for example, that the amplitude of the component waveform of the component decomposed by singular value decomposition has correlation with changes at brain resting time and brain activated time (hereinafter referred to as "first condition"), and/or that there is a blood circulation volume change at a predetermined site on the human facial surface in the component decomposed by the singular value decomposition (hereinafter referred to as "second condition"). One or a plurality of conditions may be set as the predetermined condition determined by the analysis unit 134. In this case, the first condition is set as the predetermined condition.

Then, the analysis unit 134 extracts, from the plurality of components, a component that satisfies the predetermined condition as a determination component. Furthermore, the analysis unit 134 identifies, from the extracted determination components, components that satisfy all of the conditions included in the predetermined condition as components indicating an RGB change in the facial surface that reflects brain activity (step S107). Meanwhile, the analysis unit 134 determines that the components among the plurality of components that do not satisfy one or more of the conditions included in the predetermined condition are not components indicating an RGB change in the facial surface that reflects brain activity (step S108).

In this case, as described above, only one condition is set as the predetermined condition, and the brain function activation task is given to the individual for a set period of time while the time-series photographic image data is being acquired. Therefore, the brain resting time is defined as the period of time in which the brain function activation task is not being given to the individual, and the brain activated time is defined as the period of time in which the brain function activation task is being given to the individual. The analysis unit 134 conducts a comparative analysis of the component waveform of each component against the periods of time in which the brain function activation task is and is not being given. Using the results of this comparative analysis based on the component waveform data, the analysis unit 134 evaluates whether or not there is correlation between the component waveform of each component and each of the brain resting time and the brain activated time. Then, the analysis unit 32 extracts, from the plurality of components, a component evaluated as having correlation as a determination component that satisfies the predetermined condition. The analysis unit 134 identifies this determination component as a component indicating an RGB change in the facial surface that reflects brain activity. Meanwhile, the analysis unit 134 determines that, among the plurality of components, a component evaluated as not having correlation is the component that does not satisfy the predetermined condition, and is not the component indicating an RGB change in the facial surface that reflects human brain activity.

In this case, the brain function activation task is given to the individual for a set period of time while acquiring the time-series photographic image data of the facial surface, and the analysis unit 134 extracts the determination component on the basis thereof. However, the content of the first condition, that is, the means of extracting the determination component by the analysis unit 134, is not limited thereto. For example, when the component, among the plurality of components, indicating the component waveform that has correlation with the brain resting time and the brain activated time is already identified by previous experiments or the like, the analysis unit 134 extracts this identified component from the plurality of components as the determination component. Additionally, with the brain activity visualization device 110, in cases where human behavior, which is known to be related to the activation/resting of the brain, such as eye movement and blinking are detected, the analysis unit 134 may extract the determination component from the plurality of components by comparing and analyzing these detection results against the component waveform of each component and conducting an evaluation. Note that the criterion for the analysis unit 134 to determine whether or not the first condition is satisfied is appropriately decided by simulations, experiments, theoretical calculations, or the like, in accordance with the purpose of use of the brain activity visualization device 110 or the like.

Additionally, in cases where the second condition is set as the predetermined condition, the analysis unit 134 extracts the determination component on the basis of the presence/absence of a change in facial blood circulation volume at the predetermined site on the human facial surface. Specifically, the analysis unit 134 determines whether or not a change in the blood circulation volume has occurred at the forehead and/or the area around the paranasal sinuses, on the basis of the blood circulation volume distribution diagrams corresponding to the plurality of components decomposed by singular value decomposition. When a change in the blood circulation volume has occurred, the analysis unit 32 determines that said component satisfies the second condition. Meanwhile, when a change in the blood circulation volume has not occurred at the forehead or the area around the paranasal sinuses, the analysis unit 32 determines that said component does not satisfy the second condition. Note that the criterion for the analysis unit 134 to determine whether or not the second condition is satisfied is appropriately determined by simulations, experiments, theoretical calculations, or the like, in accordance with the purpose of use of the brain activity visualization device 110 or the like.

Furthermore, in cases where the blood circulation volume calculation unit 133 calculates the time-series blood circulation volume data based on the RGB data prior to being converted to the relative RGB data, a configuration is possible in which the analysis unit 134 determines whether or not the first condition and/or the second condition is satisfied and extracts a determination component from the plurality of components obtained by subjecting the blood circulation volume data to singular value decomposition or the like.

The estimation unit 135 estimates human brain activity on the basis of the component identified by the analysis unit 134 as a component indicating an RGB change in the facial surface that reflects human brain activity. Specifically, the estimation unit 135 estimates an amount of brain activity when acquiring the photographic image data of the facial surface, on the basis of the component waveform data of the component identified by the analysis unit 134.

(4-2-1) Modification Example 2A

As described above, smartphones, tablets (e.g. iPad (registered trademark)), and other portable terminals with built in imaging devices may be used as the camera 121. In other words, any device that captures images in the visible light region can be used for the photographic image data described above.

Additionally, in the blood circulation volume calculation unit 133, the blood circulation volume data of the facial surface may be calculated using mainly the R component of each pixel included in the RGB data. Provided that the blood circulation volume data can be calculated on the basis of the RGB data, the blood circulation volume data need not be limited to the erythema index.

(4-2-2) Modification Example 2B

The blood circulation volume calculation unit 133 described above calculates the relative conversion blood circulation volume data on the basis of relative RGB data converted by the conversion unit 132. However, in place of or in addition to this, the blood circulation volume calculation unit 133 may calculate the blood circulation volume data on the basis of RGB data prior to being converted to relative RGB data. Components having correlation with brain activity are more likely to be identified (statistical power is high) in blood circulation volume data calculated on the basis of RGB data prior to being converted to relative RGB data. As such, the blood circulation volume data calculated on the basis of RGB data prior to being converted to relative RGB data may be analyzed prior to the relative conversion blood circulation volume data calculated on the basis of relative RGB data. In addition, for example, first, the blood circulation volume data may be analyzed to extract the components having the significant correlation, and regarding the relative conversion blood circulation volume data, only the components corresponding to the extracted components may be analyzed, whereby the amount of the computation processing can be reduced.

(4-2-3) Modification Example 2C

In the description given above, the camera 121 was assumed to be a typical visible light range camera, but an infrared camera may also be used. In such cases, the infrared camera captures images by emitting infrared light and capturing the reflected waves thereof. The photographic image data of changes in the facial surface of the subject may be obtained in this manner. The present inventors found that there is correlation between the blood circulation volume data calculated from the photographic image data obtained from the reflection of the infrared light and the blood circulation volume data calculated using mainly the R component of each pixel included in the RGB data captured in the visible light region. Accordingly, it is also possible to estimate human brain activity using photographic image data obtained from the reflection of such infrared light.

(4-2-4) Modification Example 2D

Although in the above-mentioned description the brain activity visualization device 110 includes the image data acquisition means 120 and the brain activity estimation means 130, the brain activity visualization device according to the present embodiment is not limited to such a configuration. That is, the brain activity visualization device according to the present embodiment may have any configuration, as long as it includes the blood circulation volume calculation unit 133, the analysis unit 134, and the estimation unit 135. Specifically, the brain visualization device according to the present embodiment may take a form, including not only a form in which the device itself generates the image data by photographing, but also a form in which photographic image data is received from an external device to analyze it therein.

(4-3) State Visualization Means 200

The state visualization means 200 display and visualize the physiological state of the subject on the basis of the brain activity of the subject estimated by the brain activity estimation means 30 and/or the brain activity estimation means 130. In one example, the state visualization means 200 may include an analysis unit 201 that analyzes changes in the amount of brain activity of the subject in order to analyze the physiological state of the subject. Specifically, the analysis unit 201 determines the physiological state of the subject by analyzing changes in the amount of brain activity in response to stimulation (e.g. visual stimulation, auditory stimulation, tactile stimulation, olfactory stimulation, or taste stimulation) applied to the subject. Note that, the type and level of the physiological state may be appropriately configured in accordance with the use of the brain activity visualization devices 10, 110, on the basis of a degree of rise and/or duration of the amount of brain activity. Moreover, the state visualization means 200 has a display unit 202 that outputs the physiological state of the subject analyzed by the analysis unit 201. As a result, an administrator can ascertain the physiological state of the subject. The display unit 202 is not particularly limited, as long as it can visualize information related to the analyzed physiological state of the subject to the administrator. Examples thereof include display devices that display images, messages, and the like.

Additionally, in cases where acquiring various types of time-series data using the facial skin temperature acquisition means 20 and/or the image data acquisition means 120 after the analysis units 32, 134 have identified the components that reflect brain activity, the additionally acquired various types of data is decomposed into a plurality of components by singular value decomposition in the brain activity visualization devices 10, 110, and only the identified components are analyzed. As a result, the physiological state of the subject can be ascertained in real time.

There are techniques for acquiring heart rate information, biological information, and so on of the subject from the skin temperature or captured images of the facial surface of the subject. In addition, conventional techniques can be applied to the components obtained by performing the singular value decomposition or the like on the various data obtained from the facial skin temperature acquisition means 20 and/or the image data acquisition means 120. As such, heart rate information, biological information, or the like can be accurately acquired. Accordingly, a configuration is possible in which the analysis unit 32 and/or the analysis unit 134 is provided with a feature for analyzing the plurality of components obtained from the singular value decomposition and acquiring heart rate information, biological information, or the like, and the estimation units 33, 135 of the embodiment described above are provided with features for estimating functions of the sympathetic nervous system/parasympathetic nervous system on the basis of the acquired heart rate information and/or biological information.

(5) Features (5-1)

In the present embodiment, human brain activity is estimated on the basis of the time-series facial skin temperature data and/or facial blood circulation volume data acquired by the facial skin temperature acquisition means 20 and/or the image data acquisition means 120. As such, human brain activity can be estimated without using electroencephalogram electrodes or other sensors that require pretreatment before being applied. Accordingly, human brain activity can be easily estimated and the physiological state of the subject can be visualized on the basis of the estimated brain activity.

(5-2)

In cases where a situation is created in which the human brain is placed in states of activation and rest by actually giving and withholding the brain function activation task while the time-series facial skin temperature data and/or the image data is being acquired, it can be said that there is a high possibility that the component having correlation between the component waveform of each component and the brain activated time and the brain resting time is a component indicating a change in skin temperature and/or blood circulation volume that reflects brain activity.

In the present embodiment, the brain function activation task is given to the individual for a certain period of time while the facial skin temperature acquisition means 20 and/or the image data acquisition means 120 is acquiring the time-series facial skin temperature data and/or the image data. That is, in the present embodiment, the brain function activation task is actually given to and withheld from the individual and, as a result, a situation is created in which the human brain is placed in an activated state and a resting state. Moreover, the various time-series data thusly acquired is decomposed into a plurality of components by the singular value decomposition, each component is evaluated whether there is correlation between the component waveform thereof and the brain activated time and the brain resting time, and a component evaluated as having correlation is extracted from the plurality of components as the determination component. Thus, compared, for example, to a case in which a predetermined component identified in prior experiments or the like is extracted from the plurality of components as the extraction component, the probability of extraction of a component, which is less related to the human brain activity, as an extraction component from the plurality of components, can be reduced.

(5-3)

The brain has a mechanism called the selective brain cooling system whereby the brain is cooled independently of body temperature. The selective brain cooling system is known to discharge heat generated by brain activity using the forehead and the area around the paranasal sinuses. When heat is discharged, a change in the facial skin temperature resulting from brain activity or the facial blood circulation volume that correlates to the facial skin temperature appears at the forehead and/or the area around the paranasal sinuses.

In the present embodiment, various data of the forehead and/or the area around the paranasal sinuses is analyzed and the determination component is extracted. As such, it is possible to accurately extract components related to human brain activity.

(6) Use Examples of Brain Activity Visualization Device

Next, use examples of the brain activity visualization device according to the present disclosure will be described.

(6-1) When Used on a Patient

An example is described of a case in which the brain activity visualization devices 10, 110 according to the embodiment or the modification examples described above are used on a patient visiting a hospital, or the like. In one example, when using the brain activity visualization devices 10, 110 to objectively quantify a depression state, a brain function activation task such as mental arithmetic with carrying and borrowing is given to the patient, and a change in the amount of brain activity before and after giving the brain function activation task is analyzed and visualized. Thus, the mental state of the patient can be determined. Specifically, in cases where the amount of brain activity does not increase while the brain function activation task is being given, it can be determined that the patient is in a lethargic state, and even if the amount of brain activity increases while the brain function activation task is being given, if the time in which the amount of brain activity is increased is short, it can be determined that the patient is in a state of decreased energy. Such analyses are conducted multiple times over a one-day period and, when a decrease, on average, of the amount of brain activity is found, the patient can be determined to be in a depression state.

Additionally, in cases where using the brain activity visualization devices 10, 110 to determine the presence/absence of the consciousness of an emergency patient or whether or not a patient is awake, a stimulus such as rubbing the skin of the patient or speaking to the patient is given, and the change in the amount of brain activity before and after the administration of the stimulus is analyzed and visualized. Thus, it is possible to determine the presence/absence of the consciousness of the patient and/or whether or not the patient is awake. In one example, when the amount of brain activity increases while stimulating the skin or speaking to a patient to whom anesthesia has been given, it can be determined that the patient is awake. Accordingly, even if the patient is unable to speak, an administrator can ascertain the presence/absence of the consciousness of the patient and/or whether or not the patient is awake. Additionally, an awakeness degree (level) can be determined by changing the intensity of the stimulus given to the patient and analyzing for the presence/absence of brain activation at that time. Examples of stimuli of low intensity include stimuli such as squeezing a hand or moving a hand; and examples of stimuli of high intensity include stimuli whereby the body is subjected to a temperature change such as applying ice to a hand, and stimuli whereby pain is inflicted on the body.

When using the brain activity visualization devices 10, 110 to determine the effect of treatment such as rehabilitation, the brain function activation task such as mental arithmetic with carrying and borrowing is given to the patient, and the change in the amount of brain activity at that time is analyzed and visualized. Thus, the effects, on the patient, of treatment such as rehabilitation can be determined. For example, brain function activation tasks of the same intensity are given to a patient before and after rehabilitation, brain training, or exercise therapy, and changes in the amount of brain activity at that time are analyzed. As a result, an administrator can determine the effects of the treatment such as rehabilitation from the degree of rise and/or rising duration of the amount of brain activity. For example, in cases where the amount of brain activity does not increase when the brain function activation task is given to the patient, it can be determined that the patient is in a cerebrovascular ischemic state, and if the duration of the increased amount of brain activity is short, it can be determined that the patient is in a state of decreased cerebrovascular blood flow volume. Accordingly, the brain activity visualization devices 10, 110 can be used as monitoring devices in hyperbaric oxygen therapy apparatuses.

Furthermore, when using the brain activity visualization devices 10, 110 to quantify the pain of the patient, the pain level may be quantified on the basis of a change (particularly, the degree of rise in the amount of brain activity and the duration thereof) in the amount of brain activity when the patient is feeling pain (as declared by the patient). Moreover, these analysis results are visualized, which allows the administrator to ascertain the pain level of the patient.

(6-2) When Used on a Person Under Special Circumstances Such as being Subjected to Shock Waves An example is described of a case in which the brain activity visualization device s 10, 110 according to the embodiment or the modification examples described above are used on a person under special circumstances such as being subjected to explosion shock waves, such as a firefighter. When the brain activity visualization devices 10, 100 are used for biological protection determination due to being subjected to shock waves or the like (e.g. determining the state of biological damage received from shock waves), the brain function activation task is given to a subject, and the changes in the amount of brain activity at this time are analyzed and visualized. As a result, an administrator can estimate the cerebrovascular blood flow state of the subject. For example, in cases where the amount of brain activity does not increase when the brain function activation task is given to the subject, it can be determined that the subject is in a cerebrovascular ischemic state, and if the duration of the increased amount of brain activity is short, it can be determined that the patient is in a state of decreased cerebrovascular blood flow volume.

(6-3) When Used to Determine Comfort

An example is described of a case in which the brain activity visualization devices 10, 110 according to the embodiment or the modification examples described above are used to determine the comfort of a subject. For example, when using the brain activity visualization devices 10, 110 to determine the comfort of a dwelling, a discomfort level is quantified on the basis of a change (the degree of rise in the amount of brain activity and the duration thereof) in the amount of brain activity when the subject is in a predetermined dwelling space and is feeling discomfort (as declared by the patient). Such analyses are conducted multiple times over a one-day period and the analysis results thereof are visualized. As a result, the administrator can determine a degree of comfort, namely comfort-discomfort emotions, of the subject by evaluating whether or not the amount of brain activity is rising on average.

(6-4) When Used to Determine Concentration Level

An example is described of a case in which the brain activity visualization devices 10, 110 according to the embodiment or the modification examples described above are used to determine a concentration level when studying or performed surgery. For example, in a case where the brain activity visualization devices 10, 110 are used to quantify the concentration level of a student on the content of study in a school, cram school, company, e-learning course, or hospital, changes (the degree of rise in this time period) in the amount of brain activity of the student during certain periods of time (e.g. during study hall) before and after being engaged in study (tasks) are analyzed. As a result, the concentration level on the content of study the student is engaged in can be quantified. Thus, the administrator can evaluate the concentration level of the student on the content of study on the basis of visualized analysis results.

(7) Physiological State Determination Device

A physiological state determination device to which the brain activity visualization device according to the present disclosure is applied will be described. The physiological state determination device determines a mental or physical physiological state of the subject. Specifically, research conducted by the present inventors has shown that humans in a depression state demonstrate slower reactions to positive images (described later) than humans not in a depression state. Meanwhile, humans in a depression state tend to demonstrate greater response to negative images than humans not in a depression state. Thus, it is possible to use these characteristics to realize a depression state determination device that determines the depression state. Furthermore, the present inventors have gone one step farther and conceived a physiological state determination device that determines a variety of mental or physical physiological states.

(7-1) Configuration of Physiological State Determination Device

Figure 23:
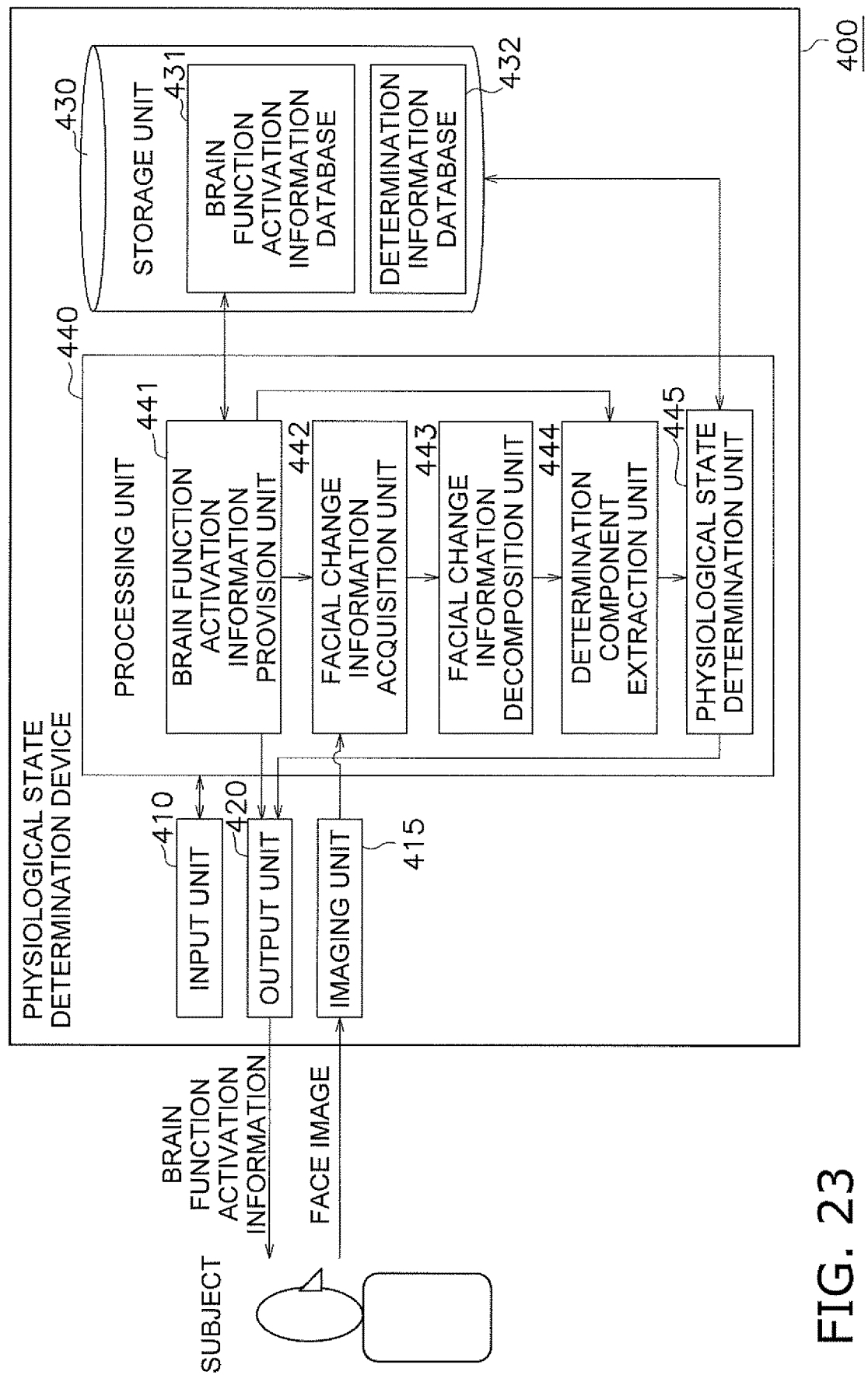
FIG. 23 is a schematic drawing illustrating a configuration of a physiological state determination device according to an embodiment of the present disclosure.

FIG. 23 is a schematic drawing illustrating an example of the physiological state determination device according to the present embodiment. Note that, in the following description, a device that determines mental states, particularly "depression states", as physiological states is given by way of example.

A physiological state determination device 400 includes an input unit 410, an imaging unit 415, an output unit 420, a storage unit 430, and a processing unit 440.

The input unit 410 is configured to input various information into the physiological state determination device 400. The input unit 410 is configured with, for example, a keyboard, a mouse, and/or a touchscreen, or the like. Various commands are input into the physiological state determination device 400 via the input unit 410, and processing is executed in the processing unit 440 in accordance with the commands.

The imaging unit 415 is configured to capture "face images" including the facial surface of the subject 300. The imaging unit 415 is configured with, for example, a CCD, CMOS, or similar solid state imaging device that acquires RGB images, and an infrared camera or the like that acquires thermograms. Infrared cameras and the like preferably are capable of detection with high sensitivity under typical room temperature conditions, namely from 29.0° C. to 37.0° C. In addition, the imaging unit 415 is capable of continuous imaging at predetermined intervals. Face images are preferably captured from the front and under constant illumination. In cases where front images cannot be obtained due to posture fluctuations, the perturbation space method is used to approximate a three-dimensional shape of the facial surface for images with varying postures, and obtain a face image by rendering the three-dimensional shape in a front view. For images with illumination fluctuations, an illumination base model of the facial surface based on the diffuse reflection model is used to obtain face images under constant illumination conditions. Then, the continuously captured face images are sent from the imaging unit 415 to the processing unit 440.

The output unit 420 is configured to output various information from the physiological state determination device 400. In one example, the output unit 420 is configured with a display and a speaker, or the like. In this case, brain function activation information (described later) is provided to the subject 300 via the output unit 420.

The storage unit 430 stores information including the information input into the physiological state determination device 400, the information calculated by the physiological state determination device 400, and the like. In one example, the storage unit 430 is configured with memory, a hard disk device, or the like. Programs for realizing the various functions of the processing unit 440 (described below) are also stored in the storage unit 430. In this case, the storage unit 430 includes a brain function activation information database 431 and a determination information database 432.

The brain function activation information database 431 stores brain function activation information that activates human brain function. Here, an example of the "brain function activation information" is an emotional image classified by its comfort to humans and a reaction level thereto. From the perspective of comfort, the "emotional image" is classified into negative images and positive images. Specifically, the positive images are images that increase the psychological comfort of humans such as photographs of brides, photographs of playing puppies, smiling people, beautiful snow-covered mountain landscapes, and flowers. The negative images are images that decrease the psychological comfort of humans such as people with sad expressions, cityscapes of desolate slums, murder scenes from television programs, insects, spiders, and snakes, and photographs of hospitals. However the "brain function activation information" is not limited thereto and predetermined visual information can be used that includes one or any combination of the emotional image, an image exposure image, a substance image, an image depicting a cognitive task, light stimulation information, and an image depicting a sensory stimulation task.

Figure 24:
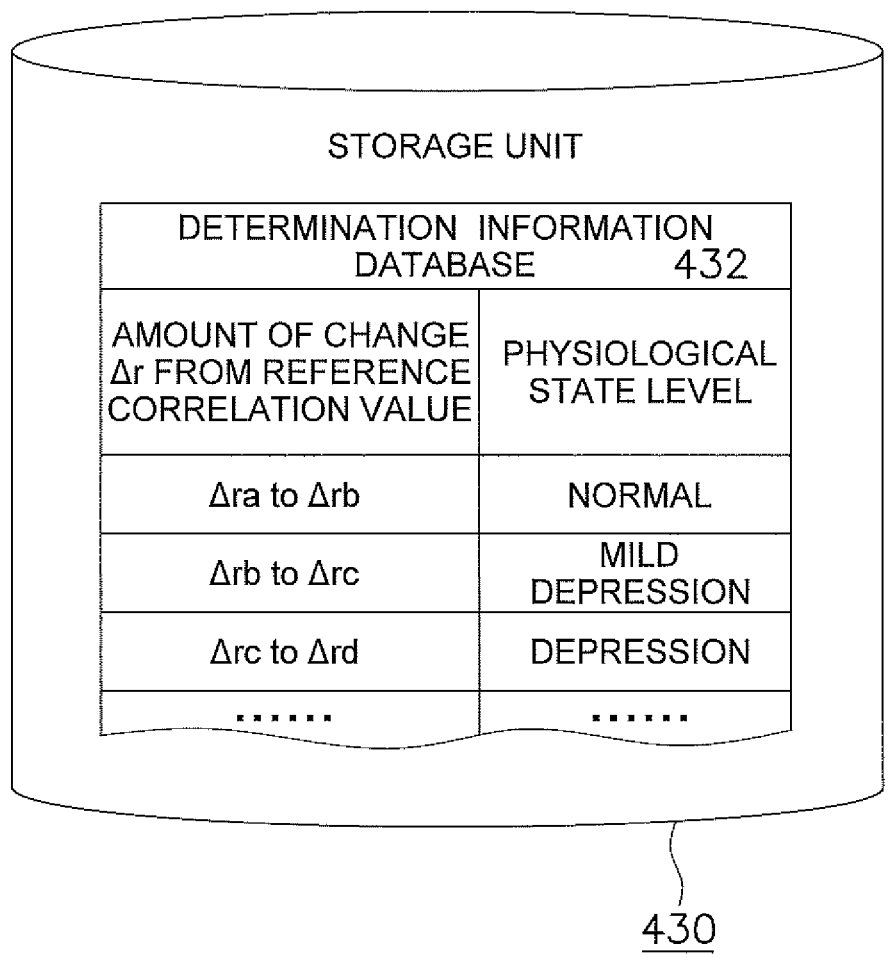
FIG. 24 is a schematic drawing illustrating a configuration of a determination information database of the physiological state determination device.

The determination information database 432, as illustrated in FIG. 24, stores "determination information". A "physiological state level" is associated with an amount of change Δr (=r1−r2) of a predetermined range and stored, in advance, as determination information in the determination information database 432. The amount of change Δr is defined as an amount of change of a correlation value r2 of a determination component extracted in accordance with the provision of the positive image from a "reference correlation value" r1 of a reference determination component extracted in accordance with the provision of the negative image. The "reference determination component" is configured from data of determination components extracted in accordance with the provision of the negative image, data of previously extracted determination components, data of determination components provided from an external source, or the like. In the example illustrated in FIG. 24, a case in which the "depression state" is determined as the physiological state level is depicted. Specifically, the determination information database 432 stores the physiological state levels associated with the range of the value of the amount of change Δr. Here, Δr=Δra to Δrb indicates a physiological state level of "normal", Δr=Δrb to Δrc indicates a physiological state level of "mild depression", and Δr=Δrc to Δrd indicates a physiological state level of "depression." In this case, values increase in the order of Δra, Δrb, Δrc, and Δrd. Note that data of the reference determination component may also be stored in the determination information database 432. Additionally, in this case, determination information for determining the "depression state" is stored in the determination information database 432, but when determining other physiological states, determination information corresponding thereto is stored in the determination information database 432.

The processing unit 440 is configured to execute information processing in the physiological state determination device 400. Specifically, the processing unit 440 is configured with a CPU, cache memory, and the like. The processing unit 440 executes the programs incorporated into the storage unit 430 to function as a brain function activation information provision unit 441, a facial change information acquisition unit 442, a facial change information decomposition unit 443, a determination component extraction unit 444, and a depression state determination unit 445.

The brain function activation information provision unit 441 is configured to provide the brain function activation information. In one example, in accordance with operations of the input unit 410, the brain function activation information provision unit 441 reads the brain function activation information from the brain function activation information database 431 and outputs this brain function activation information to the output unit 420.

The facial change information acquisition unit 442 is configured to acquire "facial data" and "facial change information" indicating time-series changes in the facial data from the face images captured by the imaging unit 415. Specifically, the facial change information acquisition unit 442 acquires the facial data from the imaging unit 415 in synchronization with the timing at which the brain function activation information provision unit 441 provides the brain function activation information. Moreover, the facial change information acquisition unit 442 acquires facial change information indicating time-series changes in the facial data of the subject 300 from continuously acquired facial data. In an example in which 60 pieces of facial data of 240×320 pixels are acquired at predetermined intervals, the facial change information is a set of 4,608,000 pieces of data. The acquired facial change information is sent to the facial change information decomposition unit 443. Note that, when the imaging unit 415 is an infrared camera, the facial change information acquisition unit 442 acquires facial skin temperature data indicating the facial skin temperature of the subject 300 as the facial data. Additionally, when the imaging unit 415 is a CCD, CMOS, or similar solid state imaging device, the facial change information acquisition unit 442 acquires facial blood circulation volume data based on RGB data of the facial surface of the subject 300 as the facial data. Note that a configuration is possible in which the facial change information acquisition unit 442 acquires data of the forehead and/or the area around the paranasal sinuses of the subject 300 as the facial data.

The facial change information decomposition unit 443 decomposes the facial change information, which is a set of multiple pieces of data, into a plurality of components 1, 2, 3 . . . by singular value decomposition, principal component analysis, or independent component analysis. Information of each of the decomposed components is sent to the determination component extraction unit 444. In this case, when the facial change information is subjected to singular value decomposition or the like, the components 1, 2, 3 . . . are numbered in descending order of the singular value. Components with higher singular values are more likely to reflect the influence of components that fluctuate greatly. As such, the influence of noise and the like of the external environment, and not the influence imparted by the brain function activation information, is often reflected in the component 1.

The determination component extraction unit 444 is configured to extract, from the plurality of components 1, 2, 3 . . . , a component related to the brain function activation information as the "determination component". Additionally, the determination component extraction unit 444 calculates a correlation value r of the extracted determination component to the brain function activation information. Specifically, the determination component extraction unit 444 calculates the correlation value r between the brain function activation information and the plurality of components 1, 2, 3 . . . decomposed by the facial change information decomposition unit 443. Next, when the calculated correlation value r is greater than or equal to a predetermined value, the determination component extraction unit 444 determines the component corresponding to that correlation value r to be a component related to the brain function activation information. Then, the determination component extraction unit 444 extracts the determination component on the basis of a value of a risk factor. Specifically, the determination component extraction unit 444 extracts a component for which the risk factor is low as the determination component. The extracted determination component and calculated correlation value r are sent to the storage unit 430 or the physiological state determination unit 445.

The physiological state determination unit 445 calculates a difference Δr between a reference correlation value r1 to the reference determination component extracted in accordance with the provision of the negative image, and a correlation value r2 to a determination component extracted in accordance with the positive image. Then, the physiological state determination unit 450 determines the physiological state level corresponding to the difference Δr between the reference correlation value r1 and the correlation value r2 on the basis of the determination information stored in the determination information database 432. The determined physiological state level is output via the output unit 420 to a display device or the like.

(7-2) Operations of Physiological State Determination Device

Figure 25A:
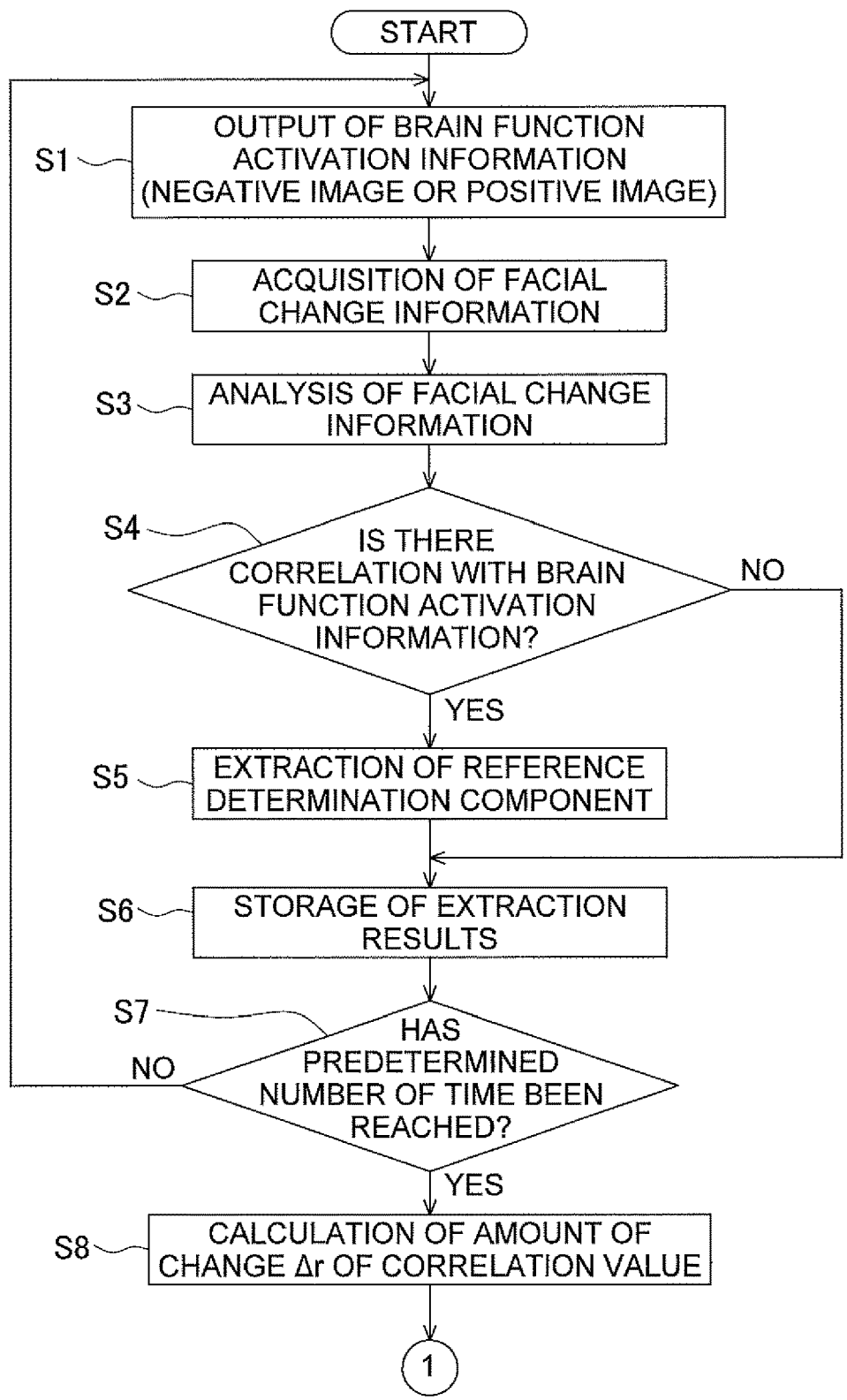
FIG. 25A is a flowchart showing operations of the physiological state determination device.
Figure 25B:
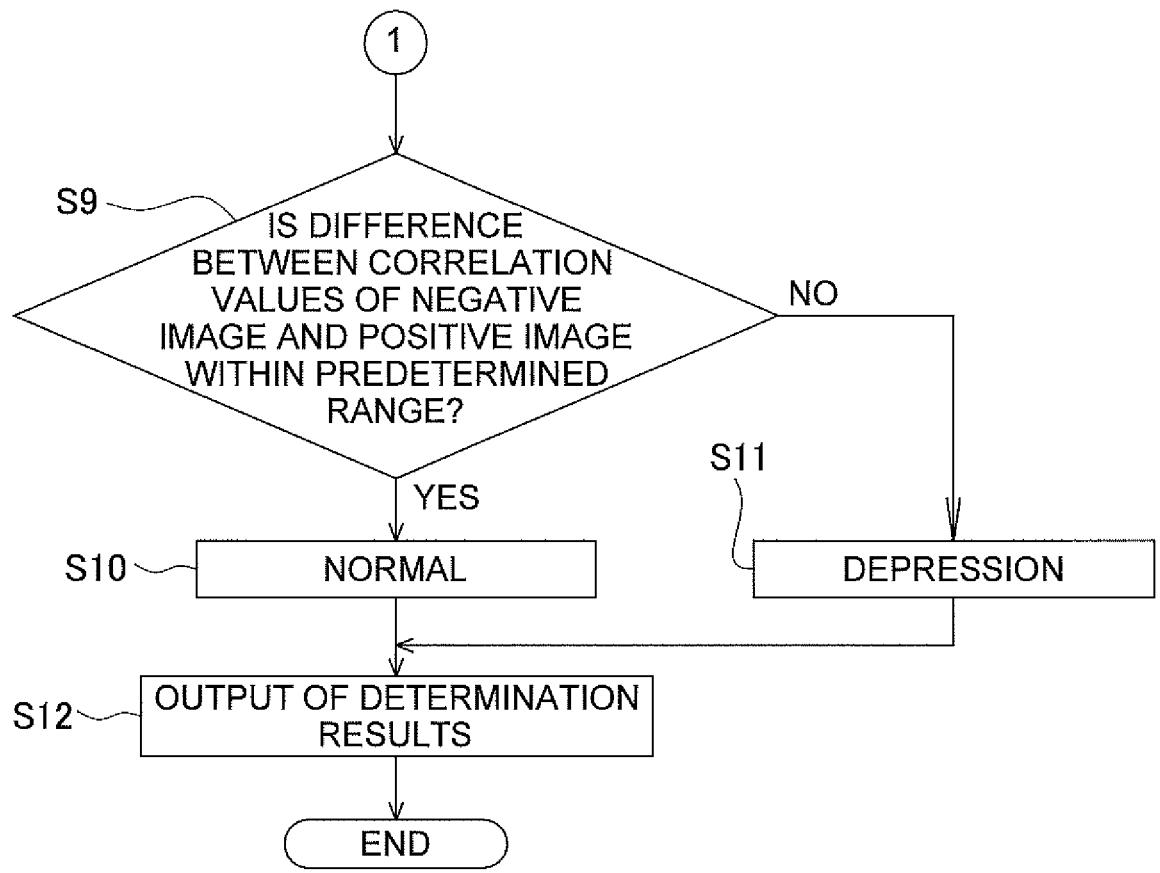
FIG. 25B is a flowchart showing operations of the physiological state determination device.

FIG. 25 is a flowchart showing operations of the physiological state determination device 400. In the following description, a device that determines mental states, particularly a "depression state", is given by way of example.

First, a command to start measurement is input via the input unit 410 into the physiological state determination device 400. At this time, the name and/or subject number of the test subject, namely the subject 300, is input. Next, a guidance screen is displayed on the output unit 420 and the face of the subject 300 is guided so as to be positioned at the center of the guidance screen.

Figure 26:
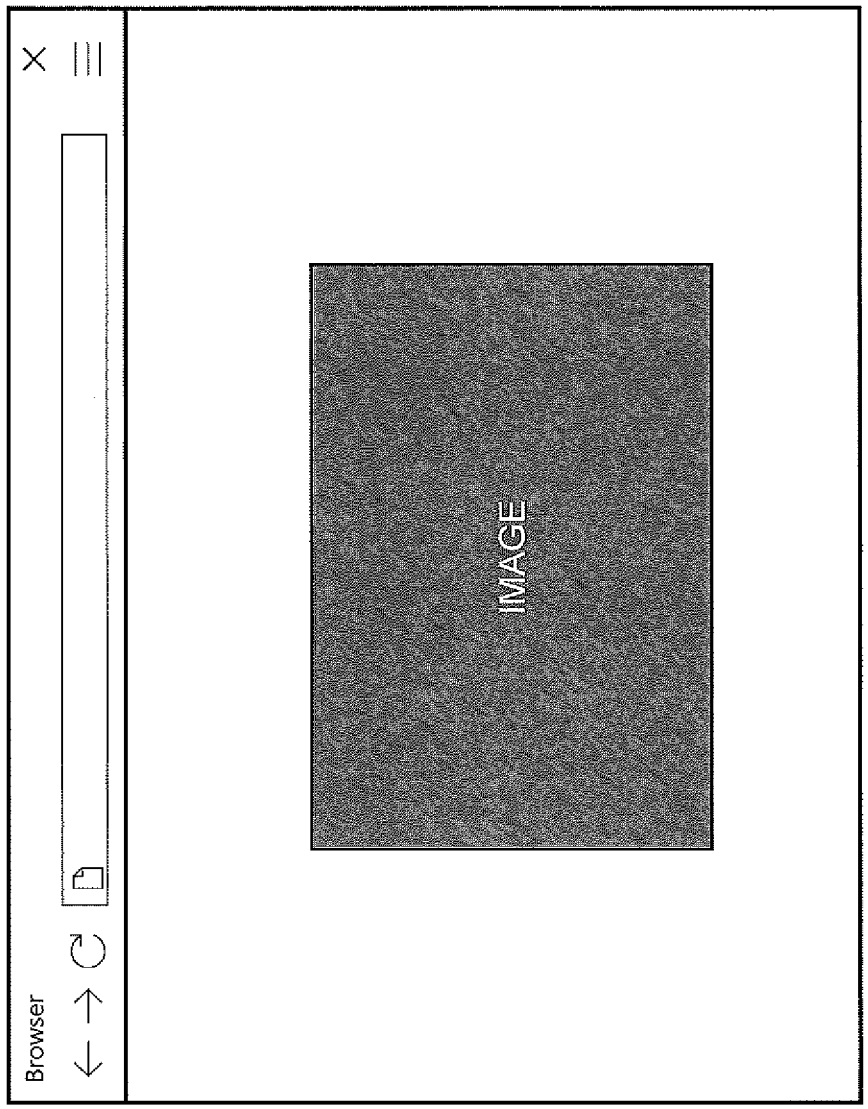
FIG. 26 is a schematic drawing illustrating an example of a display screen output by the physiological state determination device.

Then, an output command for the brain function activation information is input into the physiological state determination device 400. As a result, the brain function activation information is read from the brain function activation information database 431 and an image display screen such as that illustrated in FIG. 26 is output to the output unit 420 (S1). In this case, a rest image, a negative image, and a positive image are sequentially output to the output unit 420 as the brain function activation information. The rest image is a neutral image of blank paper, cross marks, or the like.

Figure 27:
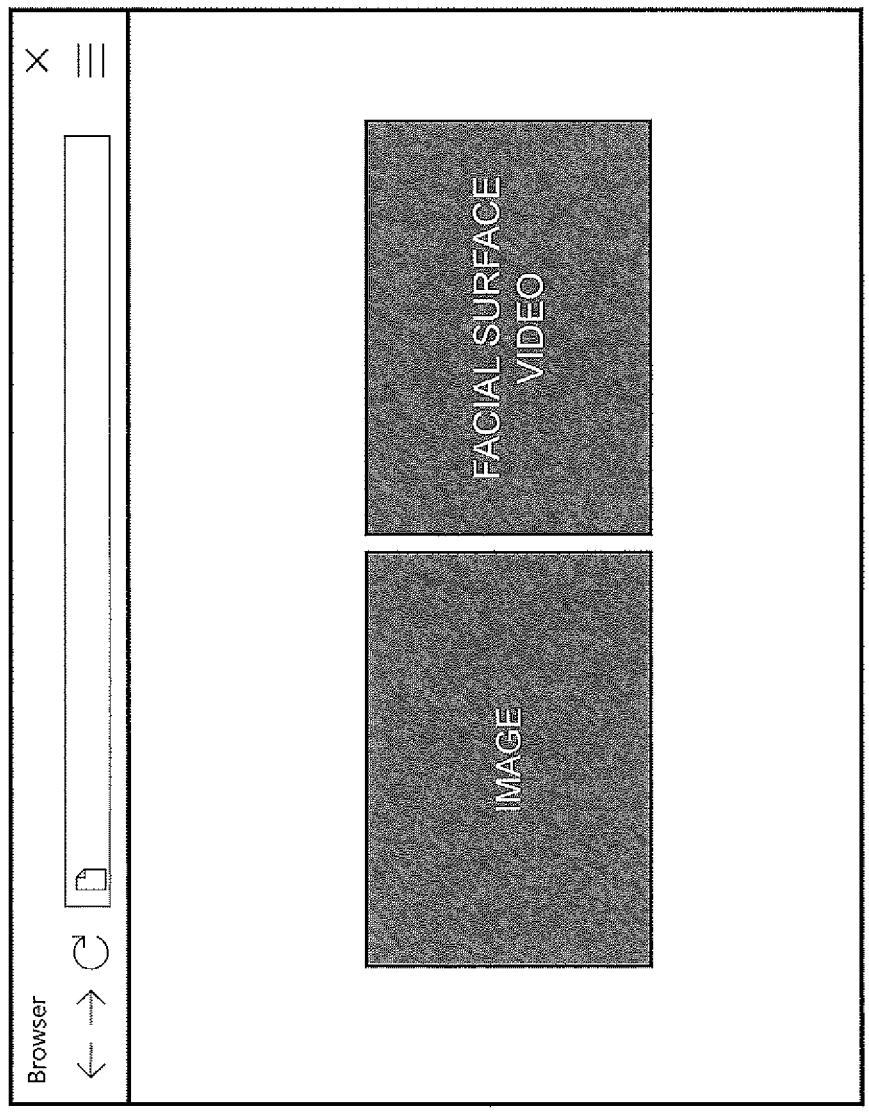
FIG. 27 is a schematic drawing illustrating an example of an image display screen after imaging, output by the physiological state determination device.

Next, simultaneously with the output of the brain function activation information or at a predetermined timing, the imaging unit 415 captures face images of the subject 300 positioned in front of the output unit 420. The face images are captured at predetermined intervals (S2). The captured face images are sent to the facial change information acquisition unit 442. Then, after a predetermined period of time has passed, image display is ended and, simultaneously, video imaging of the face is ended. At this time, as illustrated in FIG. 27, the acquired face image and the image displayed at that time are displayed such that the contents of both images can be confirmed.

Next, in the physiological state determination device 400, an analysis of the captured face images is conducted. Specifically, the facial change information acquisition unit 442 acquires facial change information indicating time-series changes in the facial data of the subject 300 from the acquired facial data. Then, the facial change information decomposition unit 443 decomposes the facial change information into the plurality of components 1, 2, 3 . . . by singular value decomposition, principal component analysis, or independent component analysis (S3).

Next, the determination component extraction unit 444 calculates the correlation value between the brain function activation information and the plurality of components 1, 2, 3 . . . decomposed by the facial change information decomposition unit 443. Then, the determination component extraction unit 444 determines whether or not the correlation value is greater than or equal to the predetermined value (S4). When the correlation value is determined to be greater than or equal to the predetermined value, it is determined that "there is correlation" between the brain function activation information and that component (S4—Yes). Then, the determination component extraction unit 44 extracts, from among the components having correlation, a component for which the risk factor is low as the "determination component" (S5). Additionally, the determination component extraction unit 444 categorizes the correlation value between the brain function activation information and the determination component into the positive images or negative images category and stores the correlation value in the storage unit 430 (S6). Meanwhile, when the correlation value between the brain function activation information and each of the components 1, 2, 3 . . . is less than the predetermined value, it is determined that "there is no correlation" therebetween, and that information is stored in the storage unit 430 (S4—No, S6).

Figure 28:
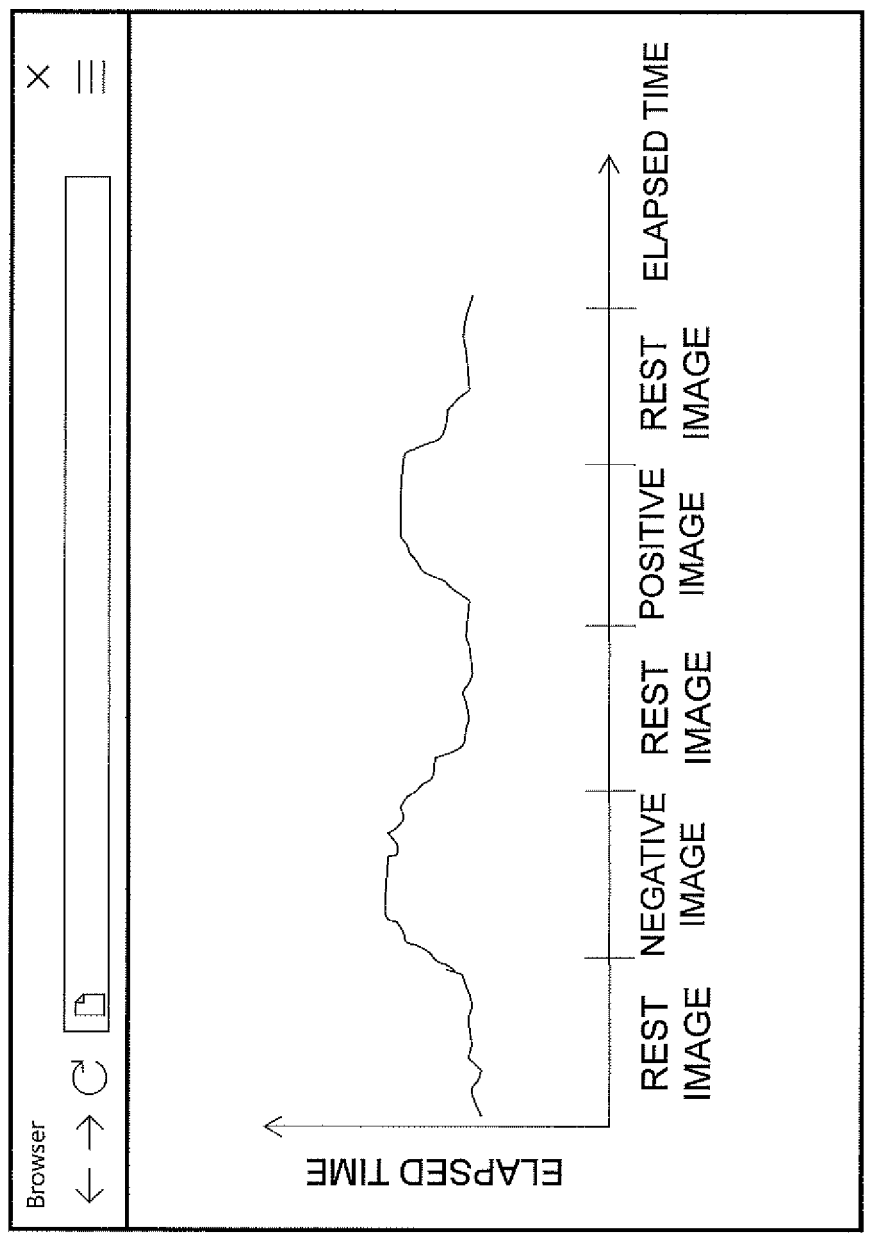
FIG. 28 is a schematic drawing illustrating an example of an analysis waveform display screen output by the physiological state determination device.
Figure 29:
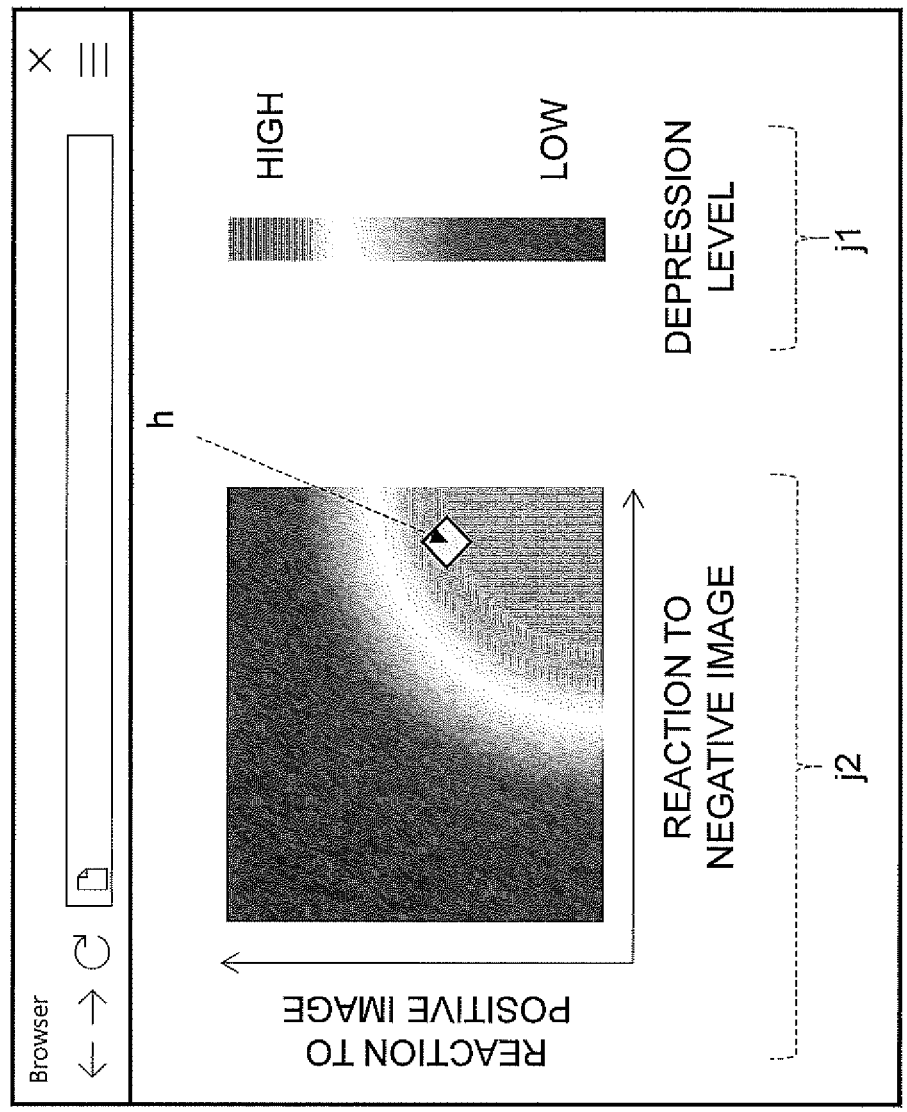
FIG. 29 is a schematic drawing illustrating an example of a distribution map display screen output by the physiological state determination device.

Thereafter, the steps S1 to S6 are executed a predetermined number of times (S7). Then, the physiological state determination unit 445 calculates the amount of change $\Delta r$, which is the difference between reference correlation value r1 to the reference determination component extracted in accordance with the provision of the negative image and the correlation value r2 to the determination component extracted in accordance with the provision of the positive image (S8). Next, the physiological state determination unit 450 determines whether or not the amount of change $\Delta r$ between the correlation value r2 and the reference correlation value r1 is within a predetermined range (S9). Whether or not the amount of change $\Delta r$ is within the predetermined range is determined by referencing the determination information stored in the determination information database 432. When the amount of change $\Delta r$ between the correlation value r2 and the reference correlation value r1 is within the predetermined range, the physiological state determination unit 445 determines that the subject 300 is "normal" (S9—Yes, S10). When the amount of change $\Delta r$ between the correlation value r2 and the reference correlation value r1 is not within the predetermined range, the physiological state determination unit 445 determines that the subject 300 is in a "depression state" (S9—No, S11). In one example, it is determined that the subject 300 is normal when the amount of change $\Delta r$ is in the range $\Delta ra$ to $\Delta rb$ described above, and that the subject 300 is in a physiological state when the amount of change $\Delta r$ exceeds $\Delta rb$. These determination results are output as determination results via the output unit 420 to a display device or the like (S12). At this time, the output unit 420 may display an analysis waveform such as that illustrated in FIG. 28. Alternatively, the output unit 420 may display a distribution map such as that illustrated in FIG. 29. Here, a color scale or gray scale (j1) on the right side of FIG. 29 expresses the physiological state level (in this case, the depression state level). In the two-dimensional distribution (j2) on the left side of FIG. 29, the degree of response to the negative image is shown on the horizontal axis, the degree of response to the positive image is shown on the vertical axis, and a point h plotted thereon represents the state of the subject.

Thereafter, the physiological state determination device 400 saves the data in accordance with an input command by a device user. Specifically, the physiological state determination device 400 associates the determination results data, the analysis waveforms, the measurement results, the image display conditions, and the like with each subject and stores those data in the storage unit.

(7-3) Features of Physiological State Determination Device (7-3-1)

As described above, the physiological state determination device 400 according to the present embodiment includes the brain function activation information provision unit 441, the facial change information acquisition unit 442, the facial change information decomposition unit 443, the determination component extraction unit 444, and the physiological state determination unit 445. The brain function activation information provision unit 441 provides the "brain function activation information", which activates human brain function, to the subject 300. The facial change information acquisition unit 422 acquires the "facial change information" indicating time-series changes in the facial data of the subject 300. The facial change information decomposition unit 433 decomposes the facial change information into the plurality of components 1, 2, 3 . . . by singular value decomposition, principal component analysis, or independent component analysis. The determination component extraction unit 444 extracts, from the plurality of components 1, 2, 3 . . . , a component related to the brain function activation information as the "determination component". The physiological state determination unit 445 determines the physiological state of the subject 300 on the basis of the determination component.

Accordingly, with the physiological state determination device 400 according to the present embodiment, the plurality of components 1, 2, 3 . . . are obtained by subjecting the facial change information to singular value decomposition, principal component analysis, or independent component analysis, and the determination component related to the brain function activation information is extracted from the plurality of components 1, 2, 3 . . . . As such, the presence/absence of brain activity of the subject 300 can be easily estimated without using electrodes or the like that require pretreatment before being applied. As a result, the physiological state of the subject 300 can be easily determined on the basis of the determination component corresponding to the brain function of the subject 300.

Figure 30:
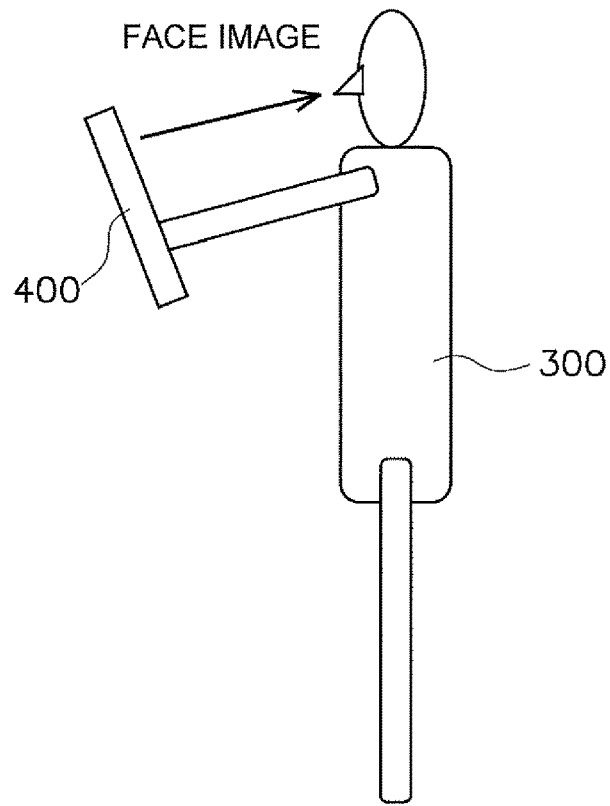
FIG. 30 is a schematic drawing illustrating an example of a specific form of the physiological state determination device.
Figure 31:
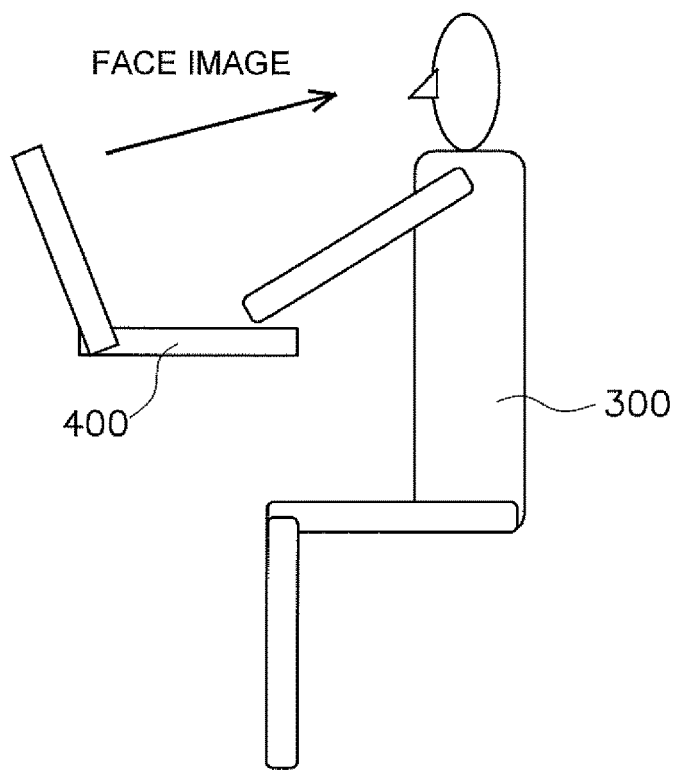
FIG. 31 is a schematic drawing illustrating an example of a specific form of the physiological state determination device.

Note that a configuration is possible in which the physiological state determination device 400 according to the present embodiment is incorporated into a smart device, as illustrated in FIG. 30. Additionally, a configuration is possible in which the physiological state determination device 400 is incorporated into a laptop computer, as illustrated in FIG. 31. These configurations enable the easy performance of physiological state determination at any location.

Note that, in the description given above, an example of a case was described in which the "depression state" was particularly determined as the physiological state. However, the physiological state determination unit 400 can determine any physiological state that is determinable by the configuration described above. For example, the physiological state determination device 400 can determine, as the mental state of the subject, one state or any combination of states of a mood disorder, an anxiety disorder, a substance-related disorder, dementia, and autism on the basis of the determination component. In particular, the physiological state determination unit 445 can determine, as the mood disorder state, one state or any combination of a depression state, schizophrenia, and bipolar disorder. Additionally, the physiological state determination device 400 can determine the physical state of the subject in addition to the mental state. Moreover, when determining the depression state, primarily, the response to the positive image was compared with the response to the negative image. However, when determining other physiological states, processing appropriate to that physiological state is carried out.
(7-3-2)
With the physiological state determination device 400 according to the present embodiment, the facial change information acquisition unit 442 acquires data of the forehead and/or the area around the paranasal sinuses of the subject 300 as the facial data. As a result, the determination component related to brain activity can be extracted with high accuracy. The brain has a mechanism called the selective brain cooling system whereby the brain is cooled independently of body temperature. The selective brain cooling system is known to discharge heat generated by brain activity using the areas around the forehead and the paranasal sinuses. Thus, the component related to brain activity can be extract with high accuracy by analyzing data from these sites. As a result, the physiological state determination device 400 according to the present embodiment can execute physiological state determination with high accuracy.

(7-3-3)
With the physiological state determination device 400 according to the present embodiment, the facial change information acquisition unit 442 acquires facial skin temperature data indicating the facial skin temperature of the subject 300 as the facial data. In other words, the physiological state determination device 400 is capable of using an infrared camera or the like to determine the physiological state.
(7-3-4)
With the physiological state determination device 400 according to the present embodiment, the facial change information acquisition unit 442 acquires facial blood circulation volume data based on RGB data of the facial surface of the subject 300 as the facial data. In other words, the physiological state determination device 400 can use a solid state imaging device (CCD, CMOS) to determine the physiological state. As a result, physiological state determination can be executed with a simple configuration.
(7-3-5)
With the physiological state determination device 400 according to the present embodiment, the determination component extraction unit 444 extracts the determination component on the basis of the value of the risk factor. With the physiological state determination device 400, the determination component related to the brain function activation information is extracted on the basis of the value of the risk factor. As such, the reliability of the physiological state determination can be enhanced.
(7-3-6)
With the physiological state determination device 400 according to the present embodiment, the brain function activation information provision unit 441 provides the emotional image classified as the negative image or the positive image as the brain function activation information and, as a result, a determination component related to brain activity can be extracted. Thus, the physiological state of the subject can be easily determined.
(7-3-7)
The physiological state determination device 400 according to the present embodiment includes the determination information database 432. The amount of change Δr of the predetermined range is associated with the physiological state level and stored as the "determination information" in the determination information database 432. The amount of change Δr is defined as the amount of change, of the correlation value r2 of the determination component calculated in accordance with the provision of the positive image, from the reference correlation value r1 of the reference determination component calculated in accordance with the provision of the negative image. Then, the physiological state determination unit 445 calculates the correlation value r2 of the determination component to the provision of the positive image, and determines the physiological state level of the subject 300 on the basis of the calculated correlation value r2 and the determination information.

As a result of this configuration, the physiological state determination device 400 can use the reference determination component extracted in accordance with the provision of the positive image to easily determine the physiological state level. That is, the physiological state determination device 400 is capable of not only determining the presence/absence of a physiological state, but also determining and outputting the physiological state level.
(7-3-8)
A physiological state determination method according to the present embodiment does not necessarily require the physiological state determination device 400. That is, regardless of whether or not the physiological state determination device 400 is provided, it is sufficient that the physiological state determination method according to the present embodiment include a brain function activation information provision step for providing the subject 300 with, as brain function activation information that activates human brain function, the emotional image classified as the positive image; then, after the provision of the positive image, a facial change information acquisition step for acquiring "facial change information" indicating time-series changes in the facial data of the subject; a facial change information decomposition step for decomposing the facial change information into a plurality of components by singular value decomposition, principal component analysis, or independent component analysis; a determination component extraction step for extracting a component related to the brain function activation information as a determination component from the plurality of components; and a physiological state determination step for determining, on the basis of the determination component, the physiological state of the subject.

According to this physiological state determination method, the plurality of components is obtained by subjecting the facial change information to singular value decomposition, principal component analysis, or independent component analysis after the provision of the emotional image, and the determination component related to the brain function activation information is extracted from the plurality of components. As such, the physiological state of the subject 300 can be easily determined.

(7-3-9)

With the physiological state determination device 400 described above, the reference correlation value r1 is set in accordance with the provision of the negative image, but a configuration is possible in which the reference correlation value is set in accordance with the provision of the positive image. In this case, "the physiological state level" is associated with the amount of change Δr of the predetermined range and stored, in advance, as the "determination information" in the determination information database 432. The amount of change Δr is defined as the amount of change of the correlation value r2 of the determination component extracted in accordance with the provision of the negative image from the "reference correlation value" r1 of the reference determination component extracted in accordance with the provision of the positive image. The physiological state determination unit 445 calculates the difference Δr, which is the difference between the reference correlation value r1 calculated in accordance with the provision of the positive image and the correlation value r2 calculated in accordance with the provision of the negative image. Then, the physiological state determination unit 450 determines the physiological state level corresponding to the difference Δr between the reference correlation value r1 and the correlation value r2 on the basis of the determination information stored in the determination information database 432.

(7-3-10)

A configuration is possible in which the physiological state determination device 400 does not only determine the physiological state using the correlation value with the reference value of the determination component as described above, but also determines the physiological state on the basis of one or any combination of the correlation value with the reference value of the determination component, a value obtained by subjecting the determination component to multiple regression analysis, area that the waveform corresponding to the determination component generates, an average value of the waveforms corresponding to the determination components, and the centroid value of the waveform corresponding to the determination component.

(7-4) Modification Example of Physiological State Determination Device

Figure 32:
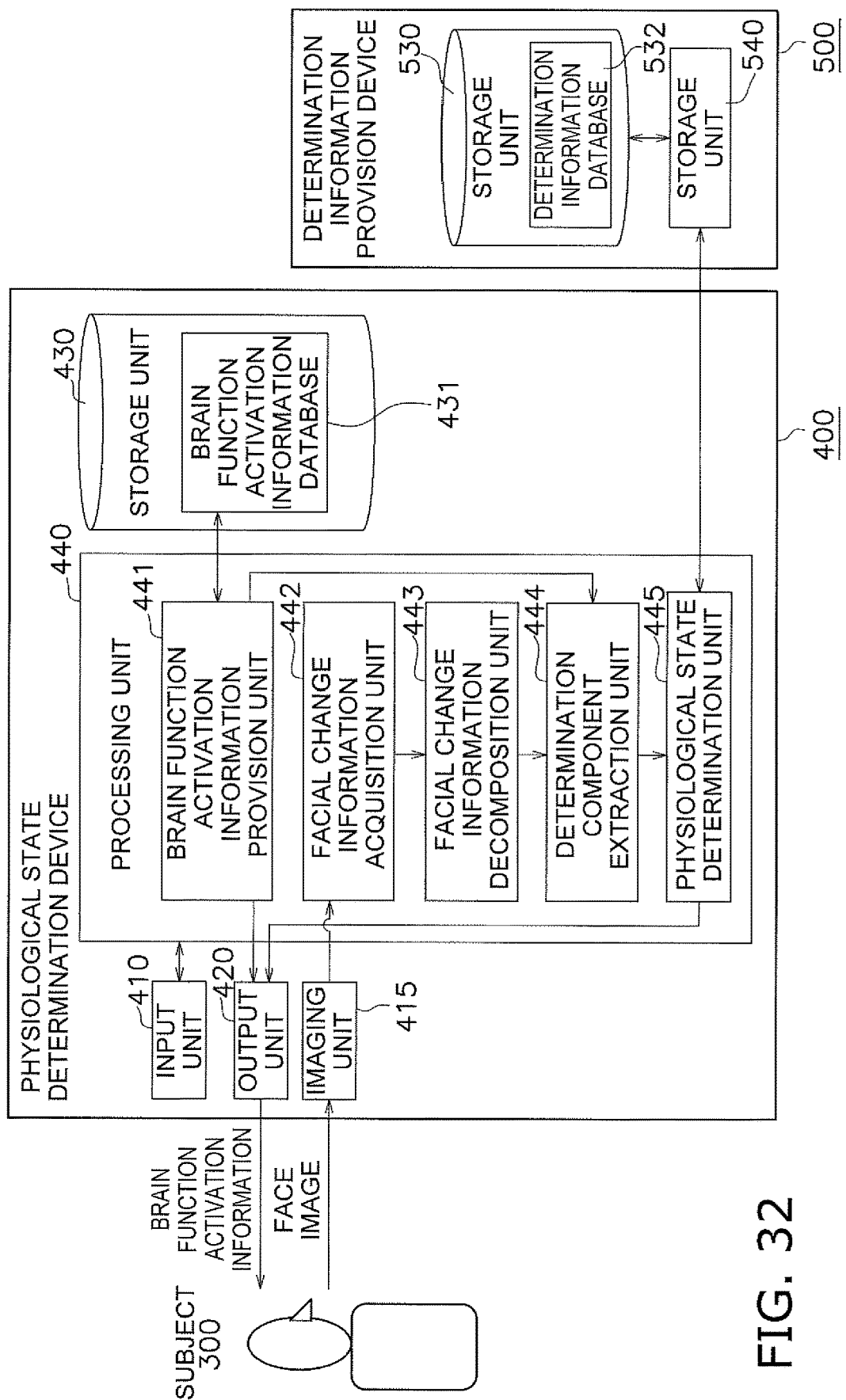
FIG. 32 is a schematic drawing illustrating a configuration of a modification example of the physiological state determination device.

As illustrated in FIG. 32, a configuration is possible in which a determination information provision device 500 or the like provided on a network is used in the physiological state determination device 400 according to the present embodiment.

In this case, the determination information provision device 500 includes a storage unit 530 and a processing unit 540.

The storage unit 530 includes a determination information database 532. This determination information database 532 has the same configuration as the determination information database 432 described above. That is, the physiological state level is associated with the amount of change Δr of the predetermined range and stored as the determination information in the determination information database 532. The amount of change Δr is defined as the amount of change of the correlation value r2 of the determination component calculated in accordance with the provision of the negative image from the reference correlation value r1 of the reference determination component calculated in accordance with the provision of the positive image.

The processing unit 540 sends the determination information stored in the determination information database 532 in accordance with requests from the physiological state determination device 400. A configuration is possible in which the processing unit 540 has a function for generating, on the basis of predetermined information, determination information as big data, independent of the determination component extracted by the physiological state determination device 400. Additionally, in cases where the reference correlation value r1 is calculated by the physiological state determination device 400, the processing unit 540 executes processing for updating the reference correlation value r1 stored in the determination information database 432 in a timely manner.

In the present modification example, the physiological state determination unit 445 issues requests to the determination information provision device 500 for the provision of the determination information. Specifically, with the physiological state determination device 400 of the present modification example, the determination information database 532 is stored in the determination information provision device 500, which is on the network, and the physiological state determination unit 445 accesses the determination information provision device 500 when determining the physiological state level. Moreover, the physiological state determination unit 445 determines the physiological state level of the subject 300 on the basis of the calculated correlation value r2 and the determination information.

Accordingly, with the physiological state determination device 400 of the present modification example, the physiological state determination unit 445 can use an external network to determine the physiological state level of the subject 300.

Additionally, the physiological state determination unit 445 determines the physiological state using the reference determination component stored in the determination information provision device 500, which is on the external network. As such, it is possible to omit the provision of the negative image. That is, as illustrated in FIG. 33, a configuration is possible in which only the positive image is provided as the brain function activation information.

Figure 33:
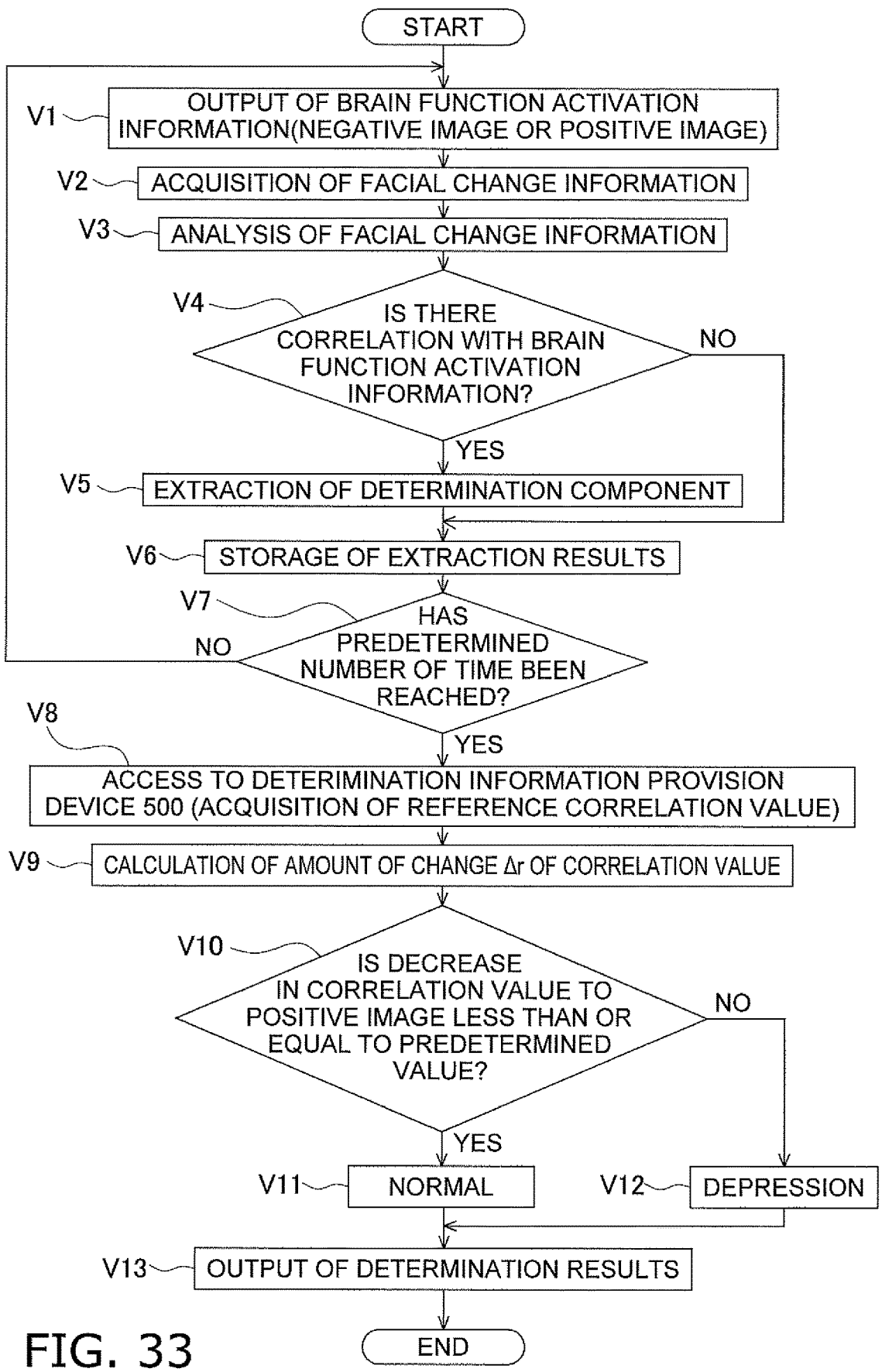
FIG. 33 is a flowchart showing operations of the modification example of the physiological state determination device.

FIG. 33 is a flowchart for describing the physiological state determination method in the present modification example. In the present modification example, as the brain function activation information, only the positive image is provided to the subject 300 (V1). The processing described above for steps S2 to S7 is performed in steps V2 to V7. As a result, the reference correlation value r2 calculated in accordance with the provision of the positive image is calculated in the physiological state determination device 400. Next, in step V8, the physiological state determination device 400 issues a send request to the determination information provision device 500 for the determination information. As a result, the physiological state determination device 400 acquires the reference correlation value r1 calculated in accordance with the provision of the negative image. Next, the physiological state determination unit 450 determines whether or not the amount of change Δr between the correlation value r2 and the reference correlation value r1 is within the predetermined range (V9 to V12). Then, the determination results are output via the output unit 420 to a display device or the like (V13). Thus, the reference determination component stored in the determination information provision device on the external network is used to determine the physiological state.

The steps described above may be executed in part without using the physiological state determination device 400.

Furthermore, with the physiological state determination method of the present modification example, big data can be used to determine the physiological state. That is, the reference correlation value r1 and the predetermined amount of change Δr are obtained from big data. Specifically, the positive image is provided to a person other than the subject 300 to extract the reference determination component, and the reference correlation value r1 that is calculated on the basis of this reference determination component is used. As a result, the determination information can be optimized in a timely manner.

In the modification example described above, a method is described in which only the positive image is provided to determine the physiological state, but a configuration is also possible in which only the negative image is provided to determine the physiological state. That is, a configuration is possible in which a physiological state is determined to be present when the correlation value to the negative image is higher than the reference correlation value stored in the determination information provision device on the network.

(7-5) Verification of Physiological State Determination Method

A verification experiment of the physiological state determination method according to the present embodiment was carried out under the following conditions. Specifically, here, as the physiological state, the determination of a mental state, particularly a "depression state", was verified.

In the experiment, 25 images of each of the negative image and the positive image were used. Each image was presented for 4.8 seconds. The subject was seated one meter away from a large-screen television on which the images were displayed. To perform the measurement, RGB image data was acquired using a camera with a face tracking feature. In the measurement, first, two minutes of rest were provided, then, the emotional images were presented for the next two minutes, and then two minutes of rest were provided and the measurement was ended.

Figure 34:
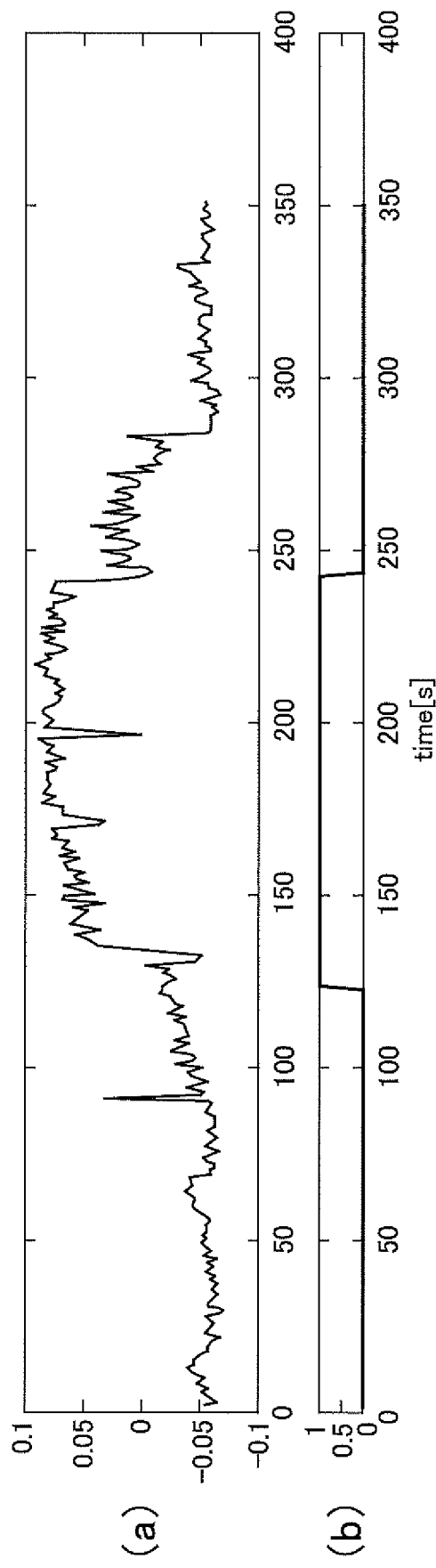
FIG. 34 is a chart illustrating a waveform of a determination component obtained when a positive image was presented.
Figure 35:
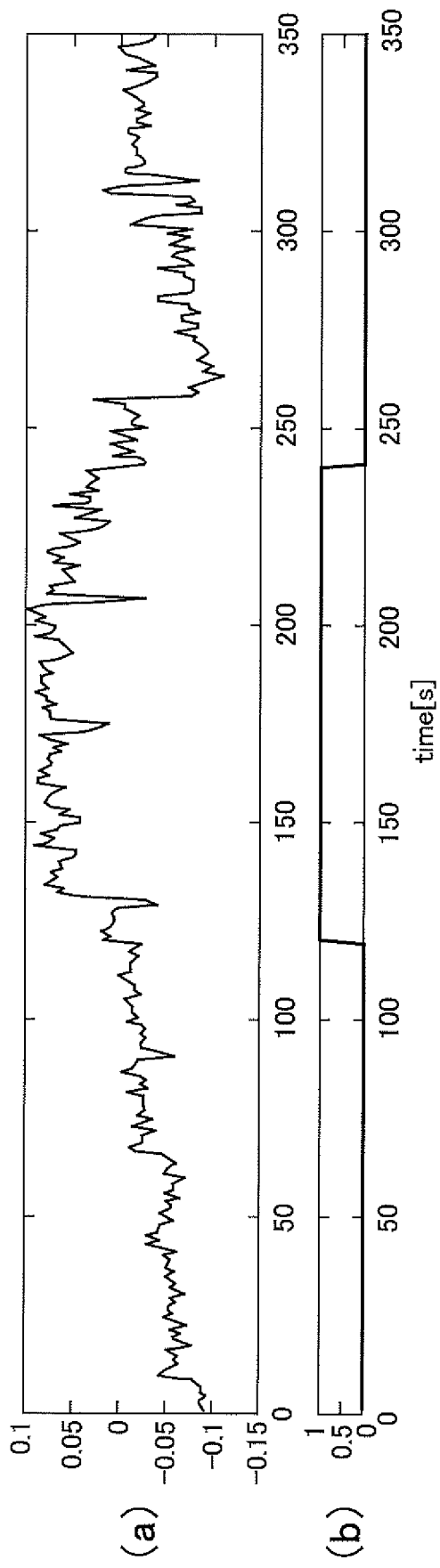
FIG. 35 is a chart illustrating a waveform of a determination component obtained when a negative image was presented.

FIG. 34 is a chart illustrating a waveform of the determination component obtained when a positive image was presented to a certain subject; and FIG. 35 is a waveform of the determination component obtained when the negative image was presented. In the examples illustrated in FIGS. 34 and 35, section (a) depicts the waveform of the determination component, and section (b) depicts the timing at which the positive image or the negative image was presented. In this case, the correlation value of the determination component to the provision of the positive image was 0.86. However, the correlation value of the determination component to the negative image was also 0.86. Accordingly, it was confirmed that there was correlation with the determination component not only in the provision of the positive image, but also in the provision of the negative image. This subject scored a 3 on the CES-D depression scale, which indicates normal with "slight depression tendencies". From these results, it was confirmed that the activation of brain function can be estimated by providing the emotional images, and that the provision of emotional images can be used to determine physiological states, particularly "depression states".

Additional Description

The present disclosure is not limited to the embodiments described above. Various modifications may be made to the constituents of the present disclosure at the stage of implementation, without departing from the gist of the present disclosure. Various types of the disclosure can be formed by appropriately combining a plurality of the constituent elements disclosed in the foregoing embodiments. Some of the constituent elements, for example, may be omitted from the whole of the constituent elements shown in the embodiments mentioned above. Furthermore, the constituent elements over different embodiments may be appropriately combined.

INDUSTRIAL APPLICABILITY

The present disclosure can easily estimate brain activity and, as such, is useful for applications to brain activity visualization devices that visualize the physiological state of subjects on the basis of brain activity.

The invention claimed is:

1. A physiological state determination system, comprising:
   a CPU; and
   a camera, the camera acquiring a photographic image data of a time-series change in facial data of a subject to which brain function activation information that activates human brain function was provided, the camera acquiring the photographic image data by photographing a region that includes at least one of a paranasal sinus area and a forehead area of the subject,
   the CPU acquiring facial change information from the photographic image data and determining a mental or physical physiological state of the subject based on the facial change information by:
      decomposing the facial change information into a plurality of components corresponding to at least a plurality of time distributions (V),
      extracting, from the plurality of components, a component related to the brain function activation information as a determination component, the determination component being extracted based on a value of a risk factor, and determining the mental or physical physiological state of the subject based on the determination component.

2. The physiological state determination system according to claim 1, wherein
the plurality of components further include components corresponding to space distributions (U).

3. The physiological state determination system according to claim 1, wherein
the CPU decomposes the facial change information into the plurality of components by singular value decomposition, principal component analysis, or independent component analysis.

4. The physiological state determination system according to claim 1, wherein
the CPU is incorporated in a smart device or a PC.

5. The physiological state determination system according to claim 4, further comprising:
an external device on a network.

6. The physiological state determination system according to claim 1, wherein
the brain function activation information is predetermined visual information, and
the CPU determines, as a mental state of the subject, one state or any combination of states including a mood disorder, an anxiety disorder, a substance-related disorder, dementia, and autism.

7. The physiological state determination system according to claim 6, wherein
the visual information is one or any combination of an emotional image, an image exposure image, a substance image, an image depicting a cognitive task, light stimulation information, and an image depicting a sensory stimulation task.

8. The physiological state determination system according to claim 1, wherein
the CPU provides the brain function activation information to the subject.

9. The physiological state determination system according to claim 1, further comprising:
a display device,
the CPU estimating the physiological state of the subject by estimating brain activity of the subject based on the facial change information, and
the display device displaying and visualizing the physiological state.

10. The physiological state determination system according to claim 9, wherein
the CPU decomposes the facial change information into a plurality of components by singular value decomposition, principal component analysis, or independent component analysis, and
estimates the brain activity of the subject based on the plurality of components.

11. The physiological state determination system according to claim 1, further comprising:
a physiological state determination device that includes the CPU and the camera, and
a determination information provision device that includes a memory, and that is accessed by the physiological state determination device through a network.

12. The physiological state, determination system according to claim 1, wherein
the determination is conducted based on data from a person other than the subject.

13. The physiological state determination system according to claim 1, wherein
the facial change information is related to selective brain cooling.

14. The physiological state determination system according to claim 1, wherein
the facial change information is color information related to a blood circulation volume.

15. The physiological state determination system according to claim 14, wherein
the color information is RGB data of the photographic image data.

16. A physiological state determination system, comprising:
a CPU; and
a camera, the camera acquiring a photographic image data of a time-series change in facial data of a subject to which brain function activation information that activates human brain function was provided, the camera acquiring the photographic image data by photographing a region that includes at least one of a paranasal sinus area and a forehead area of the subject; and
a memory storing an amount of change of a predetermined range, associated with a physiological state level, of a correlation value of a determination component calculated for the brain function activation information, from a reference correlation value of a reference determination component calculated for the brain function activation information, as determination information,
the CPU acquiring facial change information from the photographic image data and determining a mental or physical physiological state of the subject based on the facial change information by:
decomposing the facial change information into a plurality of components corresponding to at least a plurality of time distributions (V),
extracting, from the plurality of components, a component related to the brain function activation information as a determination component,
determining the mental or physical physiological state of the subject based on the determination component,
the CPU being further configured to:
calculate the correlation value of the determination component from the brain function activation information, and
determine, the physiological state level of the subject based on the calculated correlation value and the determination information.

17. A physiological state determination system, comprising:
a CPU that is incorporated in a smart device or a PC;
a camera, the camera acquiring a photographic image data of a time-series change in facial data of a subject to which brain function activation information that activates human brain function was provided, the camera acquiring the photographic image data by photographing a region that includes at least one of a paranasal sinus area and a forehead area of the subject; and
an external device on a network, the external device being a determination information provision device that includes a memory, the memory storing an amount of change of a predetermined range, associated with a physiological state level, and the amount of change is defined as an amount of change, of a correlation value of a determination component calculated for the brain function activation information, from a reference correlation value of a reference determination component calculated for the brain function activation information, the CPU acquiring facial change information from the photographic image data and determining a mental or physical physiological state of the subject based on the facial change information, wherein the CPU is further configured to
acquire determination information by accessing the determination information provision device,
calculate the correlation value of the determination component from the brain function activation information, and
determine the physiological state level of the subject based on the calculated correlation value and the determination information.

18. A physiological state determination system, comprising:

a CPU; and a camera, the camera acquiring a photographic image data of a time-series change in facial data of a subject to which brain function activation information that activates human brain function was provided, the camera acquiring the photographic image data by photographing a region that includes at least one of a paranasal sinus area and a forehead area of the subject, the CPU acquiring facial change information from the photographic image data and determining a mental or physical physiological state of the subject based on the facial change information, wherein the brain function activation information is an emotional image classified as a negative image or a positive image from a perspective of comfort to humans, and the CPU determines a depression state of the subject.

19. A physiological state determination system, comprising:

a CPU; and a camera, the camera acquiring a photographic image data of a time-series change in facial data of a subject to which brain function activation information that activates human brain function was provided, the camera acquiring the photographic image data by photographing a region that includes at least one of a paranasal sinus area and a forehead area of the subject; and a display device, the CPU acquiring facial change information from the photographic image data and determining a mental or physical physiological state of the subject based on the facial change information, wherein the CPU estimates the physiological state of the subject by estimating brain activity of the subject based on the facial change information and analyzes at least one of presence and absence of consciousness of the subject based on the brain activity of the subject, and the display device displays and visualizes the physiological state.

20. A physiological state determination system, comprising:

a CPU; and a camera, the camera acquiring a photographic image data of a time-series change in facial data of a subject to which brain function activation information that activates human brain function was provided, the camera acquiring the photographic image data by photographing a region that includes at least one of a paranasal sinus area and a forehead area of the subject; and a display device, the CPU acquiring facial change information from the photographic image data and determining a mental or physical physiological state of the subject based on the facial change information, wherein the CPU estimates the physiological state of the subject by estimating brain activity of the subject based on the facial change information and analyzes whether or not the subject is awakening based on the brain activity of the subject, and the display device displays and visualizes the physiological state.

21. A physiological state determination system, comprising:

a CPU; and a camera, the camera acquiring a photographic image data of a time-series change in facial data of a subject to which brain function activation information that activates human brain function was provided, the camera acquiring the photographic image data by photographing a region that includes at least one of a paranasal sinus area and a forehead area of the subject; and a display device, the CPU acquiring facial change information from the photographic image data and determining a mental or physical physiological state of the subject based on the facial change information, wherein the CPU estimates the physiological state of the subject by estimating brain activity of the subject based on the facial change information and analyzes comfort and discomfort emotions of the subject in a target space based on the brain activity of the subject, and the display device displays and visualizes the physiological state.

* * * * *